US009732313B2

(12) United States Patent
Hirschel et al.

(10) Patent No.: US 9,732,313 B2
(45) Date of Patent: Aug. 15, 2017

(54) METHOD AND APPARATUS FOR VIRUS AND VACCINE PRODUCTION

(71) Applicant: BIOVEST INTERNATIONAL, INC., Tampa, FL (US)

(72) Inventors: Mark Hirschel, Blaine, MN (US); Joseph David Gangemi, College Station, TX (US)

(73) Assignee: BIOVEST INTERNATIONAL, INC., Tampa, FL (US)

( * ) Notice: Subject to any disclaimer, the term of this patent is extended or adjusted under 35 U.S.C. 154(b) by 33 days.

(21) Appl. No.: 14/528,007

(22) Filed: Oct. 30, 2014

(65) Prior Publication Data

US 2015/0175950 A1    Jun. 25, 2015

Related U.S. Application Data

(63) Continuation of application No. 14/122,309, filed as application No. PCT/US2012/041942 on Jun. 11, 2012, now abandoned.

(60) Provisional application No. 61/496,898, filed on Jun. 14, 2011, provisional application No. 61/496,432, filed on Jun. 13, 2011, provisional application No. 61/495,882, filed on Jun. 10, 2011.

(51) Int. Cl.
| | | |
|---|---|---|
| C12N 7/00 | (2006.01) | |
| C12M 1/00 | (2006.01) | |
| C12M 3/00 | (2006.01) | |
| C12M 1/12 | (2006.01) | |
| C12M 1/34 | (2006.01) | |
| C12M 1/36 | (2006.01) | |

(52) U.S. Cl.
CPC ............ *C12M 23/28* (2013.01); *C12M 23/34* (2013.01); *C12M 23/44* (2013.01); *C12M 25/10* (2013.01); *C12M 29/04* (2013.01); *C12M 41/12* (2013.01); *C12M 41/32* (2013.01); *C12M 41/48* (2013.01); *C12M 47/12* (2013.01); *C12N 7/00* (2013.01); *C12N 2760/16051* (2013.01)

(58) Field of Classification Search
None
See application file for complete search history.

(56) References Cited

U.S. PATENT DOCUMENTS

| | | |
|---|---|---|
| 4,804,628 A | 2/1989 | Cracauer et al. |
| 4,973,558 A | 11/1990 | Wilson et al. |
| 5,330,915 A | 7/1994 | Wilson et al. |
| 5,416,022 A | 5/1995 | Amiot |
| 5,541,105 A | 7/1996 | Melink et al. |
| 5,631,006 A | 5/1997 | Melink et al. |
| 5,656,421 A | 8/1997 | Gebhard et al. |
| 5,998,184 A | 12/1999 | Shi |
| 6,001,585 A | 12/1999 | Gramer |
| 7,160,464 B2 * | 1/2007 | Lee ................ A61L 2/0017 210/175 |
| 8,383,397 B2 | 2/2013 | Wojciechowski et al. |
| 8,540,499 B2 | 9/2013 | Page et al. |
| 2005/0064584 A1 | 3/2005 | Bargh |
| 2009/0162901 A1 | 6/2009 | Chen et al. |
| 2009/0215022 A1 | 8/2009 | Page et al. |
| 2009/0269841 A1 * | 10/2009 | Wojciechowski ..... C12M 23/28 435/325 |
| 2011/0212493 A1 | 9/2011 | Hirschel et al. |
| 2012/0114634 A1 | 5/2012 | Stergiou et al. |
| 2013/0058907 A1 | 3/2013 | Wojciechowski et al. |
| 2014/0024012 A1 | 1/2014 | Page et al. |

FOREIGN PATENT DOCUMENTS

| | | | | |
|---|---|---|---|---|
| WO | WO 2005/087915 | 9/2005 | | |
| WO | WO 2005/090403 | 9/2005 | | |
| WO | WO 2007/136821 | 11/2007 | | |
| WO | WO 2007/139742 | 12/2007 | | |
| WO | WO 2007/139746 | 12/2007 | | |
| WO | WO 2007/139747 | 12/2007 | | |
| WO | WO 2007/139748 | 12/2007 | | |
| WO | WO 2008/098165 | 8/2008 | | |
| WO | WO 2010/042644 | 4/2010 | | |
| WO | WO 2010/048417 | 4/2010 | | |
| WO | WO 2010/048417 A2 * | 4/2010 | ............. | C12M 3/02 |
| WO | WO 2012/021840 | 2/2012 | | |
| WO | WO 2012/064760 | 5/2012 | | |
| WO | WO 2012/171026 | 12/2012 | | |
| WO | WO 2012/171030 | 12/2012 | | |
| WO | WO 2013/086418 | 6/2013 | | |

OTHER PUBLICATIONS

Vester D et al., "Virus-host cell interactions in vaccine production cell lines infected with different human influenza A virus variants: A proteomic approach" Journal of Proteomics, 2010, 73:1656-1669.

* cited by examiner

*Primary Examiner* — Agnieszka Boesen
(74) *Attorney, Agent, or Firm* — Saliwanchik Lloyd & Eisenschenk

(57) ABSTRACT

The invention concerns a bioreactor for production of virus and virus-like particles (VLPs), methods for production of virus and VLPs, methods for regulating the concentration of molecules inhibitory to viral and VLP yield in a cell culture chamber of a bioreactor, such as the extracapillary space of a hollow fiber bioreactor.

16 Claims, 38 Drawing Sheets

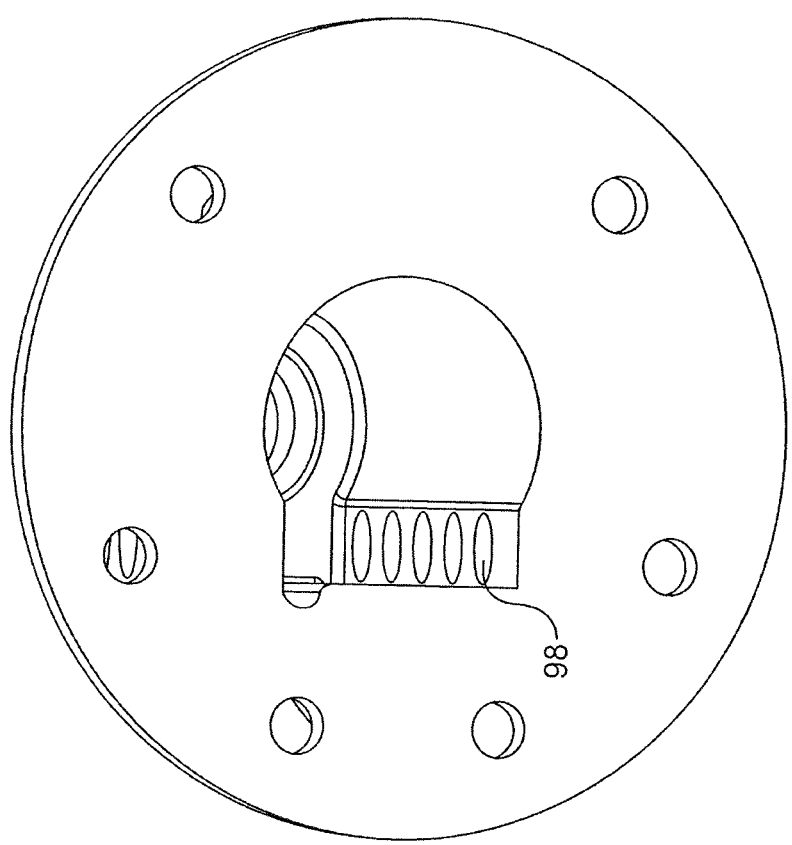

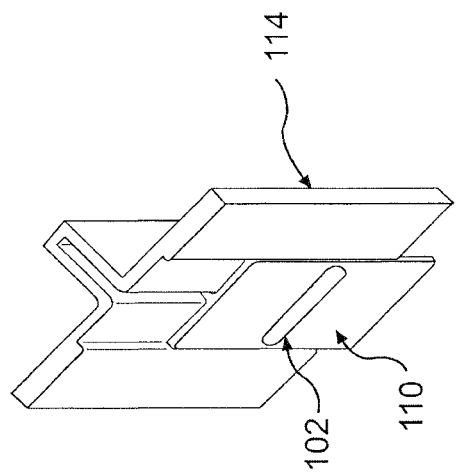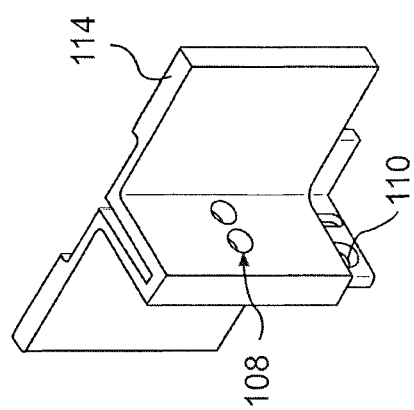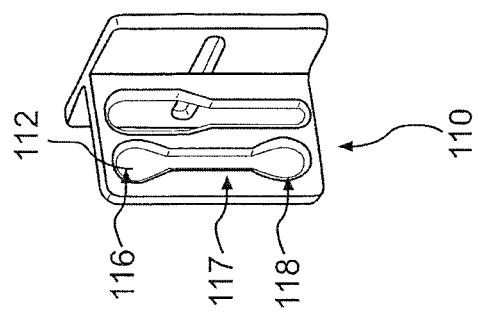

| | | | | | | | | | | |
|---|---|---|---|---|---|---|---|---|---|---|
| OCT. 01, 2004 9:47.43 | AIR INLET PRESSURE LOW | | | | | | | | | |
| OCT. 01, 2004 9:47.43 | PH 6.65 | GAS 0.0 | ICP 0 | ECP 0 | ECS FALL | REF.T 1.6 | MED.T 25.0 | INC.T 26.1 | OUT 0 | MED 100 | FACT 0 | HARV 0 | CIRC 200 |
| OCT. 01, 2004 9:47.49 | FALL CYCLE COMPLETE IN 0:03 | | | | | | | | | |
| OCT. 01, 2004 9:48.26 | STARTUP, DOWN TIME: 0-00:00 | | | | | | | | | |
| OCT. 01, 2004 9:49.48 | RISE CYCLE COMPLETE IN 0:02 | | | | | | | | | |
| OCT. 01, 2004 9:52.44 | PH 7.10 | GAS 50.8 | ICP 0 | ECP 51 | ECS FALL | REF.T 5.2 | MED.T 38.1 | INC.T 48.7 | OUT 125 | MED 100 | FACT 0 | HARV 0 | CIRC 200 |
| OCT. 01, 2004 9:54.53 | FALL CYCLE COMPLETE IN 5:05 | | | | | | | | | |
| OCT. 01, 2004 9:55.29 | RISE CYCLE COMPLETE IN 0:36 | | | | | | | | | |
| OCT. 01, 2004 9:57.45 | PH 7.10 | GAS 49.8 | ICP 0 | ECP 51 | ECS FALL | REF.T 5.0 | MED.T 37.4 | INC.T 48.7 | OUT 125 | MED 100 | FACT 0 | HARV 0 | CIRC 200 |
| OCT. 01, 2004 9:58.59 | INSTRUMENT HOLD, PUMPS STOPPED | | | | | | | | | |
| OCT. 01, 2004 9:59.00 | INSTRUMENT RESUMED FROM HOLD | | | | | | | | | |

TOTAL: 278    RECORDS 158 THRU 168    FREE: 0.0 MB

TOP | PG UP | ◁ | ▷ | PG DN | END

HOLD | EXIT | HELP

*FIG. 28*

METHOD AND APPARATUS FOR VIRUS AND VACCINE PRODUCTION

CROSS-REFERENCE TO RELATED APPLICATIONS

This application is a continuation of U.S. application Ser. No. 14/122,309, filed Nov. 26, 2013, which is the National Stage of International Application No. PCT/US2012/041942, filed Jun. 11, 2012, which claims the benefit of U.S. Provisional Application Ser. No. 61/495,882, filed Jun. 10, 2011, U.S. Provisional Application Ser. No. 61/496,432, filed Jun. 13, 2011, and U.S. Provisional Application Ser. No. 61/496,898, filed Jun. 14, 2011, the disclosure of each of which is incorporated herein by reference in its entirety, including all figures, tables and drawings.

BACKGROUND OF THE INVENTION

The anticipated growth of cell culture-based virus production will require new paradigms for rapid, high-throughput, harvest, purification, concentration and formulation of a variety of human or non-human viruses. The greatest challenge is expected to come in the area of virus-based therapies such as vaccines and viral vectors for gene therapy. In such cases, the therapy will need to be custom manufactured for each patient. Traditional methods for virus purification, by their nature, are prone to technician error, inefficiency or inconsistency leading to low yield and high levels of impurities. This becomes especially evident as more and more applications for purified viruses come to light. Patient-specific therapies require relatively small quantities of the therapeutic agent and such small quantities are impossible to produce efficiently with traditional large scale manufacturing techniques.

With the increased awareness and monitoring of outbreaks of novel viral pathogens, the need has arisen for more efficient, rapid and consistent viral purification methods. Conventional purification techniques typically involve manually concentrating aqueous mixtures containing virus via centrifugation or passing the mixture of virus and impurities through a size exclusion gel filtration column that separates the virus from the mixture based on size. When the virus sized particles flow through the column they can be recovered in a somewhat purified form.

Manual methods for purifying viruses have their drawbacks. For example, these methods can be labor intensive, time consuming, and are highly inefficient. Large scale manufacturing techniques typically use multiple columns which are manually packed with resin and sterilized prior to each purification run. The manual steps involved in these methods also include a high risk of contamination.

Moreover, conventional approaches and tools for viruses or virus-based products typically involve numerous manual manipulations that are subject to variations even when conducted by skilled technicians. When used at the scale needed to manufacture hundreds or thousands of different cells, cell lines and patient-specific cell based therapies, the variability, error or contamination rate may become unacceptable for commercial processes.

Small quantities of viruses and virus-based products are produced via a number of cell culture techniques. T-flasks, roller bottles, stirred bottles, or cell bags are manual methods using incubators or warm-rooms to provide environments for cell growth and viral propagation. These methods are very labor intensive, have inconsistent performance, are subject to mistakes, and difficult for large-scale production.

Another method for producing viral-based products is by embryonated chicken eggs, which requires inoculating the allantoic cavity of fertilized chicken eggs with the virus of interest, which are thereby parasitically grown and maintained. The eggs are sacrificed and the virus is collected. This method is also very labor intensive, difficult for large scale production, and objectionable because of the potential for egg-based allergic reactions and variable productivity.

Another method for producing cell-secreted products involves inoculating cells growing in a small stirred tank or bioreactor or bag-type chamber. The tank provides the environmental and metabolic needs and the viruses are allowed to accumulate. This method is costly in terms of facility support in order to accommodate a large number of unique cells and produces product at low concentration.

Another method for the production of cell-secreted products is to use a bioreactor (e.g., hollow fiber, ceramic matrix, fluidizer bed, etc.) in lieu of the stirred tank. This can bring facilities costs down and increases product concentration. The systems currently available are general purpose in nature and require considerable time from trained operators to setup, load, flush, inoculate, run, harvest, and unload. Each step typically requires manual documentation, which is labor intensive and subject to errors.

Cell culturing devices or cultureware for culturing cells in vitro are known. Hollow fiber perfusion bioreactors (HFBx) were first introduced in 1972 as a model system to study tumors growing at tissue-like densities. Since then, HFBx have been used in a variety of applications such as bioartificial organs, pharmacokinetics, cell therapy, toxicology, etc. In the mid 1980s, Biovest International (formerly Endotronics, Inc.) developed the first commercial scale HFBx system and ever since, the most common application for this technology has been the large scale production of mammalian cell-secreted proteins, predominantly monoclonal antibodies.

As disclosed in U.S. Pat. No. 4,804,628, the entirety of which is hereby incorporated by reference, a hollow fiber culture device includes a plurality of hollow fiber membranes. Medium containing oxygen, nutrients, and other chemical stimuli is transported through the lumen of the hollow fiber membranes or capillaries and diffuses through the walls thereof into an extracapillary (EC) space between the membranes and the shell of the cartridge containing the hollow fibers. The cells that are to be maintained collect in the EC space. Metabolic wastes are removed from the bioreactor. The cells or cell products can be harvested from the device.

Each unique cell or cell line must be cultured, with viruses harvested and purified separately. In order to accommodate a large number of unique cells or cell lines, a considerable number of instruments would be needed. If application of the virus or virus-based products for therapeutic purposes is intended, strict segregation of each cell production and purification process would be required. Consequently, compactness of the design and the amount of ancillary support resources required will become an important facilities issue. Moreover, the systems currently available are general purpose in nature and require considerable time from trained operators to setup, load, flush, inoculate, run, harvest and unload. Each step usually requires manual documentation.

Moreover, production tracking mandates generation of a batch record for each cell culture and purification run. Historically, this is done with a paper-based system and relies on the operator inputting the information. This is labor intensive and subject to errors.

Current purification techniques also involve cleaning and reuse of equipment, chromatography columns and filtration media. This requires Standard Operational Procedures (SOPs) to be written and the cleaning and reuse process to be validated. This is a time intensive activity.

There is a need to provide alternative methods of manufacturing vaccines that protect against diseases caused by viruses, particularly highly pathogenic viruses, such as influenza strains H5N1 and H1N1. Furthermore, there remains a need to provide methods of manufacturing large quantities of vaccines in a time period rapid enough to effectively prevent possible epidemics and/or pandemics. In addition to the conventional egg-based production methods, mammalian cell culture-based production systems, and approaches using avian cell lines, insect cells, and plant cells have been proposed.

Large scale production of live virus and recombinant viral proteins in mammalian cells usually involves growing adherent cells in standard tissue culture flasks or roller bottles and non-adherent cells in spinner cultures. These systems utilize low density cell seeding in an excess of medium, and harvesting the cells at the point of medium exhaustion. While well-understood, robust and convenient, classical batch-style two-dimensional (2-D) culture on non-porous supports or three-dimensional (3-D) suspension culture in other devices do not replicate in vivo conditions and may affect protein modifications. Thus, in addition to efficient replication of virus, the production system must possess characteristics which will provide faithful production of viral proteins, particularly antigenic glycoproteins such as influenza hemagglutinin.

Accordingly, there is a need for a system and method whereby viruses and/or virus-based products can be cultured and purified in a fully automated, rapid and sterile manner.

BRIEF SUMMARY OF THE INVENTION

One aspect of the invention concerns a method for the production of virus or virus-like particles (VLPs), comprising culturing virus-infected cells in a cell culture bioreactor having a first compartment, a second compartment, and a membrane separating the first and second compartments, wherein the cells are cultured under conditions that allow for regulating (e.g., reducing) the concentration of molecules inhibitory to virus yield or VLP yield within the compartment in which the virus-infected cells are placed (the first or second compartments), and allowing for production of the virus or VLP at a yield greater than that achieved in the absence of said regulation. The compartments of the biochamber may be arranged in any orientation that permits cell culture, production of the virus or VLP, and regulation of the inhibitory molecule. For example, depending upon the type of bioreactor, the compartments may be arranged concentrically (one compartment contained within the other) or juxtaposed (e.g., side-by-side). The terms "first" and "second" in the context of bioreactor compartments are merely designations and do not themselves connote arrangement or orientation.

In some embodiments, the bioreactor is a hollow fiber bioreactor in which the first compartment is an intracapillary (IC) space, the second compartment is an extracapillary (EC) space, the membrane is a hollow fiber membrane, the virus-infected cells are cultured in the IC space or the EC space, and the cells are cultured under conditions that allow for regulating (e.g., reducing) the concentration of molecules inhibitory to virus or VLP yield within the IC space or the EC space, and allow for production of the virus or VLP at a yield greater than that achieved in the absence of said regulation. Virus-infected cells may be cultured within the EC space or the IC space of the bioreactor. In some embodiments, virus-infected cells are cultured in the EC space and the concentration of inhibitory molecules within the EC space is regulated by increasing the flow rate of culture media on the EC side (EC circuit) of the bioreactor and controlling how fast culture media bearing the inhibitory molecules is replaced with fresh culture media on the EC side of the bioreactor.

Another aspect of the invention concerns a method for regulating the concentration of molecules inhibitory to viral or VLP yield in the biochamber compartment containing the virus-infected cells (e.g., in the EC space of a hollow fiber perfusion bioreactor), comprising culturing virus-infected cells in the compartment; and diluting one or more inhibitory molecules in the compartment by adding cell culture medium to the compartment containing the virus-infected cells or diffusing one or more inhibitory molecules from the compartment containing the virus-infected cells, through the membrane, into the other compartment. Preferably, inhibitory molecules are diluted within the bioreactor compartment containing the virus-infected cells by increasing the flow rate of culture media into the compartment of the bioreactor containing the virus-infected cells and controlling how fast culture media bearing the inhibitory molecules is replaced with fresh culture media in the compartment containing the virus-infected cells.

Another aspect of the invention concerns a hollow fiber perfusion bioreactor for production of virus, comprising semipermeable hollow fibers within a casing, wherein each of said hollow fibers comprise a lumen defining an intracapillary (IC) space, and wherein each of said hollow fibers have an exterior that, together with said casing, define an extracapillary (EC) space, and wherein at least a portion of said EC space is occupied by virus-infected cells producing virus, and wherein the virus are produced at a high rate (for example, a rate of at least 1,000 particles per cell for budding virus and at a rate of at least 10,000 particles per cell for lytic virus).

One aspect of the invention is an integrated cell culture and purification apparatus for the growth and maintenance of cells and the harvest and purification of virus products (e.g., virus and VLPs). Thus, the apparatus integrates a cell culture function with a purification function. The apparatus can be used for short production runs (e.g., less than 45 days) of a large number of unique viruses, or longer production runs. The apparatus is designed such that it can be incorporated into a production facility, and to support centralized batch information gathering. Advantageously, the apparatus's design minimizes operator time needed to setup and run the apparatus. Purification of virus product (e.g., virus and/or VLPs) is exemplified herein; however, if virus-infected cells are the product, a cell harvest unit can be used in place of the purification unit.

In the methods, apparatus, and bioreactors of the invention, harvesting can be carried out by various methods, such as batch harvest, timed batch harvest, or continuous harvest. In batch harvesting, a single harvest of the bioreactor may be initiated by the operator based on viral or VLP concentration or based on time from viral inoculation. All viral particles are collected at this time. In timed batch harvesting, the harvest is initiated by the operator based on viral or VLP concentration or based on time from viral inoculation. A predetermined volume is harvested from the bioreactor. After a defined interval, another volume is harvested. This is repeated for a predetermined number of cycles or until the operator terminates the harvesting. In continuous harvesting, the instrument harvests a given volume per unit of time (e.g., hour) continuously. The harvest could be initiated by the operator based on viral concentration or based on time from viral inoculation. Harvest continues until a time interval has passed or until the operator terminates the harvesting.

The apparatus of the invention has the capacity for a high degree of integration and automation. This reduces the amount of operator's time needed and reduces operator-induced errors. Cultureware modules (disposable portions of the cell culture unit and purification unit) are highly integrated and easy to load/unload. The control process is designed to complete sequences without the need for operator's intervention. The apparatus is modularized into a cell culture unit and purification unit. The purification unit uses the resources of the cell culture module for coordination and control. A single purification unit can support multiple cell culture units. The apparatus is designed to facilitate a central electronic records system operated in a current good manufacturing practice (CGMP) facility. Instrument support is provided for operator and consumables code identification (e.g., bar code identification, radio frequency identification (RFID) tag identification, bokode identification, or quick response (QR) code identification).

The integrated apparatus of the invention includes two units: a cell culture unit and a purification unit. Preferably, the two units are physically separate but designed to be placed together (e.g., adjacent to one another). The cell culture unit and purification unit can transfer data and coordinate activity with each other using methods known in the art for such activity, such as through a wireless communication port. The purification unit can be placed next to the cell culture unit towards the end of the production period. A line (e.g., tubing or other conduit) from each unit's cultureware connects together to provide a fluid path for the collected harvest fluid in the cell culture unit to be transferred to the purification unit. The operator initiates the purification sequence through a user interface such as a keyboard and/or touch screen interface on the cell culture unit. The end product of the apparatus is a purified product and may be neutralized in a buffered solution suitable for further processing.

The cell culture unit of the apparatus includes two individual parts: a reusable instrumentation base device (also referred to herein as a "first" reusable instrumentation base device, to distinguish it from the reusable instrumentation base device of the purification unit), and at least one disposable cell cultureware module that is used for a single production run and is disposable (also referred to herein as a "first" disposable cell cultureware module, to distinguish it from the at least one disposable cultureware of the purification unit). The instrumentation base device provides the hardware to support cell culture growth and production in a compact package, which is advantageous in a facility handling a large number of unique cell lines, for example. A pump, such as an easy-load 4 channel peristaltic pump, moves fresh basal media into the cultureware, removes spent media, adds high molecular weight factor and removes product harvest. A temperature controlled storage area (preferably, integrated) maintains the factor and harvest at a low temperature (preferably, approximately 4° C.). A heating mechanism maintains the cell environment to promote cell growth and virus production. The gas blending mechanism, in conjunction with the cultureware pH sensor controls the pH of the cell culture medium. A plurality of automated tube valving drives (e.g., two automated tube valving drives) are used to control the cultureware flowpath configuration to accomplish the fluidic functions necessary to initiate and carryout a successful run. Valves and sensors in the instrumentation base device control the fluid cycling in the cultureware. Drive for fluid circulation is provided. An identification code reader, such as a barcode reader, radio frequency identification (RFID) tag reader, bokode reader, or quick response (QR) code reader, is preferably included to facilitate operator and lot tracing. A communication port preferably ties the instrumentation device to a facilities data management system (LIMS). Preferably, the instrumentation device of the cell culture unit includes a user interface, such as a keyboard and/or flat panel display with touch screen, for user interaction.

The one-time use cultureware is provided pre-sterilized, designed for rapid loading onto the instrumentation base device ("quick-load"). The loading of the cultureware body makes connections to the instrumentation base device. The pump cassette, which is physically attached to the tubing, allows the user to quickly load the pump segments. The design and layout minimizes loading errors. The cultureware enclosure provides an area that is heated to maintain cell fluid temperature. Reservoirs to maintain fluid volumes and cycling are included in the cultureware. Sensors for fluid circulation rate and pH and thermal well for the instrument's temperature sensor are included. The blended gas from the instrumentation device is routed to the gas exchange cartridge that provides oxygen and adds or removes carbon dioxide to the circulated fluid to support cell metabolism. The cultureware module also includes a bioreactor (e.g., hollow fiber bioreactor or other bioreactor type), which provides the cell space and media component exchange for virus production. Disposable containers for harvest collection and flushing are preferably included. The operator attaches a media source, factor bag and spent media container to the cultureware before running. The media and spent media container is disconnected, pump cassette is unloaded, cultureware body is unloaded, and the used cultureware is placed in a biohazard container for disposal.

The purification unit of the apparatus includes two individual parts: a reusable instrumentation base device (also referred to herein as a "second" reusable instrumentation base device, to distinguish it from the reusable instrumentation base device of the cell culture unit), and at least one disposable cell cultureware module that is used for a single production run and is disposable (also referred to herein as a "second" disposable cell cultureware module, to distinguish it from the at least one disposable cultureware of the cell culture unit).

The instrumentation base device of the purification unit provides the hardware to extract the fluid with the virus or virus-like particle (VLP) from the cell culture unit and process it. An air detector can check the cultureware line which carries the fluid from the cell culture module to determine when fluid is available to run through the column and when no more fluid is available. Drives for a plurality of switching valves (e.g., nine switching valves) control the disposable valve portions to route fluids to complete the processes. Peristaltic pumps are used to move the fluids to accomplish the process. A fluid warmer is used before the column to minimize out gassing in the column. An optical density detector is used in the process to determine when final product should be collected. The purification unit preferably relies on the cell culture unit for user interface and communications with a facilities data management system.

As is the case with the cultureware of the cell culture unit, the cultureware of the purification unit is for one-time use.

The chromatography columns and appropriate disposable filtration media are loaded into the cultureware prior to use. The reservoirs are filled at that time with the correct buffers for the virus type. That information is preferably tied to the cultureware's identifying code (e.g., bar code, radio frequency identification (RFID) tag, barcode, or quick response (QR) code) in the facilities data management system when the operation is done and is used to verify the proper purification cultureware is loaded for the virus or VLP that is to be purified. A plurality of disposable switch valves (e.g., nine disposable switch valves) are used to prepare the cultureware and route the fluids. Easy-load peristaltic pump cassettes can be included. A flow cell for measuring optical density can be on the outlet of the column. A removable container holds the finished product (e.g., cell-derived product, such as a virus). The pump cassettes and cultureware body are unloaded from the instrumentation base device of the purification unit and placed in a biohazard container for disposal.

As an enclosed apparatus, the safety provided by complete segregation facilitates direct applicability to therapies and production of pathogenic virus and viral products. This self-contained, automated cell culture and purification apparatus allows for simultaneous culture of numerous cell cultures within a compact facility, without the need for individual, segregated cell culture suites. The integrated apparatus of the present invention provides a compact, sealed containment system that will enable the cost effective manufacture of cells, virus, and viral products, and purification of the foregoing, on an industrial scale.

The method and apparatus of the invention incorporates disposable cultureware, which eliminates the need for cleaning and reuse. The apparatus of the invention, which may be used in the method of the invention, can have the stand-alone integration of a large system in a bench top device (pumps, controls, incubator, refrigerator, cultureware, etc.). In some embodiments, the method and apparatus incorporates an identification code reader (such as a barcode reader, RFID tag reader, bokode reader or QR code reader) and data gathering software that, when used with an information management system (such as a manufacturing execution system or MIMS), allows for automating generation of the batch record.

Optionally, the apparatus includes an EC cycling unit that is advantageous over rigid reservoirs. Moreover, due to the sealed EC circuit design, without vented reservoir, the chance of cell contamination is minimized.

Optionally, the apparatus controls lactate concentration in a perfusion cell culture system using measurement of $CO_2$ and pH. This eliminates preparation, autoclaving, and the need for insertion of pH electrodes aseptically in the cultureware which requires a significant amount of time and may breach the sterile barrier of the cultureware set.

The apparatus of the present invention can incorporate features that greatly reduce the operator's time needed to support the operations (e.g., integrated pump cassette, pre-sterilized cultureware with pH sensors, quick-load cultureware) and designed automated procedures and devices which allow the apparatus to sequence through the operations (e.g., automated fluid clamps, control software).

The apparatus integrates the cell culture product (e.g., virus-infected cell, virus, or viral product) production and purification process. The design of the cultureware and instrument simplifies and reduces labor needed to produce product. This reduces sources of error in the process.

The present invention provides an automated cell culture and purification apparatus which creates a self-contained culture environment. The apparatus incorporates perfusion culture with sealed, pre-sterilized disposable cultureware, such as hollow fiber or other bioreactors, and preferably programmable process control, automated fluid valving, pH feedback control, lactic acid feedback control, temperature control, nutrient delivery control, waste removal, gas exchange mechanism, reservoirs, tubing, pumps and harvest vessels. Accordingly, the cell culture unit (such as an AutovaxID Cell Culture Module™) is capable of expanding cells in a highly controlled, contaminant-free manner, for virus production.

Any host cells useful for production of the virus of interest can be used in the methods, apparatus, systems, and bioreactors of the invention. Host cells may be human or non-human mammalian cells, insect cells, avian cells, or plant cells. For example, Madin-Darby canine kidney (MDCK) cells and African green monkey kidney (Vero) cells are useful for the production of influenza virus. Other continuous cell lines suitable as host cells for production of human vaccines include human fetal retina (Per.C6) and duck embryonic retina (AGE1.CR) cells. The host cells may be transformed or non-transformed cell lines, primary cells including somatic cells such as lymphocytes or other immune cells, chondrocytes, myocytes or myoblasts, epithelial cells and patient specific cells, primary or otherwise. Included also are cells or cell lines that have been genetically modified, such as both adult and embryonic stem cells. The automated cell culture apparatus allows for production and harvest of cells or cell-secreted protein in a manner that minimizes the need for operator intervention and minimizes the need for segregated clean rooms for the growth and manipulation of the cells. Further, the apparatus provides a culture environment that is completely self-contained and disposable. This eliminates the need for individual clean rooms typically required in a regulated, multi-use facility. Control of fluid dynamics within the bioreactor allows for growth conditions to be adjusted, e.g., changing growth factor concentrations, to facilitate application of unique culture protocols or expansion of unique cells or cell lines. As a result, there is less variation and less labor required for consistent, reproducible production of cells and viral products for applications to expansion of cells.

According to these and other aspects of the present invention, there is provided a cell culture apparatus for the production of cells and cell derived products, such as virus and viral antigens, including a reusable instrumentation base device incorporating hardware to support cell culture and viral growth. A disposable cultureware module including a cell growth chamber is removably attachable to the instrumentation base device.

According to these and other aspects of the present invention, there is also provided a method for the production of virus and viral products in a highly controlled, contaminant-free environment comprising the steps of providing a disposable cultureware module including a cell growth chamber (bioreactor), and a reusable instrumentation base device incorporating hardware to support cell culture and viral growth. The base device includes microprocessor control and a pump for circulating media through the cell growth chamber. The cultureware module is removably attached to the instrumentation base device. Cells are introduced into the cell growth chamber. A source of media (cell culture medium) is fluidly attached to (i.e., in fluid communication with) the cultureware module. Operating parameters are programmed into the microprocessor control. The pump is operated to circulate the media through the cell growth chamber to grow virus infected cells therein. The virus or VLP are harvested from the cell growth chamber. Continuous or multiple harvests can be done. The cultureware module can then be disposed of.

In a particular embodiment, the present invention provides an automated method of producing a vaccine by purifying a virus product, such as a virus or viral protein, and optionally combining the virus or viral product with a carrier molecule, such as an adjuvant, in a single formulation. In some embodiments, the virus or viral product is conjugated to the carrier molecule. Optionally, virus can be inactivated (e.g., by ultraviolet radiation or beta lactones) before or after harvest. The virus can be used for whole virus vaccines or subunit vaccines. For virus subunit vaccine production, the virus can be broken down into various ratios.

The methods, apparatus, and bioreactors of the invention are applicable for the production of virus and VLPs for research, clinical and veterinary uses. For example, the invention may be utilized for the production of human vaccines and animal (veterinary) vaccines, as well as viral vectors for nucleic acid delivery to cells in vitro or in vivo. In some embodiments, the virus is a human virus, such as human influenza virus (e.g., strains H5N1 and H1N1). The methods, apparatus, and bioreactors of the invention are particularly useful for producing large amounts of virus and VLP in small volumes of fluid (i.e., a highly concentrated product)

These and other features, aspects, and advantages of the present invention will become more apparent from the following detailed description of the preferred embodiment relative to the accompanied drawings, in which:

BRIEF DESCRIPTION OF THE DRAWINGS

FIG. 14C is a rear view of the valve body.

FIGS. 15A-15C are perspective views of a tubing slide clamp of the present invention.

FIGS. 26-31 are views of the touch screen associated with the automatic control of the cell culture unit of the present invention.

DETAILED DISCLOSURE OF THE INVENTION

Figure 33A:
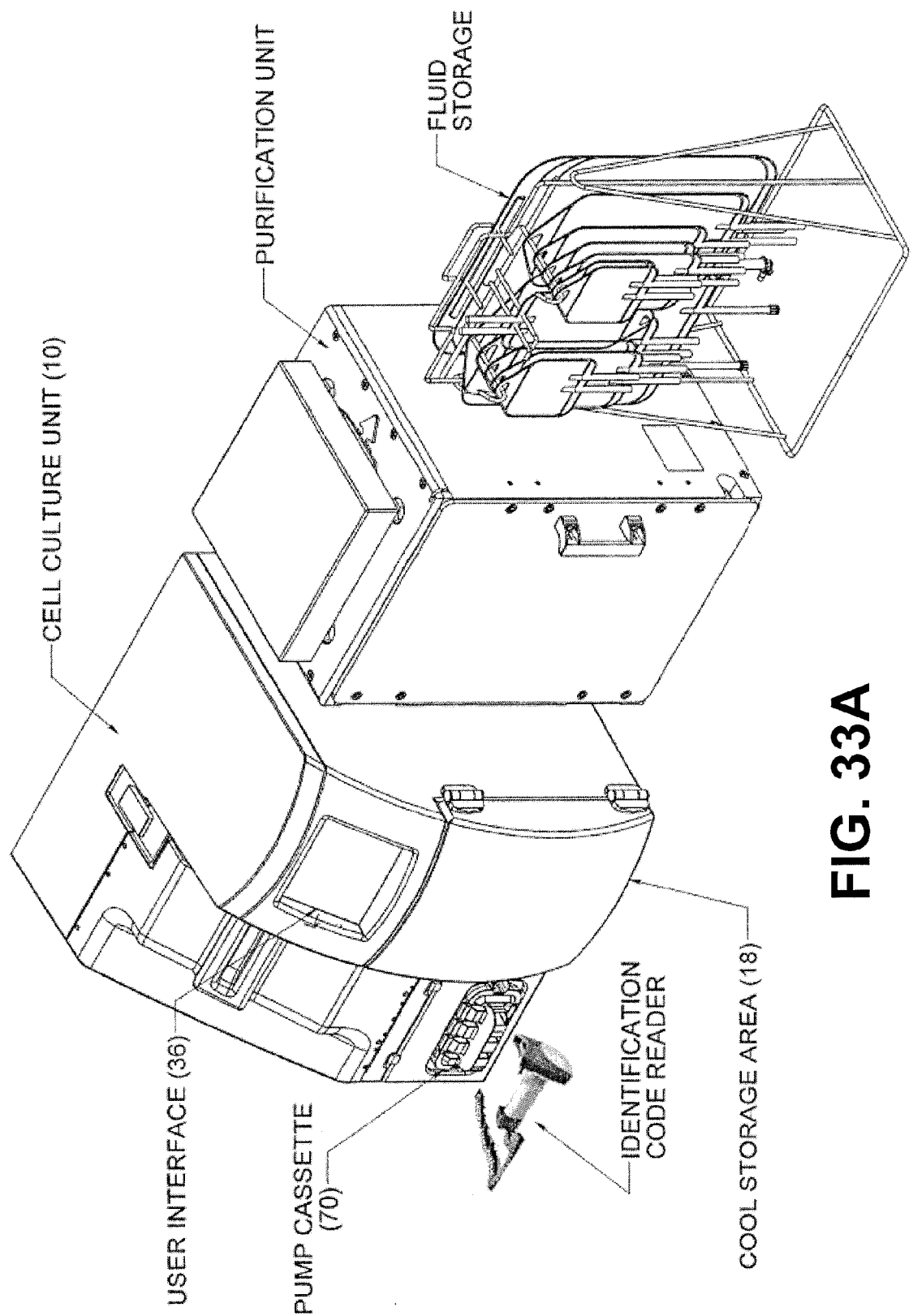
FIGS. 33A and 33B are isometric and front views of an embodiment of the integrated cell culture and virus/VLP purification apparatus of the invention, including the cell culture unit and purification unit adjacent thereto.
Figure 33B:
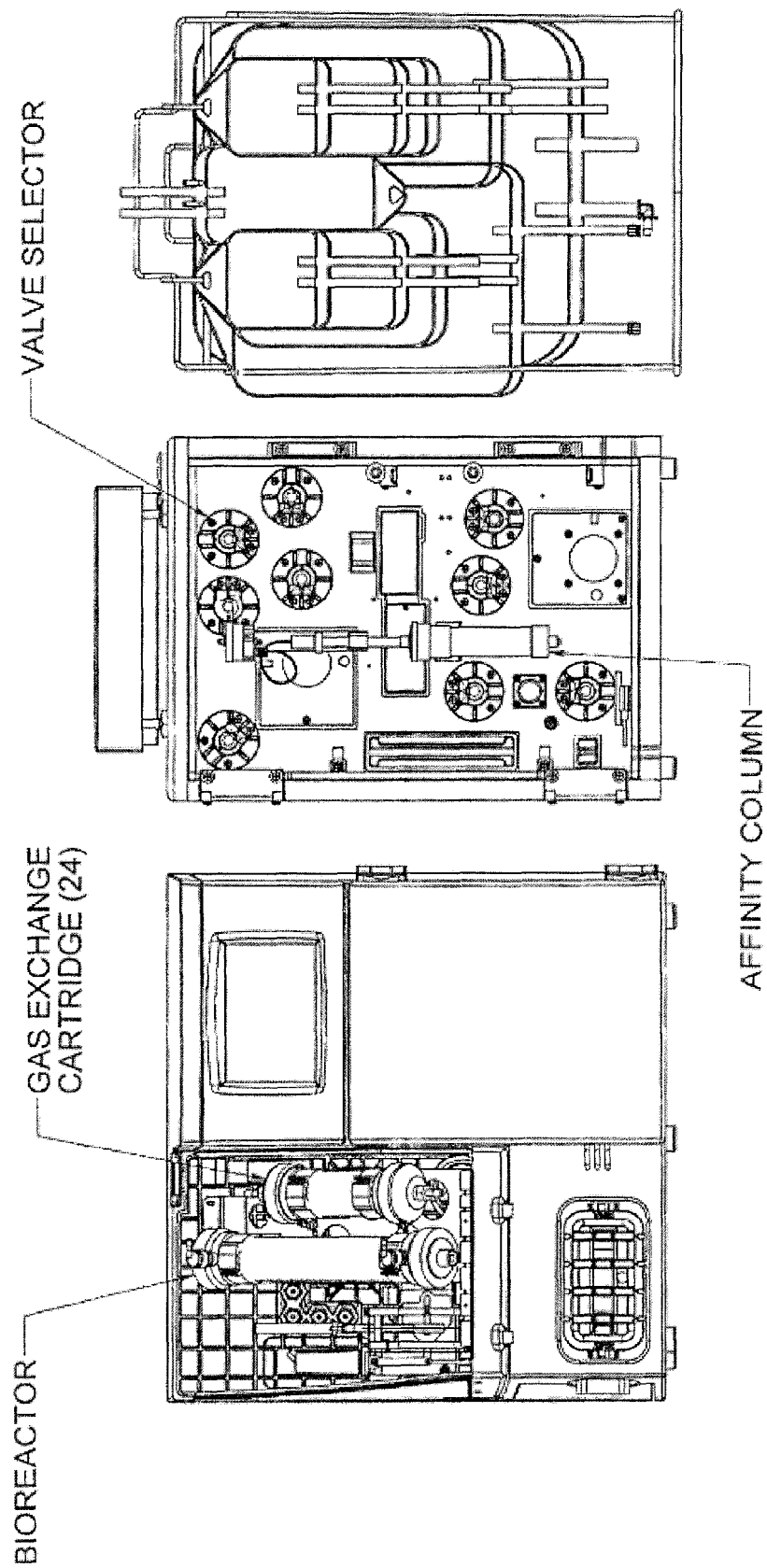

The integrated apparatus of the invention includes two units: a cell culture unit and a purification unit (FIGS. 33A and 33B). Preferably, the apparatus of the invention is modularized such that the cell culture unit and purification unit are physically separate but designed to be placed together (e.g., adjacent to one another). The cell culture unit and purification unit can transfer data and coordinate activity with each other using methods known in the art such as a communication port (e.g., a wireless communication port, desktop or laptop computer, etc.). The purification unit can be placed next to the cell culture unit toward the end of the production period, or before. A line (e.g., tubing or other conduit) from each unit's cultureware connects together to provide a fluid path for the collected harvest fluid in the cell culture unit to be transferred to the purification unit. The operator initiates the purification sequence through a user interface, such as a touch screen interface, preferably on the cell culture unit. The end product of the apparatus can be a fluid enriched or concentrated with virus product or isolated virus, suitable for further processing.

Integrating components, functions, and operations greatly reduces manpower and cost needed to produce a cell-derived product. Integrated cultureware reduces preparation and loading time. Cultureware simplification reduces the number of operator induced errors which can cause failure. Process sequencing reduces operator time needed and allows sequential operations to be automatically. Modularizing the functions into a cell culture unit and a purification unit allows higher utilization of hardware and lower costs. One purification unit can service multiple cell culture units. Utilizing the resources of the cell culture unit allows for reduced costs of the purification unit and logistically ties the two processes together. A CGMP facility is required to generate a batch record documenting the individual cell product production. The system can facilitate record generation by utilizing a central electronic records system operated in a CGMP facility.

The apparatus of the invention can be used for growth and expansion of virus-infected cells, and cell culture-based production of viruses products, e.g., production of virus, viral vaccines, viral proteins, viral vectors for gene delivery, and virus-like particles (VLPs).

DEFINITIONS

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a cultureware module" includes more than one cultureware module, reference to "an affinity column" or "a purification column" includes more than one column, and the like.

As used herein, the term "adjuvant" refers to any substance that enhances the immune-stimulating properties of an antigen.

The term "virus," is used interchangeably herein with fragment or portion of viruses (e.g., virus-like particles (VLPs)). Thus, the term "virus" is inclusive of viruses and viral particles. Any virus may potentially be produced and purified using the bioreactor, apparatus, and methods of the invention. The selection of virus is only limited by the availability of a suitable host cell for production. Virus may be lytic virus or budding virus. Virus may be enveloped or naked virus. For example, orthomyxovirus (e.g., influenza virus A, B, and C), paramyxovirus (e.g., measles, respiratory syncytial virus), arbovirus (e.g., Dengue virus), filovirus (e.g., Ebola), enterovirus (e.g., polio virus), rhinovirus, herpes virus, and hepadina virus can be produced and purified. In some embodiments, the virus is a non-human animal virus. In some embodiments, the virus is a human virus, such as human influenza virus (e.g., strains H5N1 and H1N1).

As used herein, the terms "automation" and "automated" are used interchangeably and refer to the controlled operation of an apparatus, process, or system by mechanical or electronic devices. Automated methods of the invention include sequential, pre-determined steps, which are internally controlled by software driven servo-actuators. Thus, the methods are standardized, efficient, and free of human error.

As used herein, the terms "comprising", "consisting of" and "consisting essentially of" are defined according to their standard meaning. The terms may be substituted for one another herein in order to attach the specific meaning associated with each term.

As used herein, the term "computer system" generally includes one or more computers, peripheral equipment, and software that perform data processing. A "user" or "operator" in general includes a person that utilizes the apparatus of the invention such as through a user interface. A "computer" is generally a functional unit that can perform substantial computations, including numerous arithmetic operations and logic operations without human intervention.

As used herein, "cultureware" refers to components which come in contact with the virus- or VLP-containing aqueous medium, the purified product (the purified virus or VLP), or any liquid involved in the cell culture and/or purification process. The purification cultureware (i.e., the cultureware of the purification unit) includes a pre-packed, disposable, pre-sanitized or pre-sterilized selection device, e.g., a column packed with resin, which separates the virus from the contaminants contained in the virus-containing aqueous medium. The purification cultureware can further include a pre-sanitized or pre-sterilized diafiltration module which further serves to purify the virus, as well as pre-sanitized or pre-sterilized, disposable liquid reservoirs, valves, tubing, and collection vessels.

As used herein, the terms "diafiltration module" and "tangential flow filtration cassette" are used interchangeably and generally refer to membrane-based ultrafiltration devices. The diafiltration module works on the tangential flow filtration principle whereby molecules over 0.1 micron in diameter, such as viruses (e.g., viruses such as influenza), cannot pass through the membrane but small molecules, such as buffers, host cell protein and viral fragments can pass through. The diafiltration module is used to exchange one buffer for another and is a more efficient substitute for dialysis. In one embodiment, the diafiltration module contains a membrane having about 50 cm² area and a nominal pore size of 0.1 micron.

As used herein, the terms "pre-sanitized" and "sanitized" are used interchangeably and generally refer to components that have been cleaned to reduce the presence of contaminating substances and typically packaged (to remain sanitized), before use. Components which have been pre-sanitized may also be pre-sterilized or sterile. As used herein, the term "pre-sterilized" or "sterile" are used interchangeably and generally refer to components that are free from viable contaminating organisms and typically packaged (to remain sterile), before use. Accordingly, the pre-sanitized cultureware utilized in the present invention is free of contaminants that can contaminate the culture and purification process, such contaminants can include viable microorganisms. Moreover, the method of the invention does not require the steps of sanitizing or sterilizing the cultureware to be used, since the cultureware is already or has previously been sanitized/sterilized and is ready for use.

Still further, because the cultureware is disposable, the method does not require re-sanitizing or re-sterilizing components after use. As used herein, the term "disposable" refers to components that are designed to be used and then thrown away. For example, the pre-sanitized cultureware of the present invention can be designed to be used for a single purification run and then thrown away. Accordingly, the present invention provides the advantage of eliminating the time-consuming and labor intensive steps of pre-sanitizing or pre-sterilizing and pre-assembling the cultureware used to purify the biological product (e.g., virus or VLP).

By "solid phase" is meant a non-aqueous matrix to which the ligand can adhere, such as a solid phase comprising a glass or silica surface. The solid phase may be a purification column, a discontinuous phase of discrete particles or a filter membrane. In a particular embodiment, the solid phase is a controlled pore glass column or a silicic acid column. Optionally, the solid phase is coated with a reagent (such as glycerol) which prevents nonspecific adherence of contaminants to the solid phase. Affinity ligands and methods of binding them to solid support materials are well known in the purification art. See, e.g., Affinity Separations: A Practical Approach (Practical Approach Series), Paul Matejtschuk (Editor), Irl Pr: 1997; and Affinity Chromatography, Herbert Schott, Marcel Dekker, New York: 1997.

As used herein, the terms "inhibitory molecules" in the context of molecules inhibitory to virus yield refer to biomolecules that are produced by the host cells or virus in culture, and which inhibit virus infectivity (e.g., host cell interferon), inhibit virus production (e.g., inducible cell factors), inhibit cell growth and expansion, and/or induce apoptosis of host cells (e.g., viral non-structural protein-1 (NS-1), viral ribonucleoprotein (RNP), integrins, and host cell heat shock proteins), thereby contributing to an inhibitory effect on total virus yield (see, for example, Vester D. et al., *Journal of Proteomics*, 2010, 73:1656-1669, which is incorporated by reference herein in its entirety). The inhibitory molecules may be proteins or other biomolecules produced by the virus or host cells. In some embodiments, the inhibitory molecules are host cell shut off proteins (e.g., heat shock proteins). Some inhibitory molecules induce the formation of reactive oxygen species in the host cells. Thus, in some embodiments, the inhibitory molecules are host cell stress factors, such as oxidative stress factors (see, for example, Vester D. et al., 2010). In some embodiments, the inhibitory molecules are peroxiredoxin, superoxide dismutase, or oxidoreductase. In some embodiments, the inhibitory molecules are immunostimulatory, having an immunostimulatory effect on the host cells. For example, the immunostimulatory cells may induce an interferon response (e.g., interferon-1) in the host cells. In some embodiments, the virus is human influenza virus and the inhibitory molecule comprises viral NS-1 and/or viral RNP. As described herein, various techniques can be utilized to reduce the concentration of these inhibitory molecules in the EC space wherein the host cells and virus are grown. For example, these inhibitory molecules can be selectively diluted or removed from the EC space.

EXEMPLIFIED EMBODIMENTS

Embodiment 1

A method for the production of virus and virus-like particles (VLP), comprising culturing virus-infected cells in a cell culture bioreactor comprising a first compartment, a second compartment, and a membrane separating the first and second compartments, wherein the cells are cultured in the first compartment under conditions that allow for regulating the concentration of a molecule inhibitory to virus or VLP yield from the cells within the first compartment, and allow for production of the virus or VLP at a yield greater than that achieved in the absence of said regulation.

Embodiment 2

The method of embodiment 1, wherein the bioreactor is a hollow fiber bioreactor, the first compartment is an extracapillary (EC) space, the second compartment is an intracapillary (IC) space, and the membrane comprises a hollow fiber membrane.

Embodiment 3

The method of embodiment 1, wherein the bioreactor is a hollow fiber bioreactor, the first compartment is intracapillary (IC) space, the second compartment is an extracapillary (EC) space, and the membrane comprises a hollow fiber membrane.

Embodiment 4

The method of any one of embodiments 1 to 3, wherein the inhibitory molecule is encoded by the virus.

Embodiment 5

The method of any one of embodiments 1 to 3, wherein the inhibitory molecule is a molecule produced by the virus-infected cells.

Embodiment 6

The method of any one of embodiments 1 to 3, wherein the inhibitory molecule contributes to the apoptosis of the cells before or after viral infection.

Embodiment 7

The method of any one of embodiments 1 to 3, wherein the inhibitory molecule induces an interferon response from the virus-infected cells.

Embodiment 8

The method of any one of embodiments 1 to 3, wherein the inhibitory molecule comprises an oxidative stress factor.

Embodiment 9

The method of any one of embodiments 1 to 3, wherein the inhibitory molecule comprises a plurality of inhibitory molecules.

Embodiment 10

The method of any one of embodiments 1 to 3, wherein the inhibitory molecule comprises non-structural (NS) protein, viral ribonucleoprotein (RNP), or both.

Embodiment 11

The method of any one of embodiments 1 to 3, wherein the culture conditions allow for diluting the inhibitory molecules in the cell culture medium within the first compartment.

Embodiment 12

The method of any one of embodiments 1 to 3, wherein the culture conditions allow for removal of the inhibitory molecule from the first compartment through an outlet.

Embodiment 13

The method of any one of embodiments 1 to 3, wherein said regulating comprises increasing the flow rate of culture media into the first compartment and controlling how fast culture media bearing the inhibitory molecule is replaced with fresh culture media in the first compartment.

Embodiment 14

The method of any one of embodiments 1 to 3, wherein the culture conditions allow for diffusion of the inhibitory molecule from the first compartment, through the membrane, to the second compartment of the bioreactor.

Embodiment 15

The method of any one of embodiments 1 to 3, wherein the membrane has a pore size with a molecular weight cut-off that is tailored to the inhibitory molecule(s) such that the membrane allows passage of the inhibitory molecule(s) out of the first compartment and into the second compartment.

Embodiment 16

The method of any one of embodiments 1 to 3, further comprising monitoring the concentration of the inhibitory molecule in the first compartment, or the second compartment, or both.

Embodiment 17

The method of embodiment 13, further comprising monitoring the concentration of the inhibitory molecule in the first compartment, or the second compartment, or both.

Embodiment 18

The method of any one of embodiments 1 to 3, further comprising monitoring the concentration of the inhibitory molecule in the first compartment, or the second compartment, or both; and increasing or decreasing the flow rate of culture media into the first compartment and controlling how fast culture media bearing the inhibitory molecule is replaced with fresh culture media in the first compartment based on the monitored concentration of the inhibitory molecule.

Embodiment 19

The method of any one of embodiments 1 to 3, further comprising harvesting the produced virus or VLP as a batch harvest, time-batched harvest, or continuous harvest.

Embodiment 20

The method of any one of embodiments 1 to 3, further comprising inactivating the virus before or after the virus is harvested.

Embodiment 21

The method of any one of embodiments 1 to 3, wherein said culturing comprises: infecting cells in the first compartment of the bioreactor with virus or placing virus-infected cells in the first compartment of the bioreactor; and culturing the virus-infected cells under conditions that allow for removal of the inhibitory molecule from the first compartment of the bioreactor, and for production of virus or VLP at a rate greater than that in the absence of said removal.

Embodiment 22

The method of any one of embodiments 1 to 3, further comprising adjusting the reduction of inhibitory molecule in the first compartment in response to viral or VLP yield, infectivity of harvested virus or VLP, or apoptosis of cells in the first compartment.

Embodiment 23

The method of embodiment 2 or 3, wherein the hollow fiber bioreactor is in a cell culture unit comprising: a reusable instrumentation base device incorporating hardware to support cell culture growth; and at least one disposable cell cultureware module removably attachable to the instrumentation base device, wherein the first cultureware module comprises the hollow fiber bioreactor.

Embodiment 24

The method of embodiment 23, wherein the cell culture unit is a cell culture unit of an automated cell culture and purification apparatus for the production of virus and VLP, wherein the cell culture unit further comprises a purification unit linked to the cell culture unit, wherein the purification unit comprises a second reusable instrumentation base device incorporating hardware to receive fluid from the cell growth chamber of the cell culture unit; and at least one second disposable cell cultureware module removably attachable to the second instrumentation base device of the purification unit, and wherein the second cultureware module includes a selection device for purification of the produced virus or VLP.

Embodiment 25

The method of embodiment 23, wherein the method is automated.

Embodiment 26

The method of any one of embodiments 1 to 3, wherein the method is automated.

Embodiment 27

The method of any one of embodiments 1 to 3, wherein the virus is influenza A, B or C.

Embodiment 28

The method of embodiment 27, wherein the virus is influenza A strain H5N1 or H1N1.

Embodiment 29

The method of any one of embodiments 1 to 3, wherein the virus is an orthomyxovirus, paramyxovirus, arbovirus, filovirus, enterovirus, rhinovirus, herpes virus, or hepadina virus.

Embodiment 30

The method of any one of embodiments 1 to 3, further comprising combining the produced virus with a pharmaceutically acceptable carrier to produce a vaccine.

Embodiment 31

The method of any one of embodiments 1 to 3, further comprising using the produced virus or VLP to produce a live whole virus vaccine, a killed whole virus vaccine, a recombinant virus vaccine, or a subunit vaccine.

Embodiment 32

The method of any one of embodiments 1 to 3, wherein the virus is a recombinant virus.

Embodiment 33

The method of any one of embodiments 1 to 3, wherein the virus is a wild-type virus.

Embodiment 34

The method of any one of embodiments 1 to 3, further comprising purifying the produced virus or VLP.

Embodiment 35

The method of any one of embodiments 1 to 3, wherein the virus-infected cells are mammalian cells, mammalian cells, insect cells, avian cells, or plant cells.

Embodiment 36

The method of any one of embodiments 1 to 3, wherein the virus is influenza A, and wherein the virus-infected cells are selected from among Madin-Darby canine kidney (MDCK) cells, African green monkey kidney (Vero) cells, human fetal retina (Per.C6) cells, and duck embryonic retina (AGE1.CR) cells.

Embodiment 37

The method of any one of embodiments 1 to 3, further comprising maintaining, with a heating mechanism, the temperature of the bioreactor at a temperature (a discrete temperature or a temperature range) that is conducive to peak viral replication.

Embodiment 38

The method of embodiment 37, wherein the virus is wild-type influenza virus and the temperature is 37 degrees C.-39 degrees C., wherein the virus is a cold-adapted strain of influenza virus and the temperature is 32 degrees C.-34 degrees C., or wherein the virus is rhinovirus, and the temperature is 33 degrees C.-35 degrees C.

Embodiment 39

A method for regulating the concentration of a molecule inhibitory to viral yield or virus-like particle (VLP) yield in a first compartment of a bioreactor comprising the first compartment, a second compartment, and a membrane separating the first and second compartments, said method comprising the culturing virus-infected cells in the first compartment by adding cell culture medium to the first compartment and controlling how rapidly culture medium bearing the inhibitor molecule is replaced with fresh culture medium in the first compartment, or by diffusing one or more inhibitor molecules from the first compartment, through the membrane, into the second compartment.

Embodiment 40

The method of embodiment 39, wherein the bioreactor is a hollow-fiber bioreactor; the membrane is a hollow-fiber membrane; and the first compartment is an extracapillary (EC) space and the second compartment is an intracapillary (IC) space, or vice-versa.

Embodiment 41

The method of embodiment 39 or 40, wherein the method is automated.

Embodiment 42

The method of embodiment 39 or 40, wherein the virus is influenza A, B or C.

Embodiment 43

The method of embodiment 42, wherein the virus is influenza A strain H5N1 or H1N1.

Embodiment 44

The method of embodiment 39, wherein the virus is an orthomyxovirus, paramyxovirus, arbovirus, Filovirus, enterovirus, rhinovirus, herpes virus, or hepadina virus.

Embodiment 45

The method of embodiment 39, wherein the virus-infected cells produce virus, and wherein said method further comprises combining the produced virus with a pharmaceutically acceptable carrier to produce a vaccine.

Embodiment 46

The method of embodiment 39, further comprising using the produced virus or VLP to produce a live whole virus vaccine, a killed whole virus vaccine, a recombinant virus vaccine, or a subunit vaccine.

Embodiment 47

The method of embodiment 39, further comprising purifying the produced virus or VLP.

Embodiment 48

The method of embodiment 39, wherein the virus-infected cells are mammalian cells, mammalian cells, insect cells, avian cells, or plant cells.

Embodiment 49

The method of embodiment 39, wherein the virus is influenza A, and wherein the virus-infected cells are selected from among Madin-Darby canine kidney (MDCK) cells, African green monkey kidney (Vero) cells, human fetal retina (Per.C6) cells, and duck embryonic retina (AGE1.CR) cells.

Embodiment 50

The method of embodiment 39, wherein the virus is a recombinant virus.

Embodiment 51

The method of embodiment 39, wherein the virus is a wild-type virus.

Embodiment 52

The method of embodiment 39, further comprising maintaining, with a heating mechanism, the temperature of the cell growth chamber at a temperature that is conducive to peak viral replication.

Embodiment 53

The method of embodiment 52, wherein the virus is wild-type influenza virus and the temperature is 37 degrees C.-39 degrees C., wherein the virus is a cold-adapted strain of influenza virus and the temperature is 32 degrees C.-34 degrees C., or wherein the virus is rhinovirus, and the temperature is 33 degrees C.-35 degrees C.

Embodiment 54

A hollow fiber perfusion bioreactor for production of virus or virus-like particles (VLP), comprising semipermeable hollow fibers within a casing, wherein each of said hollow fibers comprise a lumen defining an intracapillary (IC) space, and wherein each of said hollow fibers have an exterior that, together with said casing, define an extracapillary (EC) space, and wherein at least a portion of said EC space or IC space is occupied by virus-infected cells producing virus or VLP.

Embodiment 55

An automated cell culture and purification apparatus for the production of virus and virus-like particles (VLPs), comprising:
(a) a cell culture unit comprising:
  a first reusable instrumentation base device incorporating hardware to support cell culture growth; and
  at least one first disposable cell cultureware module removably attachable to said first instrumentation base device, said first cultureware module including a cell growth chamber; and
(b) a purification unit linked to said cell culture unit, said purification unit comprising:
  a second reusable instrumentation base device incorporating hardware to receive fluid from said cell growth chamber of said cell culture unit; and
  at least one second disposable cell cultureware module removably attachable to said second instrumentation base device of said purification unit, said second cultureware module including a selection device.

Embodiment 56

The cell culture and purification apparatus of embodiment 55, wherein said first instrumentation device of said cell culture unit includes a heating mechanism for heating the cell growth chamber to promote growth and production.

Embodiment 57

The cell culture and purification apparatus of embodiment 56, wherein said at least one first cultureware module of said cell culture unit includes an inlet and outlet port, said inlet and outlet ports being constructed and arranged to align with air ports of said instrument device of said cell culture unit such that the heat exchange mechanism forces heated air into said at least one first cultureware module from said first instrument device of said cell culture unit.

Embodiment 58

The cell culture and purification apparatus of embodiment 56 or 57, wherein the heating mechanism maintains the temperature of the cell growth chamber at a temperature (a discrete temperature or a temperature range) that is conducive to peak viral replication.

Embodiment 59

The cell culture and purification apparatus of embodiment 58, wherein the virus is wild-type influenza virus and the temperature is 37 degrees C.-39 degrees C., wherein the virus is a cold-adapted strain of influenza virus and the temperature is 32 degrees C.-34 degrees C., or wherein the virus is rhinovirus, and the temperature is 33 degrees C.-35 degrees C.

Embodiment 60

The cell culture and purification apparatus of embodiment 55, wherein the cell growth chamber comprises a bioreactor that provides cell space and medium component exchange.

Embodiment 61

The cell culture and purification apparatus of embodiment 60, wherein the cell growth chamber comprises a hollow fiber bioreactor comprising an intracapillary (IC) space and an extracapillary (EC) space.

Embodiment 62

The cell culture and purification apparatus of embodiment 61, wherein said at least one first cultureware module of said cell culture unit includes at least one sensor for sensing the concentration of one or more molecules within the EC space that are inhibitory to viral yield.

Embodiment 63

The cell culture and purification apparatus of embodiment 62, wherein the one or more molecules that are inhibitory to viral yield comprise viral non-structural (NS) protein or viral ribonucleoprotein.

Embodiment 64

The cell culture and purification apparatus of embodiment 55, wherein said selection device comprises an ion exchange device (anion or cation exchange device), immuno-affinity chromatography device, affinity chromatography device, ionic exchange chromatography device, hydrophobic interaction chromatography device, or size exclusion chromatography device.

Embodiment 65

The cell culture and purification apparatus of embodiment 55, wherein said selection device comprises an ion exchange device having a charged particle (matrix) that binds reversibly to the virus (e.g., a Sartorious Q75 anion exchange filter), a column packed with a hydrophobic absorbent, such as cellulose, cross-linked dextrose (Sephadex), or a column containing cross-linked polystyrene with pores of varying sizes.

Embodiment 66

The cell culture and purification apparatus of embodiment 55, wherein said selection device comprises a chromatography resin or filter.

Embodiment 67

The cell culture and purification apparatus of embodiment 66, wherein the chromatography resin or filter comprises natural or artificial hydroxyapatite.

Embodiment 68

The cell culture and purification apparatus of embodiment 67, wherein the chromatography resin or filter comprises ceramic hydroxyapatite.

Embodiment 69

The cell culture and purification apparatus of embodiment 55, wherein said second disposable cultureware module further comprises: multiple, liquid reservoirs, a device for flowing liquid from the reservoirs and into the selection device, a device for diverting the effluent from the selection device, and a container for collecting effluent from the selection device.

Embodiment 70

The cell culture and purification apparatus of embodiment 69, wherein the device for flowing liquid into the selection device comprises a series of pre-sterilized, disposable valves and tubing which connect the reservoirs to the selection device and which allow liquid from only one reservoir at a time to pass through the selection device.

Embodiment 71

The cell culture and purification apparatus of embodiment 69 or 70, wherein the device for flowing liquid into the selection device comprises a series of pre-sterilized, disposable valves and tubing which connect the reservoirs to the selection device and which allow liquid from more than one reservoir at a time to pass through the selection device.

Embodiment 72

The cell culture and purification apparatus of embodiment 55, wherein said second cultureware module of said purification unit further comprises a device for diafiltering the purified product.

Embodiment 73

An automated method for the production of virus and virus-like products (VLP) and purification thereof in a contaminant-free environment, comprising the steps of:
  providing at least one first disposable cultureware module, said first module including a cell growth chamber;
  providing a first reusable instrumentation base device incorporating hardware to support cell culture growth, said base device including a microprocessor control and a pump for circulating cell culture medium through the cell growth chamber;
  providing at least one second disposable cultureware module, said second cultureware module including a selection device (such as a purification column);
  providing a second reusable instrumentation base device incorporating hardware to receive fluid from the cell growth chamber;
  removably attaching said at least one first cultureware module to said first instrumentation base device;
  introducing cells into the cell growth chamber;
  fluidly attaching a source of cell culture medium to said at least one first cultureware module;
  programming operating parameters into the microprocessor control;
  operating the pump to circulate the cell culture medium through the cell growth chamber to grow virus-infected cells therein;
  loading the culture medium containing the virus or VLPs onto the selection device to absorb a virus or VLP onto the selection device;

eluting the absorbed virus or VLP into an aqueous medium; and collecting the virus or VLP in a pre-sterilized collection vessel to form a purified product.

Embodiment 74

The method of embodiment 73, further comprising regulating the concentration of molecules inhibitory to virus or VLP yield within the cell growth chamber.

Embodiment 75

The method of embodiment 74, wherein the step of regulating the concentration of inhibitory molecules within the cell growth chamber comprises diluting the inhibitory molecule within the cell growth chamber.

Embodiment 76

The method of embodiment 75, wherein said diluting is achieved by adding (e.g., pumping) cell culture medium to the cell growth chamber.

Embodiment 77

The method of embodiment 75, wherein the cell growth chamber comprises a hollow fiber bioreactor comprising an extracapillary (EC) space and an intracapillary (IC) space, and wherein said diluting is achieved by adding (e.g., pumping) cell culture medium into the EC space, and removing the inhibitory molecule through an EC space outlet.

Embodiment 78

The method of embodiment 74, wherein the cell growth chamber comprises a hollow fiber bioreactor comprising an extracapillary (EC) space, an intracapillary (IC) space, and a hollow fiber membrane, and wherein said regulating comprises diffusing the inhibitory molecule from the EC space, through the hollow fiber membrane, to the IC space of the bioreactor.

Embodiment 79

The method of embodiment 73, further comprising the step of heating the at least one first cultureware module with a heating mechanism to promote cell growth and viral replication.

Embodiment 80

The method of embodiment 73, further comprising the step of transferring the product into an acidic solution.

Embodiment 81

The method of embodiment 80, wherein the transfer is achieved by diafiltration.

Embodiment 82

The method of embodiment 81, further comprising the step of transferring the product to a final buffer solution.

Embodiment 83

The method of embodiment 82, wherein the transfer is achieved by diafiltration.

Embodiment 84

The method of embodiment 73, further comprising the step of washing the selection device with at least one solution prior to loading the medium containing the virus or VLP.

Embodiment 85

The method of embodiment 73, further comprising the step of washing the selection device with at least one solution prior to eluting the product.

Embodiment 86

The method of embodiment 85, wherein the at least one solution comprises PBS, glycine, and/or citrate.

Embodiment 87

The method of embodiment 73, further comprising the step of warming and/or degassing the medium prior to loading the medium onto the selection device.

Embodiment 88

The method of embodiment 73, wherein the step of eluting the product comprises the use of a solution containing glycine or citrate or saline.

Embodiment 89

The method of embodiment 73, wherein the step of eluting the product comprises the use of a photometer.

Embodiment 90

The method of embodiment 82, wherein the step of transferring the product to a final buffer solution comprises the use of solution containing buffered saline.

Embodiment 91

The method of embodiment 83, further comprising the step of filtering the product contained in the final buffer solution prior to collecting the product in a pre-sterilized, disposable collection vessel.

Embodiment 92

The method of embodiment 73, wherein the selection device comprises an ion exchange device, immuno-affinity chromatography device, affinity chromatography device, ionic exchange chromatography device, hydrophobic interaction chromatography device, or size exclusion chromatography device.

Embodiment 93

The method of embodiment 73, wherein the selection device comprises an ion exchange device having a charged particle (matrix) that binds reversibly to the virus (e.g., a Sartorious Q75 anion exchange filter), a column packed with a hydrophobic absorbent, such as cellulose, cross-linked dextrose (Sephadex), or a column containing cross-linked polystyrene with pores of varying sizes.

Embodiment 94

The method of embodiment 73, wherein the selection device comprises a chromatography resin or filter.

Embodiment 95

The method of embodiment 94, wherein the chromatography resin or filter comprises natural or artificial hydroxyapatite.

Embodiment 96

The method of embodiment 94, wherein the chromatography resin or filter comprises ceramic hydroxyapatite.

Embodiment 97

The method of embodiment 73, wherein the product is a virus.

Embodiment 98

The method of embodiment 73, wherein the product is VLP.

Embodiment 99

The method of embodiment 97 or 98, wherein the virus is influenza A, B or C.

Embodiment 100

The method of embodiment 99, wherein the virus is influenza A strain H5N1 or H1N1.

Embodiment 101

The method of embodiment 97 or 98, wherein the virus is an orthomyxovirus, paramyxovirus, arbovirus, Filovirus, enterovirus, rhinovirus, herpes virus, or hepadina virus.

Embodiment 102

An automated method for producing an immunogenic composition such as a vaccine, comprising purifying a virus or virus-like particle (VLP) from a virus-containing fluid medium using the method according to embodiment 73; and combining the virus or VLP with a pharmaceutically acceptable carrier.

Embodiment 103

The automated method of embodiment 102, further comprising combining the virus or VLP with a carrier molecule and/or adjuvant within the same formulation.

Embodiment 104

The automated method of embodiment 103, wherein said combining comprises conjugating the virus or VLP with the carrier molecule and/or adjuvant.

Embodiment 105

The automated method of embodiment 103, wherein the carrier molecule and/or adjuvant are unconjugated with the virus or VLP.

Cell Culture Unit

The cell culture unit of the integrated apparatus includes two individual parts: a reusable instrumentation base device (also referred to herein as a "first" reusable instrumentation base device, to distinguish it from the reusable instrumentation base device of the purification unit), and at least one disposable cell cultureware module that is used for a single production run and is disposable (also referred to herein as a "first" disposable cell cultureware module, to distinguish it from the at least one disposable cultureware of the purification unit). The instrumentation base device provides the hardware to support cell culture growth and production in a compact package, which is advantageous in a facility handling a large number of unique cell lines, for example. A pump, such as an easy-load 4 channel peristaltic pump, moves fresh basal media into the cultureware, removes spent media, adds high molecular weight factor and removes product harvest. A temperature controlled storage area (preferably, integrated) maintains the factor and harvest at a low temperature (preferably, approximately 4° C.). A heating mechanism maintains the cell environment to promote growth and production. The gas blending mechanism, in conjunction with the cultureware pH sensor controls the pH of the cell culture medium. A plurality of automated tube valving drives (e.g., two automated tube valving drives) are used to control the cultureware flowpath configuration to accomplish the fluidic functions necessary to initiate and carryout a successful run. Valves and sensors in the instrumentation base device control the fluid cycling in the cultureware. Drive for fluid circulation is provided. An identification code reader (such as a barcode reader, radio frequency identification (RFID) tag reader, bokode reader, or quick response (QR) code reader) is preferably included to facilitate operator and lot tracing. A communication port preferably ties the instrumentation device to a facilities data management system (LIMS). Preferably, the instrumentation device of the cell culture unit includes a user interface, such as a flat panel display with touch screen, for user interaction.

The one-time use cultureware is provided pre-sterilized, designed for rapid loading onto the instrumentation base device ("quick-load"). The loading of the cultureware body makes connections to the instrumentation base device. The pump cassette, which is physically attached to the tubing, allows the user to quickly load the pump segments. The design and layout minimizes loading errors. The cultureware enclosure provides an area that is heated to maintain cell fluid temperature. Reservoirs to maintain fluid volumes and cycling are included in the cultureware. Sensors for fluid circulation rate and pH and thermal well for the instrument's temperature sensor are included. The blended gas from the instrumentation device is routed to the gas exchange cartridge that provides oxygen and adds or removes carbon dioxide to the circulated fluid to support cell metabolism. The cultureware module also includes a bioreactor (e.g., hollow fiber bioreactor or other bioreactor type), which provides the cell space and media component exchange. Disposable containers for harvest collection and flushing are provided. The operator attaches a media source, factor bag and spent media container to the cultureware before running. The media and spent media container is disconnected, pump cassette is unloaded, cultureware body is unloaded and the used cultureware is placed in a biohazard container for disposal.

Figure 1:
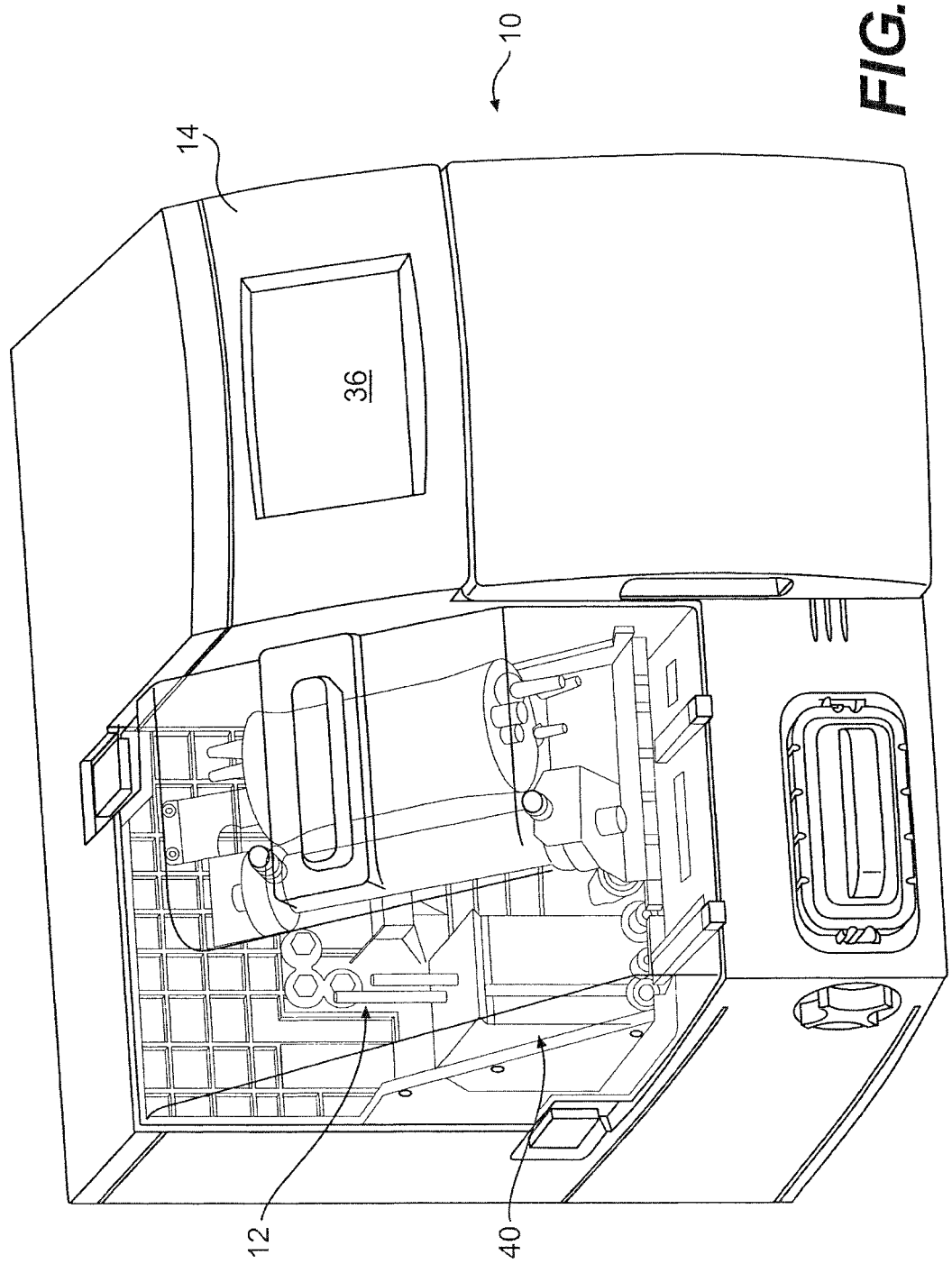
FIG. 1 is a perspective view of the cell culture unit for producing cells and/or cell derived products according to the present invention.

Referring to FIG. 1, the present invention provides a fully integrated cell culture unit 10 for producing cells and cell derived products in a closed, self-sufficient environment. More specifically, the cell culture unit allows for cell expansion and harvest of cells and their products with minimal need for technician interaction. As will be described further herein, the device incorporates cell culture technology, for example, hollow fiber or similar bioreactor perfusion technology, with all tubing components, harvest tubing and tubes threaded through the pump cassette, encased in a single-use, disposable incubator 12. Following bioreactor inoculation with cells, the cell culture unit follows pre-programmed processes to deliver media, maintain pH, maintain lactate levels, control temperature and harvest cells or cell-secreted protein. Standard or unique cell culture growth parameters can be programmed such that various cell types can be expanded and such that virus or VLP can be harvested in an efficient, reproducible manner with minimal chance of human error. The cell culture system and method described in International Publication No. WO 2007/139742, "Method and System for the Production of Cells and Cell Products and Applications Thereof" (Wojciechowski R. et al.), is hereby incorporated by reference in its entirety.

The cell culture unit is based on cell growth chamber technology. For example, bioreactors that have a plurality of semi-permeable hollow fibers or other type of semi-permeable membrane or substrate potted (attached) in a housing to create a space inside the fiber or one side of the membrane (referred to as intracapillary (IC) space) separate from that outside the fibers or on the other side of the membrane (referred to as extracapillary (EC) space). Fluid distribution between the IC space and EC space occurs through the fiber pores which can range in size from 10 MW (Kd) to 0.2 μm. Cells are placed on one side of the fiber or membrane, usually in the EC space, in a complete cell culture medium, which is usually the same medium used to expand cells prior to bioreactor inoculation (serum containing, serum-free, or protein-free medium). Cells are usually placed in the EC space when secreted protein is the desired product. In some instances, when cells are the desired product, it may be beneficial to place cells in the IC space.

Medium is perfused through a bioreactor 20 by circulating through the IC space at a fast rate. The medium can be a liquid containing a well defined mixture of salts, amino acids, and vitamins that often contain one or more protein growth factors. This serves to deliver nutrients to the cell space and conversely, removes or prevents a toxic build-up of metabolic waste. During this circulation, medium is passed through an oxygenator or gas exchanger cartridge 24 which serves to provide pH control and oxygen for the cells and conversely, remove carbon dioxide from the culture. When the bioreactor 20 contains a smaller number of cells, just after inoculation, the oxygenator or gas exchange cartridge is used to provide $CO_2$ and subsequently control pH of the culture environment. As cell number increases, the oxygenator is used to remove $CO_2$ which serves to enhance acid neutralization and control the pH of the culture. Other bioreactor configurations, in addition to hollow fibers, that are designed and optimized for the growth and production of cells and production of cell-derived products may also be used.

The cell culture unit 10 provides significant efficiencies and cost reduction through its disposable component and enclosed operation. As such, cell lines are contained in a closed system and continuously cultured without the need for specialized, segregated clean rooms. This fully integrated apparatus eliminates the need for cleaning and sterilization validations, as well as the need for hard plumbing associated with conventional cell culture facilities.

Figure 2:
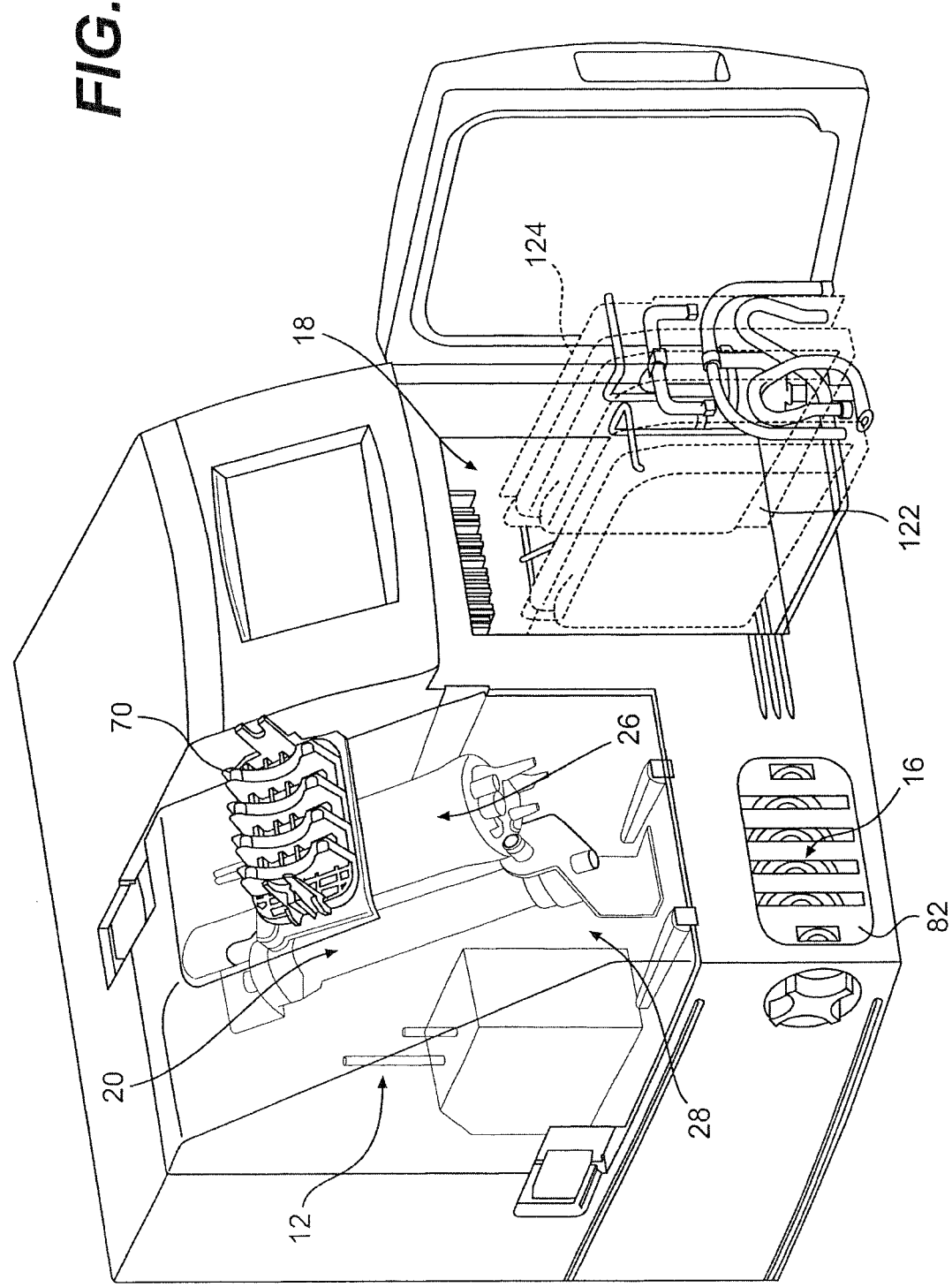
FIG. 2 is another perspective view of the cell culture unit of the present invention, with the cold storage area opened.
Figure 5:
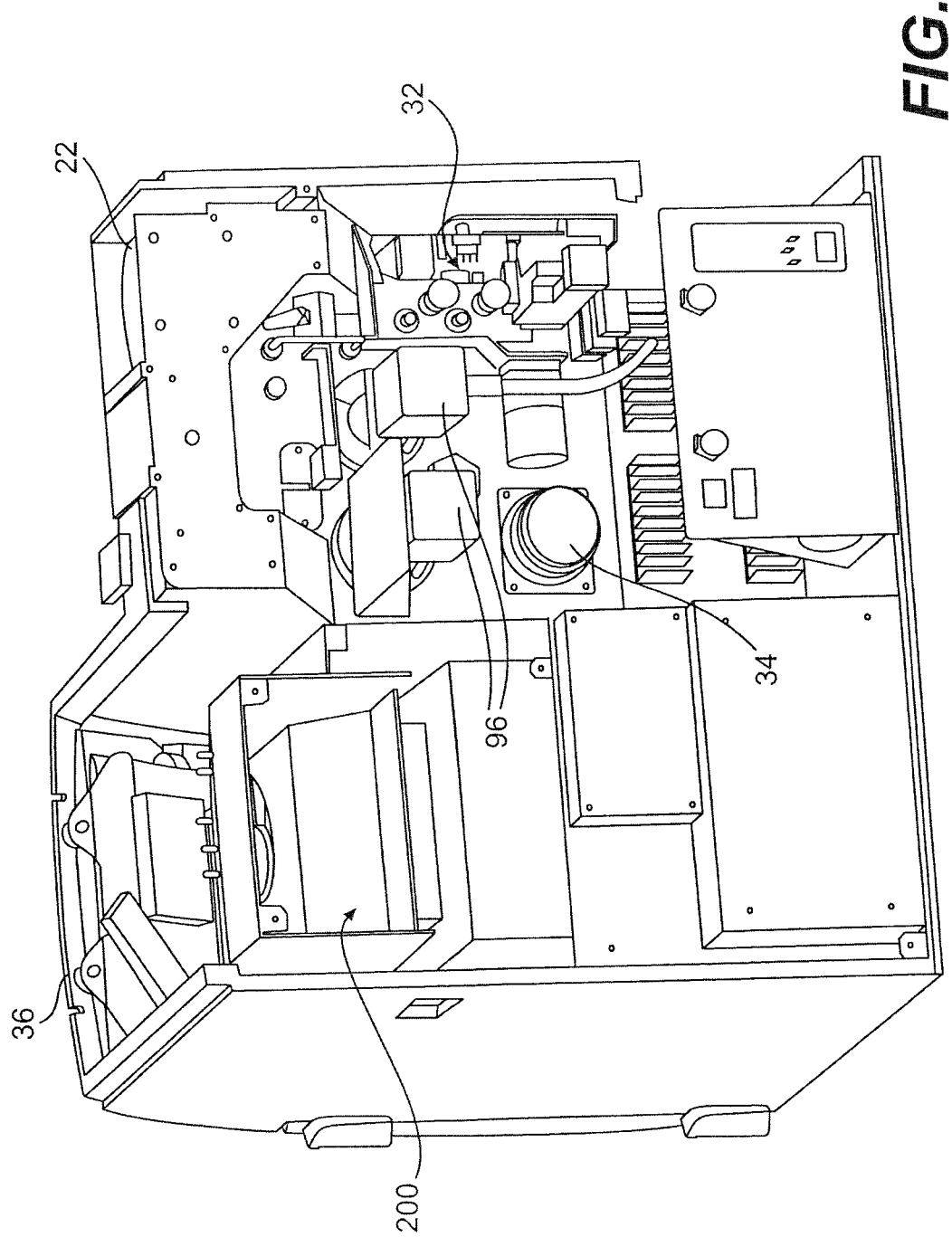
FIG. 5 is a rear view of the instrumentation device of the cell culture unit of FIG. 3, with covers removed.
Figure 6:
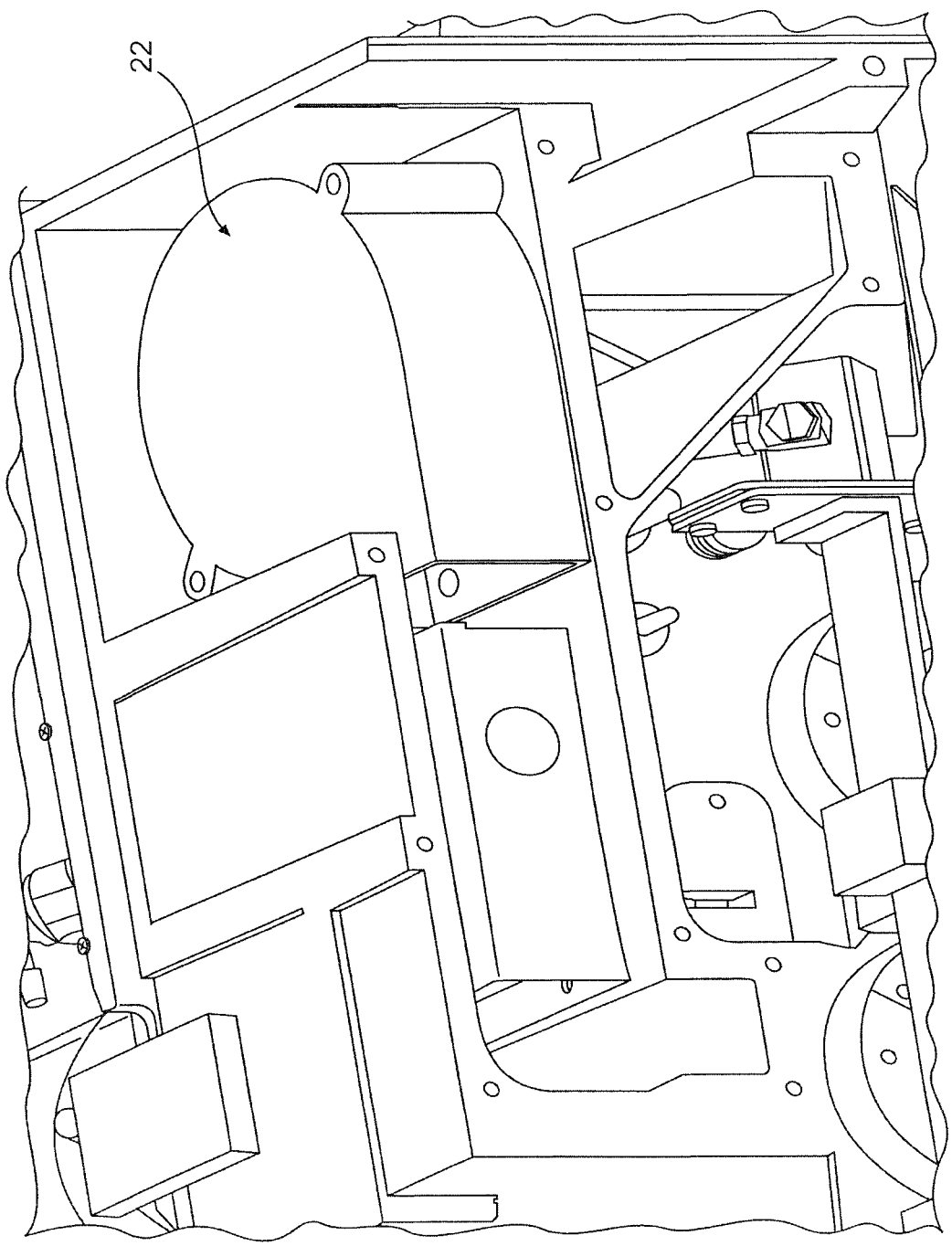
FIG. 6 is an enlarged view of the heating system of the instrumentation device of the cell culture unit of FIG. 3.

Referring again to FIG. 1, the cell culture unit includes two individual parts: an instrumentation base device 14 that is reusable and an enclosed cultureware module 12 that is used for a single production run and is disposable. Numerous modules 12 can be used on a single device 14. The instrument provides the hardware to support cell culture growth and production in a compact package. As shown in FIG. 2, and as will be described in further detail herein, an easy-load multiple channel peristaltic pump drive 16 located in base device 14 and a pump cassette 70 move fresh basal media into the cultureware, removes spent media, adds growth factors or other supplements and removes product harvest. An integrated temperature controlled storage area 18 maintains the factor and harvest at a low temperature (approximately 4° C.). An integrated heating mechanism 22 (FIG. 6) maintains the cell environment to promote growth and production. A gas exchange cartridge 24 (FIG. 5), in conjunction with a cultureware pH sensor 26 controls the pH of the cell culture medium. Two automated tube valving drives 90 (FIG. 3) are used to control the cultureware flow path configuration to accomplish the fluidic switching functions needed to initiate and do a successful run. Valves 90 and sensors 32 (FIGS. 3, 5, 13) in the instrument control the fluid cycling in the cultureware module 12. A pump drive 34 (FIGS. 3, 5) for fluid circulation is provided. A wireless or tethered (attached) identification code reader (such as a barcode reader, radio frequency identification (RFID) tag reader, or quick response (QR) code reader), shown in FIG. 33A, facilitates operator and lot tracing. An identification code comprises an identifier on or made part of a surface such as cultureware module or user identification tag, and which may include, but is not limited to, a bar code, a radio frequency identification tag, a number, a series of numbers, a color, a series of colors, a letter, a series of letters, a symbol, a series of symbols, and a combination of one or more of the foregoing. A communication port ties the instrument to a data information management system (such as a MES). A user interface 36, such as a keyboard and/or flat panel display (shown in FIGS. 1 and 33) with touch screen capability, is available for user interaction.

The one-time use cultureware module 12 of the cell culture unit is provided pre-sterilized. It is designed for quick loading onto the instrument ("quick-load"), as will be described further herein. The loading of the cultureware body makes connections to the instrument. Pump cassette 70 (FIG. 2), which is physically attached to the tubing, allows the user to quickly load the pump segments. This design and layout minimizes loading errors. The cultureware enclosure 12 provides an area that is heated to maintain cell fluid temperature. A fluid cycling unit 40 (FIGS. 1, 18) maintains fluid volumes and cycling and is included in the cultureware. Sensors for fluid circulation rate, pH and a thermal well for the instrument's temperature sensor are provided. The blended gas from the instrument is routed to gas exchange cartridge 24 that provides oxygen and adds or removes carbon dioxide to the circulated fluid to support cell metabolism. A magnetically coupled pump drive 34 (FIGS. 11-12) circulates fluid thru the bioreactor 20 and gas exchange cartridge 24. The bioreactor 20 that provides the cell space and media component exchange is also in the cultureware. Disposable containers for harvest collection are provided. Prior to the beginning of the culture, the operator (also referred to herein as the user) attaches a media source, factor bag and spent media container to the cultureware before running. At the conclusion of the run the harvest containers are removed or drained, media and spent media container is disconnected, pump cassette is unloaded, cultureware body is unloaded and the used cultureware can be placed in a biohazard container for disposal.

Cell expansion and subsequent process tracking can be facilitated by generation of a batch record for each culture. Historically, this is done with a paper-based system that relies on operator input of the information. This is labor intensive and subject to errors. The fully integrated apparatus of the invention can incorporate an identification code reader (such as a barcode reader, radio frequency identification (RFID) tag reader, bokode reader, or quick response (QR) code reader), and data gathering software which, when used with the information management system (MES), allows for automatic generation of the batch record.

The apparatus of the present invention has application in a regulated cell culture environment. It is anticipated that the production of viral vaccines may require the simultaneous culture of numerous cell lines in a single facility. In addition to the segregation created through this closed culture approach, the apparatus is designed to support a standard information management system (such as a LIMS or MES) protocol. This capability contributes to the creation of thorough batch records and verification of culture conditions to ensure standardization, tracking and safety of each product. This capability facilitates the multi-product concept that is pivotal to facilities involved with infectious products.

Figure 10:
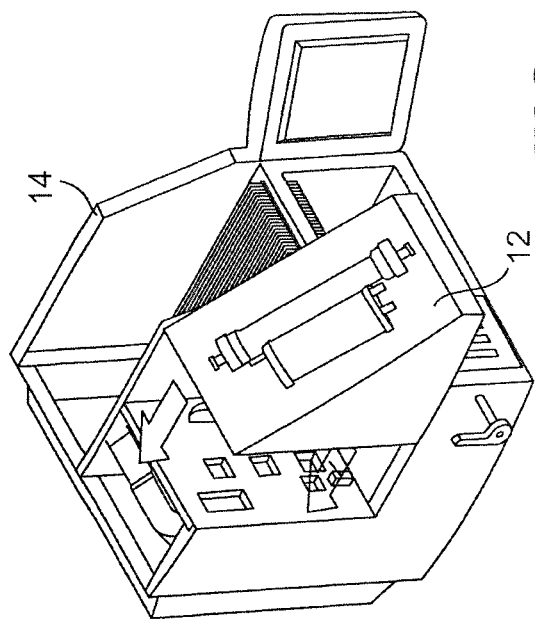
FIG. 10 illustrates the installation method of the cell culture module and instrumentation device of the cell culture unit of the present invention.

Referring to FIG. 1, disposable cell culture module 12 is removably attachable to instrumentation base device 14. The module requires multiple mechanical and electrical interfaces to the control instrumentation of device 14. Module 12 has interface features integrated into the module that mate with instrument interface features in the device to allow for a single motion installation (FIG. 10). As modules 12 are to be disposed of after use, it should be appreciated that numerous modules can be used in conjunction with a single base device 14 in successive production runs.

Figure 3:
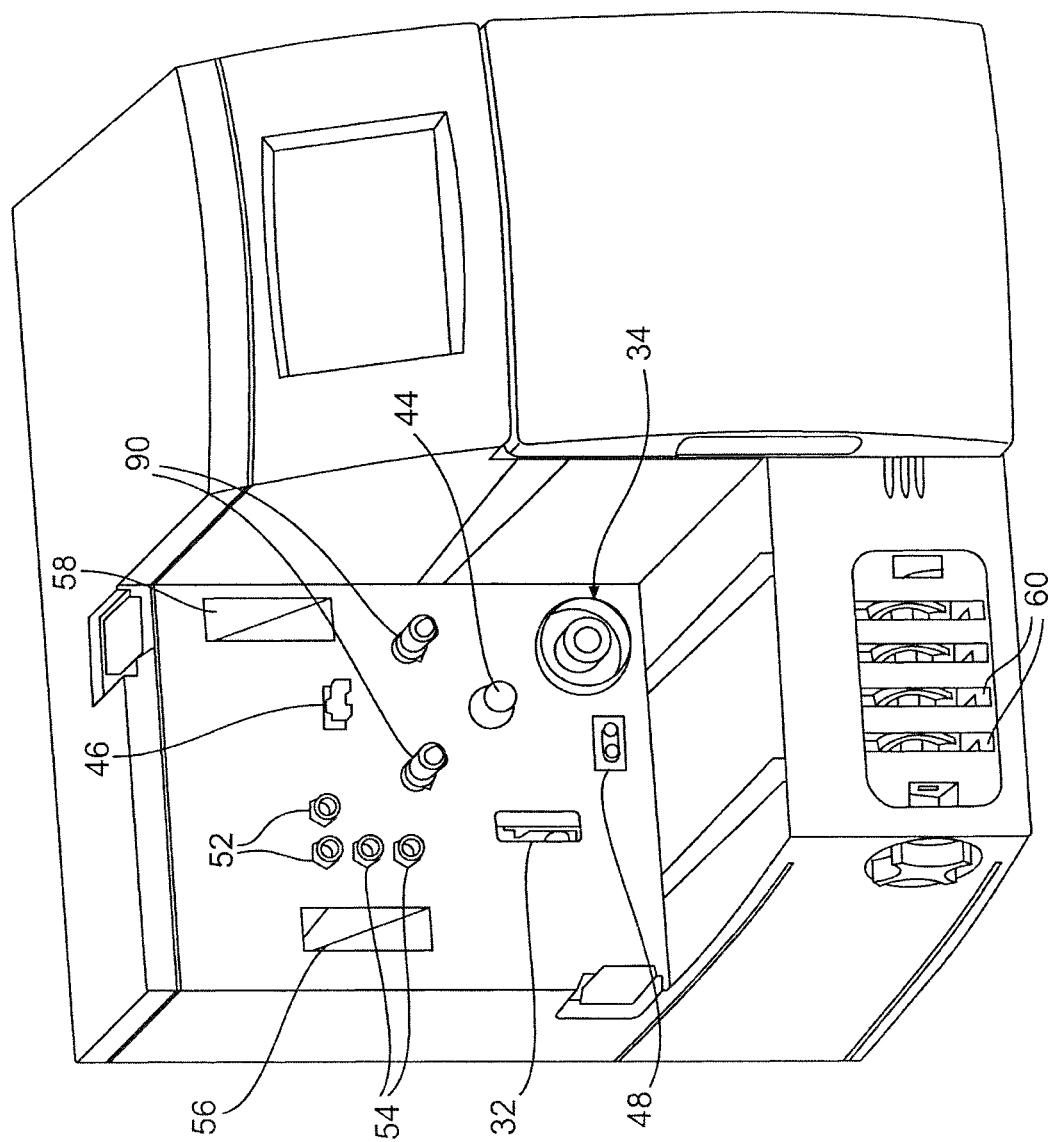
FIG. 3 is a perspective view of the instrumentation device of the cell culture unit of the present invention.
Figure 4:
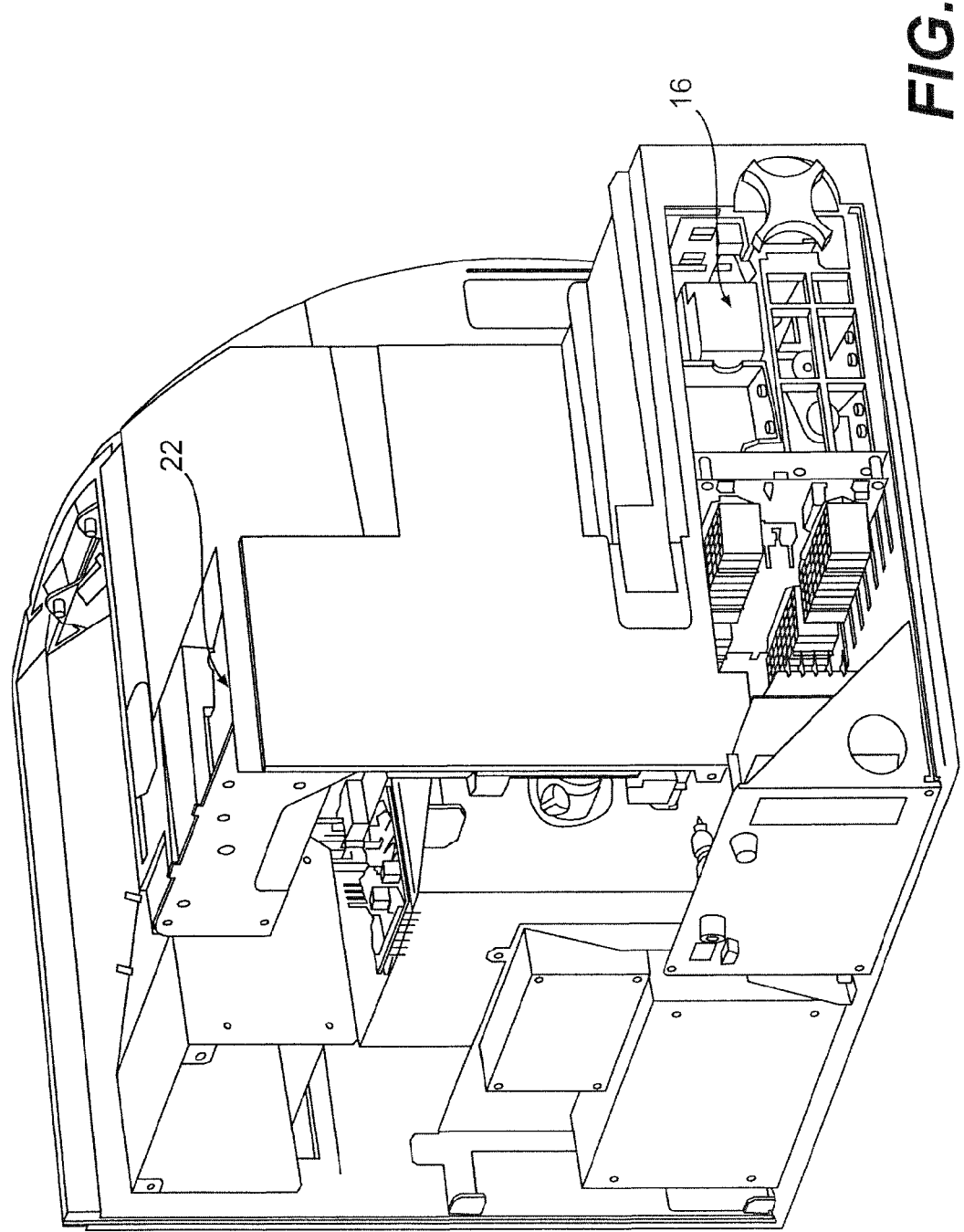
FIG. 4 is a rear and partial side view of the instrumentation device of the cell culture unit of FIG. 3, with covers removed.

As shown in FIG. 3, the interface features of device 14 include circulation pump drive 34, actuator valves 90 and cycling sensor 32. In addition, a temperature probe 44 and a flow sensor 46 interface with the components of module 12. Device 14 also includes an electrical connection 48 for pH probe 26 disposed within module 12.

Gas ports 52 communicate with gas exchanger 24. One port 52 communicates with the input to exchanger 24 and the other port 52 communicates with the output of the exchanger. Gas ports 54 control pressure to the cycling fixture 40. One port 54 communicates with the IC space and the other port 54 communicates with the EC space. As viewed from the front, the left port 52 is the exchanger output and the right port 52 is the exchanger input. The top port 54 is the IC reservoir pressurization port, and the lower port 54 is the EC reservoir pressurization port.

As described above, module 12 is heated to maintain cell fluid temperature. Heating mechanism 22 (FIG. 6) maintains the cell environment to promote growth and production. The cell culture, disposable modules 12 requiring elevated temperatures are warmed by fully encapsulating the module and attaching the module to the controlling instrument device 14, such that air ports are aligned and warmed air is forced into the module from the instrument at one location and allowed to escape at another. Instrument device 14 has a heated air outlet 58 and a return heated air inlet 56.

When disposable module 12 is installed onto the controlling instrument device 14, the air inlet 88 (FIG. 19) of the disposable module aligns with the air outlet 58 of the controlling instrument. Heating mechanism 22 (FIGS. 5 and 6) forces warmed air through outlet 58 (FIG. 3) and into the warmed air inlet 88 and into disposable module 12. The exhaust air exits through air outlet 86 and into air inlet 56 of instrument device 14 where it is circulated. The warmed air elevates the temperature of the components inside of the module 12, including the bioreactor 20. Preferably, through the use of the heating mechanism 22, the temperature within the EC space of the bioreactor 20 is maintained at a point or within a range to maximize virus infectivity and, virus replication, and viral yield. For example, in the case of wild-type influenza virus, the temperature in the bioreactor is preferably maintained within 37° C. to 39° C. for peak virus infectivity. The optimal temperature for rhinovirus replication is 33° C. to 35° C. While optimal temperature for wild-type influenza virus is 37-39° C., some mutant (cold adapted) strains grow best at 32-34° C., which is the temperature found in the oropharynx.

Figure 19:
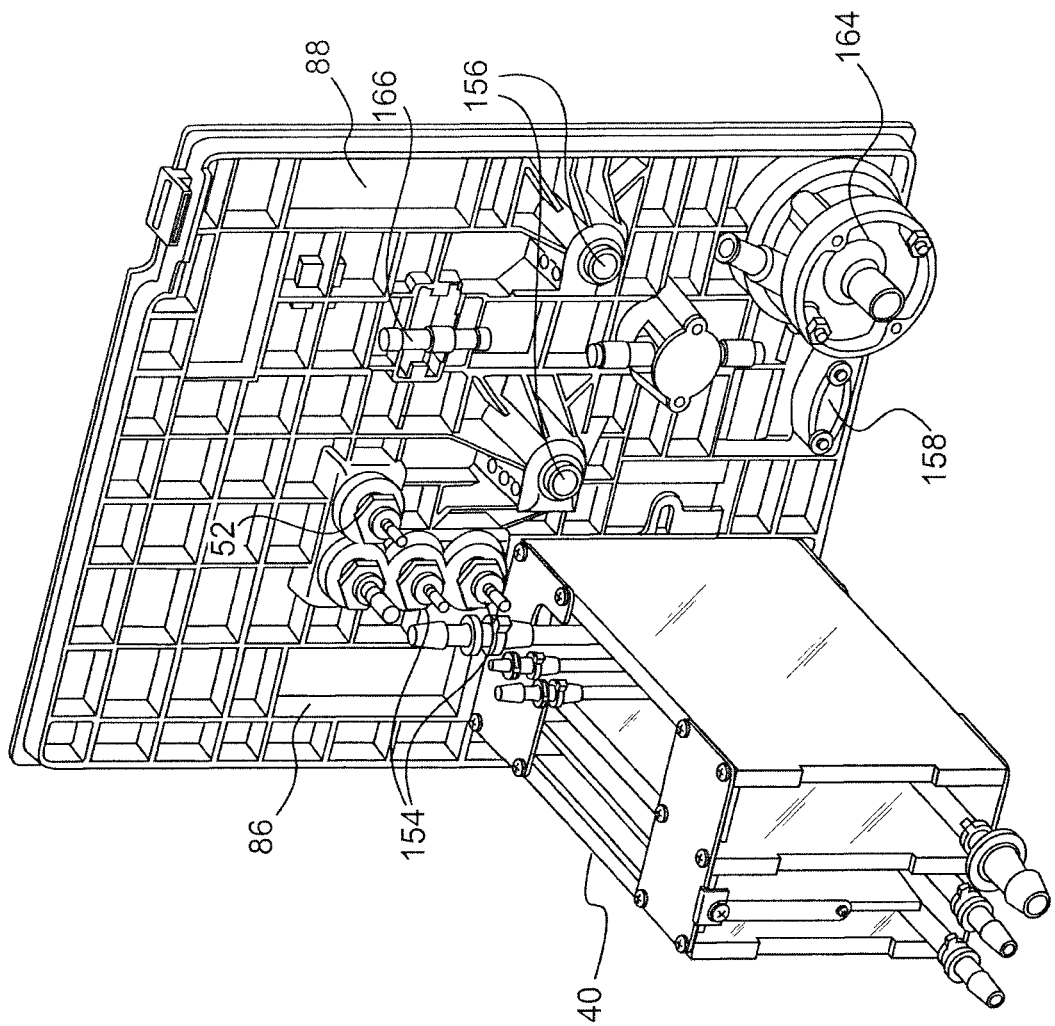
FIG. 19 is a perspective interior view of the back of the module of FIG. 17.

During installation, module 12 is aligned with the connections of the device 14 and the module is placed into the operating position as shown in FIG. 10. All mating interface features are functional. Referring to FIG. 19, when installed, certain features of the module 12, formed in a back panel 148 of the module, interface with device 14. Module air outlet 86 aligns with device air inlet 56 and module air inlet 88 aligns with device air outlet 58 to circulate heated air through module 12 as described herein. Gas connectors 152 and 154 engage device gas ports 52 and 54, respectively, to allow gas to enter and exit module 12. Valve bodies 156 receive actuator valves 90. Hub 158 receives pH probe 26 interface and aligns with electrical connector 48. Module 12 is connected to circulation pump drive 34 via module pump connection 164. Cycling unit 40 also communicates with cycling sensor 32 when the module is installed. The flow sensor 46 of device 12 mates with flow sensor connection 166. The temperature sensor 44 of device 14 mates with a non invasive receptacle in module 12 that is in contact with the IC media to provide control feed back to the control mechanism to regulate the thermal output of heater 22. The above mating connections facilitate the one-motion installation of the module 12 on the device.

Figure 7:
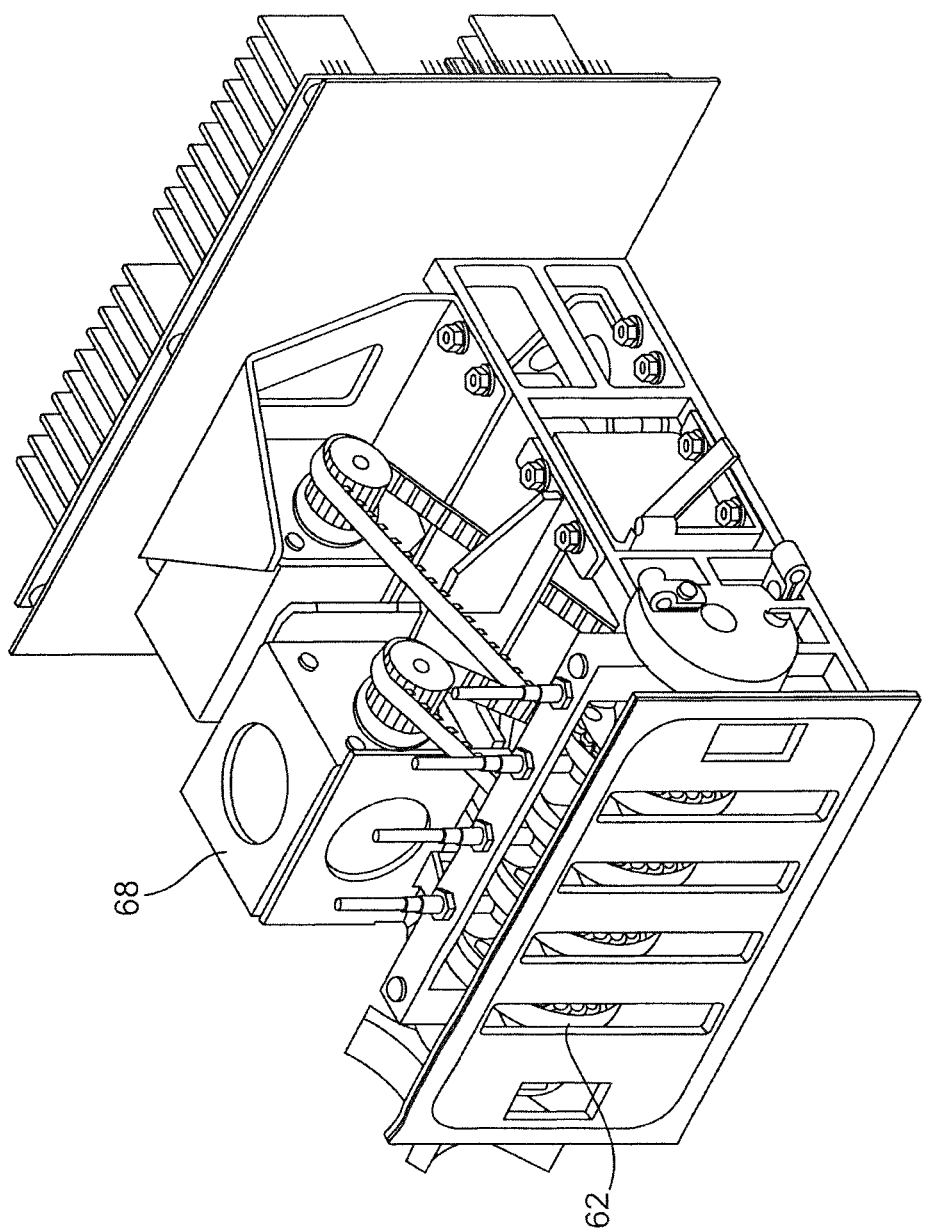
FIG. 7 is a perspective view of the variable output pump of the cell culture unit of the present invention.
Figure 8:
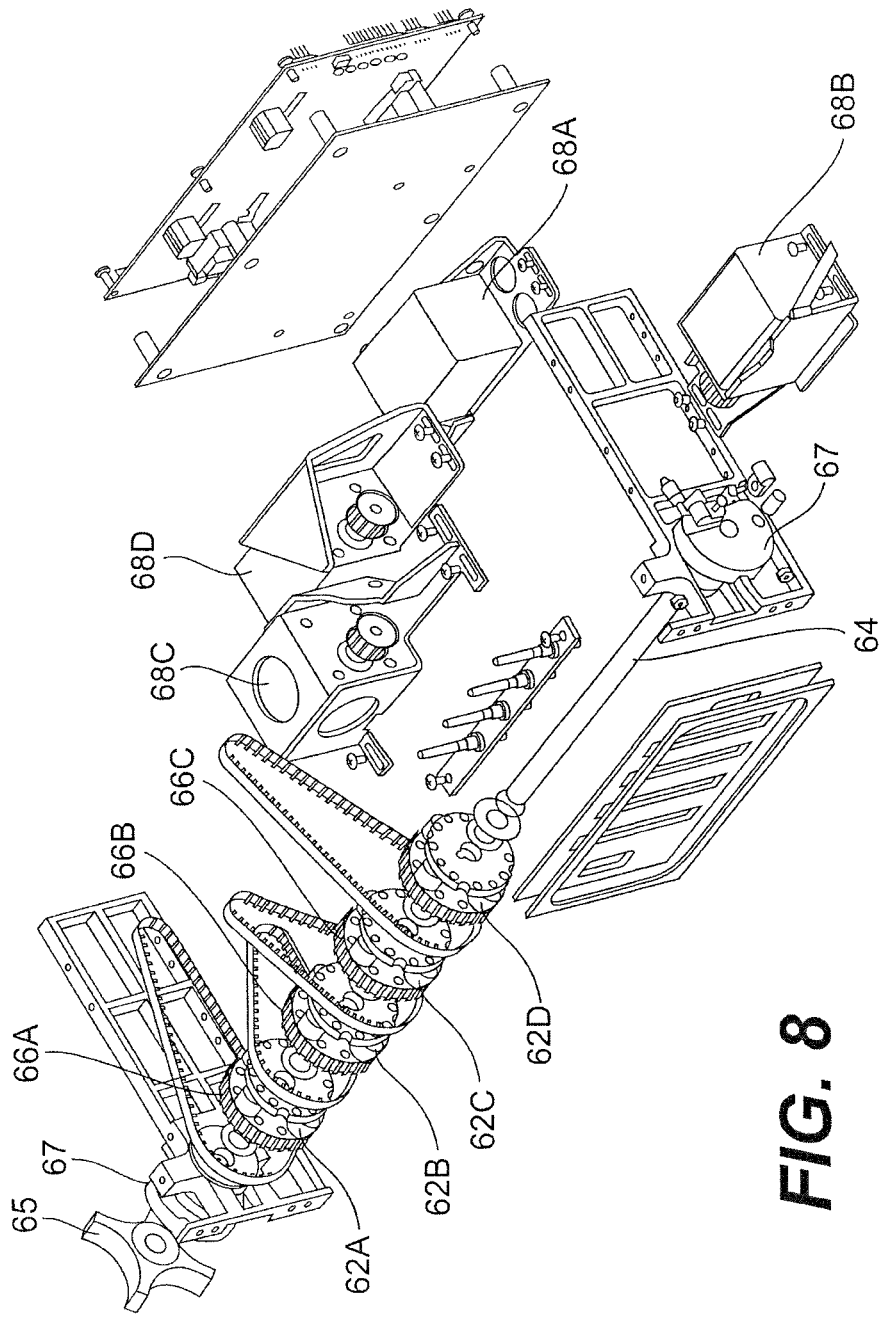
FIG. 8 is an exploded view of the pump of FIG. 7.
Figure 9:
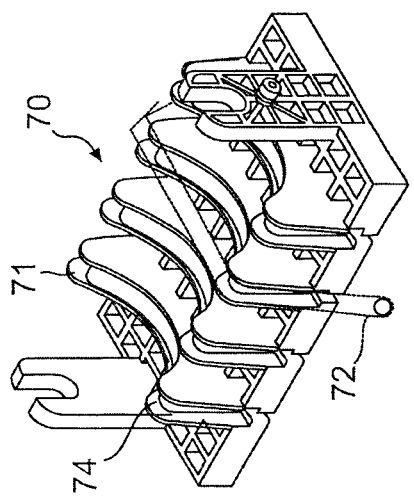
FIG. 9 is a perspective view of the pump cassette of the system of the present invention.

Referring to FIGS. 7-9, the instrumentation base device of the cell culture unit of the apparatus of the invention incorporates a multi-position, cassette loading, and peristaltic pump 16 (FIG. 2) with discrete, variable output control for each channel. A plurality of channels 60 (FIG. 3) are located in device 14. Although four channels are shown, it should be appreciated that pump 16 could have more or less channels.

As shown in FIG. 8, the pump has individual, variable control of the output of each channel. Pump rotors 62A-62D have a common fixed axial shaft 64 with individual servo drive. The occlusion rotors 66A to 66D are mounted to the pump rotors 62A-62D, which in turn are mounted on the single shaft 64 with internal bearings that allow for independent functional control by a respective reacting servo drive 68A-D. The single shaft minimizes tolerance accumulations typically caused by misalignment of individual rotors and shafts mating with a multi-channel cassette. Feedback sensors are included to verify rotation of the pump rotors.

Typical multi-channel peristaltic pump applications operate using a rotating drive shaft that is common to all rotors. This causes all rotors to turn at the same revolution per minute (RPM), yielding the same fluid output. Different inside diameter tubing may be used to give a fixed ratio delta output from one rotor to another. To obtain a variable output of the peristaltic pump segments, individual pump heads and drives are used. This requires individual tubing cassettes that must be loaded individually and does not allow for close center to center distance between pump heads.

As shown in FIG. 9, a multi-channel cassette 70 is featured with pre-loaded peristaltic tubing 72 to reduce loading errors and to reduce installation time. The mechanism includes a cam operated cassette insertion feature 74 ("cam feature") that interfaces with 67 on pump 16. As shown in FIG. 8, a knob 65 is rotated to move cam feature 74 into position to aid initial tubing occlusion during loading.

The cassette configuration is structured to hold multiple peristaltic tubing segments. A gripping feature 76 on the top and the bottom prevents the tubing from creeping during operation. This design allows for all tubing segments to be loaded into the pump drive mechanism at the same time. A latching feature 74 is also included to provide a bearing surface for the cam-operated latch 67 to react upon.

Figure 24:
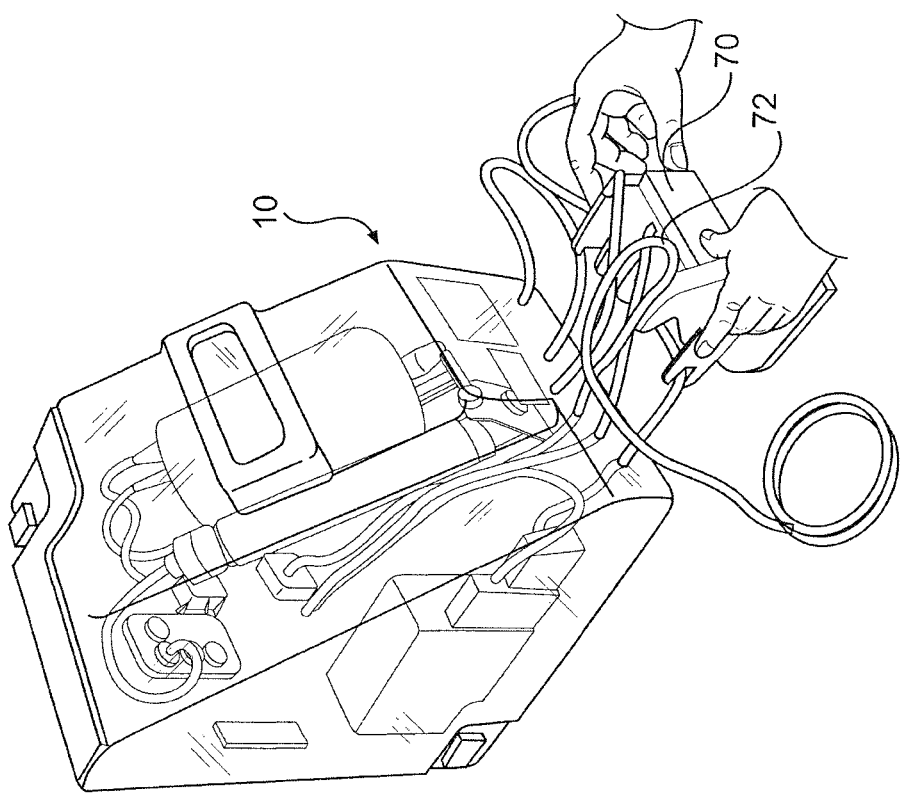
FIG. 24 is another perspective view of the cell culture unit of the present invention.

Referring back to FIGS. 1 and 2, cassette 70 is pre-loaded with peristaltic tubing (FIG. 24) and positioned in groove 80 on module 12. After module 12 is positioned on device 14, cassette 70 is removed and inserted into interface or plate 82. Each cassette section 71 (FIG. 9) supporting the tubing is inserted into a respective channel 60 (FIG. 3) of the interface 82. This configuration reduces tubing segment loading errors with pre-loaded multi-position cassettes, and reduces installation time.

Figure 11:
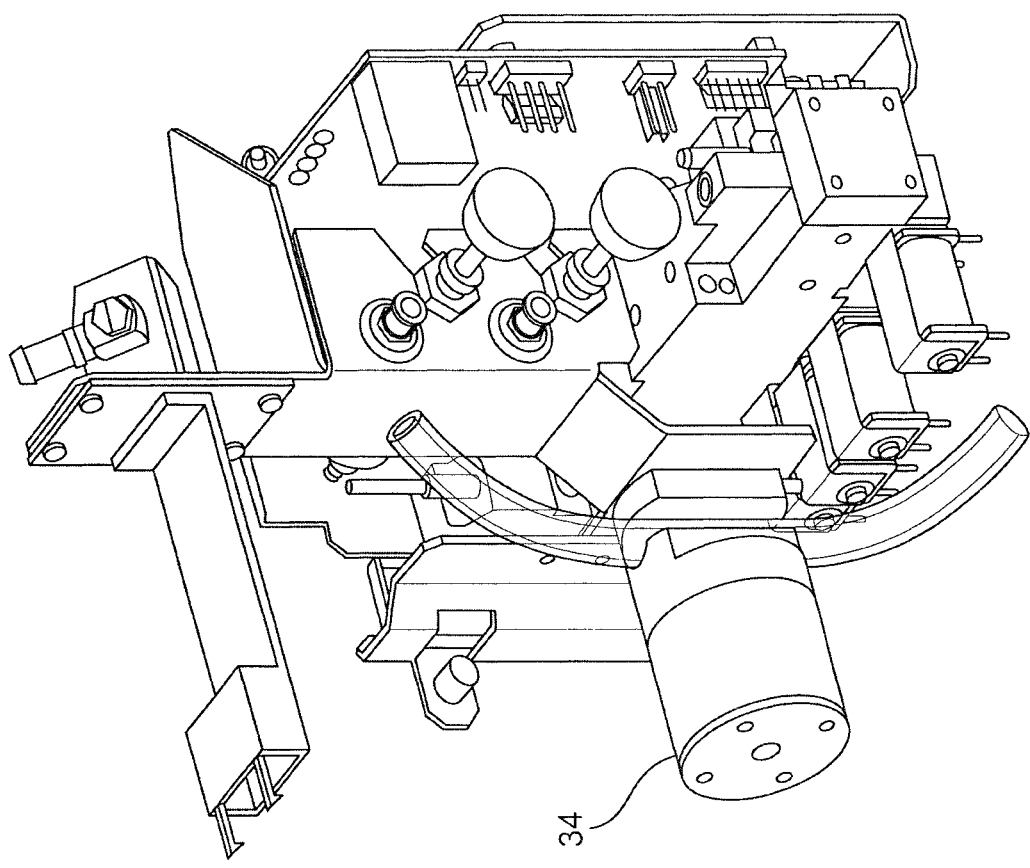
FIG. 11 is a perspective view of the gas blending and fluid cycling control of the module of the present invention.
Figure 12:
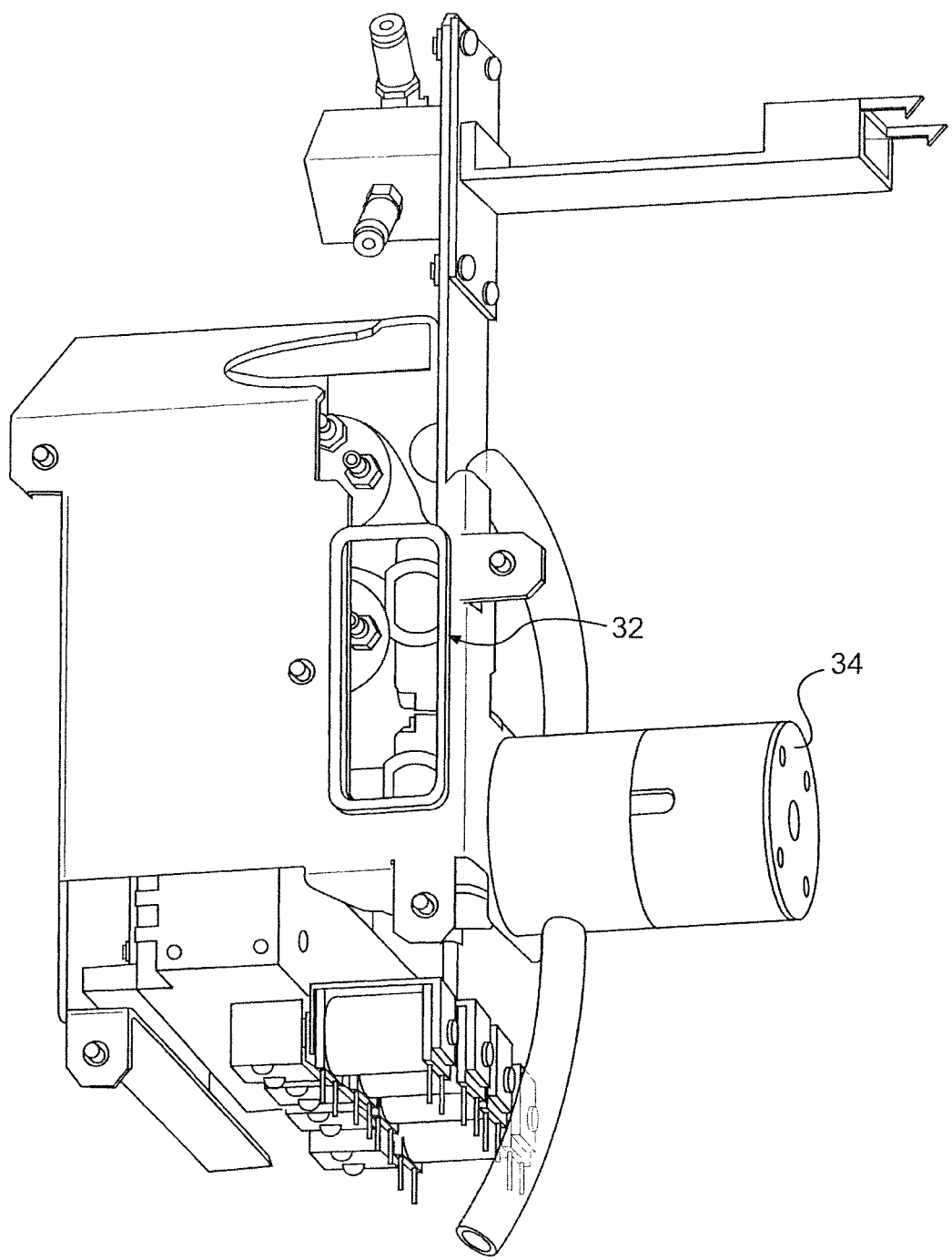
FIG. 12 is a front view of the fluid cycling control of FIG. 11.
Figure 20:
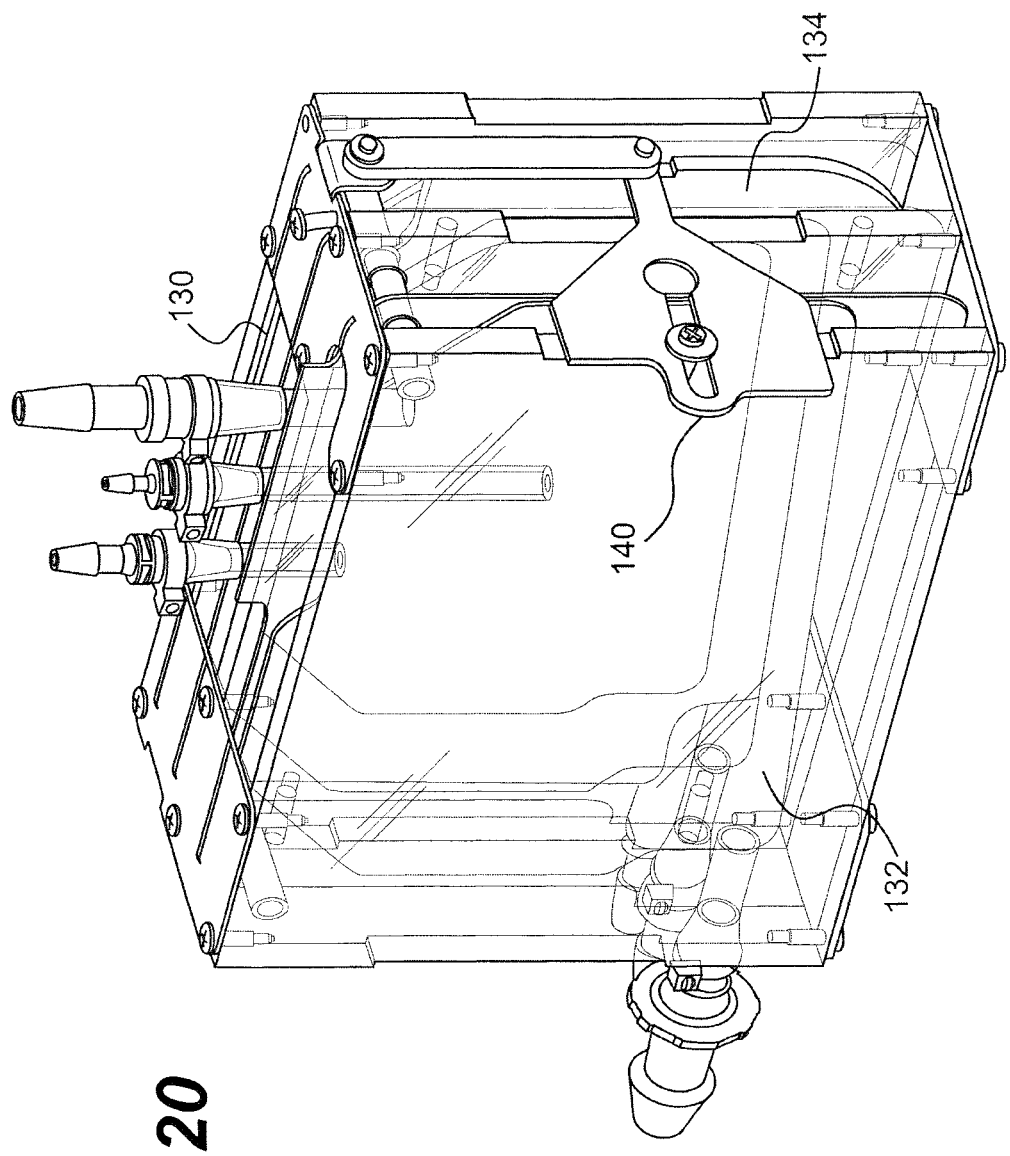
FIG. 20 is a perspective view of the extra-capillary cycling unit of the present invention.
Figure 21A:
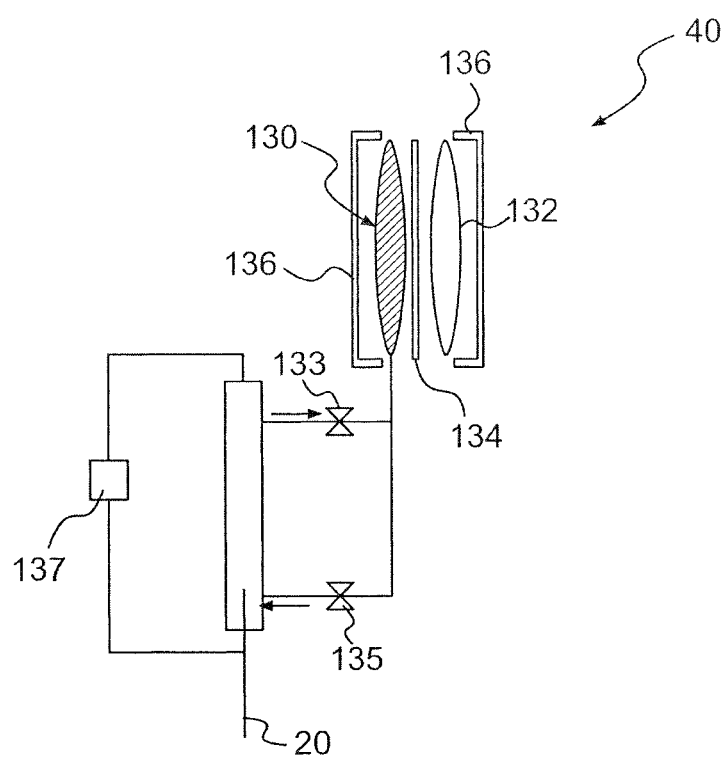
FIG. 21A is a flow diagram of the cycling unit of FIG. 20.
Figure 21B:
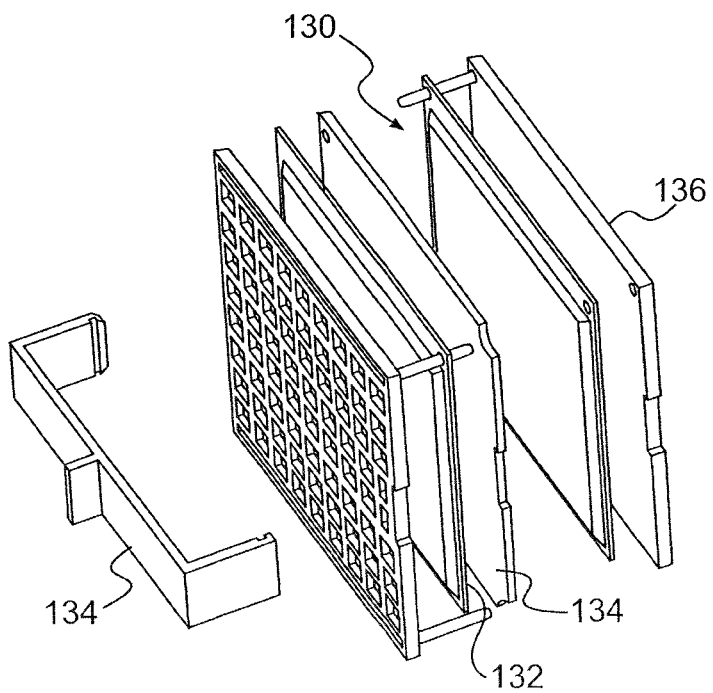
FIG. 21B is an exploded view of the cycling unit.

Referring to FIGS. 11 and 12, valves and sensors 32 in the instrument control the fluid cycling in the cultureware module 12. Two optical sensors detect the low or high position of the cycling position sensor flag 140 (FIG. 20). This information is used by a predictive algorithm to control the pressures applied to the IC chamber and EC pressure bag to effect cycling.

Figure 13:
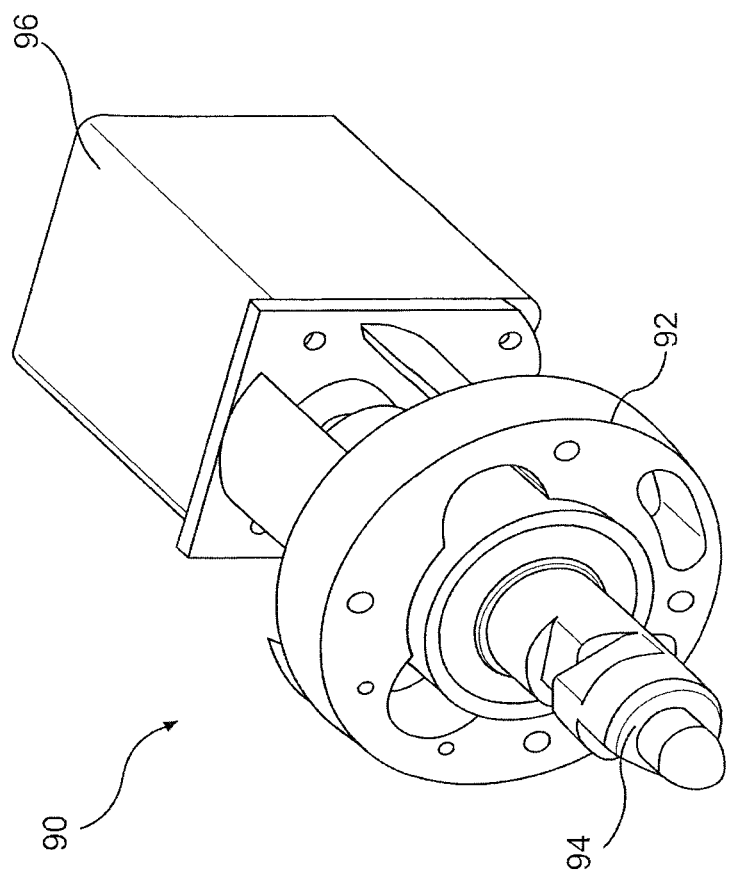
FIG. 13 is a perspective view of a rotary selection valve drive of the present invention.
Figure 14A:
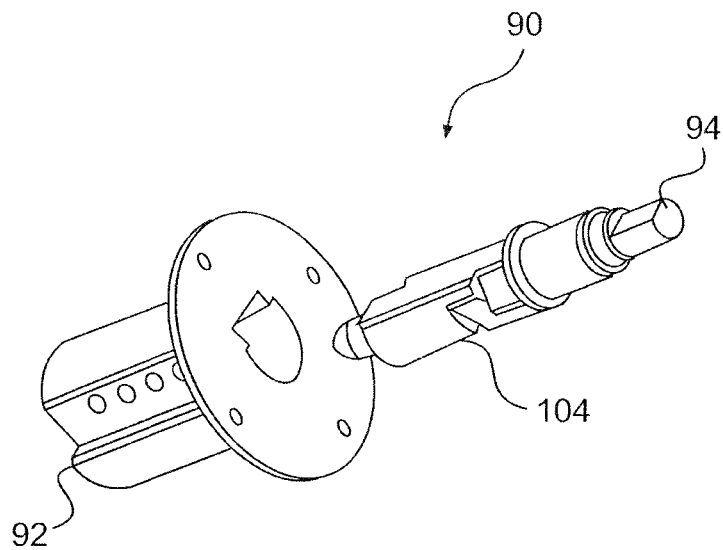
FIGS. 14A and 14B are exploded views of the valve rotor of FIG. 13. and the body used with it.
Figure 14B:
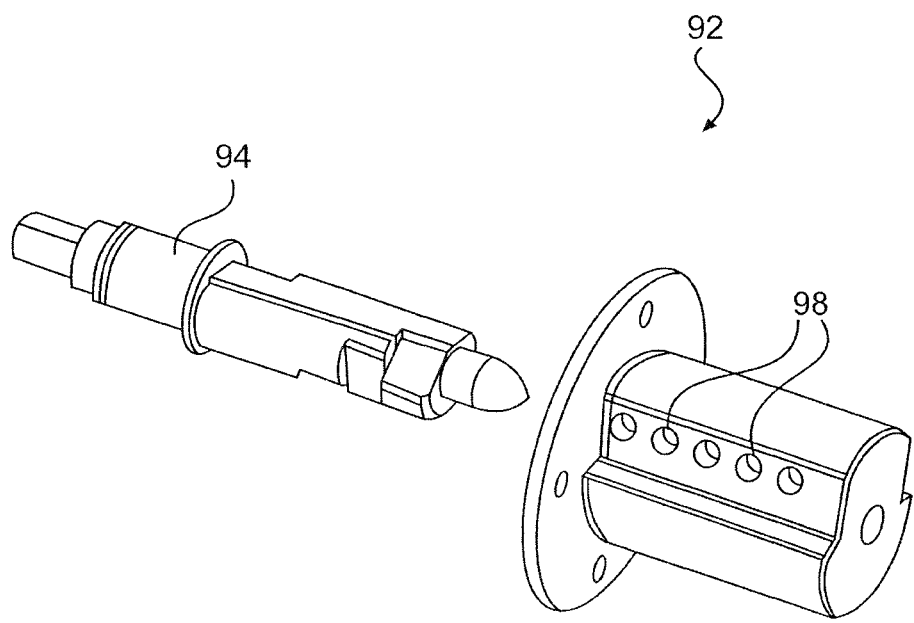

Sterilizable, disposable, actuator driven, rotary selection valves 90 are shown in detail in FIGS. 13-14C. Valve 90 comprises a valve housing 93 and valve cam 94. The elastomer tubing (not shown) is insertable through openings 98 in valve body 92 and is occluded by a rotating cam 94 that compresses the tubing against the valve body. This is accomplished by using a controlled, incremental, servo drive 96 (actuator and position feed back loop) to move cylindrical cam that reacts against immobile valve body 92 that holds the tubing in a constrained state. The cam design allows for a high area of the cam 104 to occlude the tubing and a low area of the cam 106 not to occlude, resulting in a closed and open condition respectively. Cam rotational positioning features may also be added to move cam 94 to predetermined positions. Configurations can be structured to accommodate multiple tubing segments in one device. The two piece design allows for fluid contact portion of the valve to be molded into the back panel 148 (FIG. 19) as a hub 156 and to be sterilized (EtO, chemical or radiation) with the rest of the fluid circuit and eliminates the need to be added separately.

The design of this clamp is meant to be used in an automated cell culture application where a disposable cultureware module interfaces with an electro-mechanical instrument. The combined unit is to be automated, which required various tubing lines of the disposable to be occluded/open to provide automated process control. The selector valve is used to automatically open and close tubing lines to direct fluid or gas flow during process control. Minimizing operator set-up is also a requirement. Preferably, the disposable cultureware can be inserted into the instrument in an operating position with no special operator procedures required for loading the tubing into the clamps.

In the cell culture and purification units of the present invention, the fluid path must be free of unwanted organisms (sterilized). Commercially available selector valves are not gas sterilizable. Sealing surfaces of the selected position may be unexposed to the gas sterilant and those surfaces may be "non-sterile" when the valve is repositioned. Valve 90 provides automated actuation of the cam, compactness, multiple lines, maintains valve position even with loss of actuator power, the disposable valve body is less costly than an equivalent switching valve, and can be incorporated into the back panel of 12. Offset occluded/open cam positioning of two tubing lines can insure a make-before-break switching of fluids. No power is required to maintain any operating position, and tubing segments used in the valve body can be sterilized.

It should be appreciated that a solenoid driven pinch mechanism, can be used in place of the actuator valve. This application may utilize a piston plunger actuated by an electrical coil to provide linear motion to pinch the tubing. A manual pinch clamp could also be used. The clamping position is manually activated by a mechanical bearing surface compressing the tubing and then held in position by a detent feature. This clamp type requires manual deactivation. A membrane over the series of ports could also be used. The membrane is actuated against the port to seal it. Multiple ports are configured for use as a selector mechanism.

In another embodiment shown in FIGS. 15A-15C, an actuator driven tubing slide clamp 110 with multiple positions and multiple tubing can be used as an alternative to valves 90. Elastomer tubing is occluded by sliding the tubing into a narrow slot 112 that compresses the tubing wall against itself. This is accomplished by using a servo drive (actuator and position feed back loop) to move a plate 110 with slot 112 in it and reacting against another plate or slide body 114 that holds the tubing in an immobile state. The moveable plate is designed with varying width slots to allow for position/positions to be inactive. This allows for normally open 116 or 118 and normally closed 117 positions. Configurations can be structured to accommodate multiple tubing segments in one clamp.

In operation, slide 110 is positioned into slide body 114. Tubing is inserted through tubing ports 108 and slide 110 at position 116 where both tubes are not occluded. A remote servo (not shown) engages into server drive slot 102 and moves the slide to position 117 where one tube is occluded and one tube is not occluded. The remote servo then moves the slide to position 118 where the occluded tube from the previous step is not occluded, and the tube from the not occluded tube from the previous step is now occluded. When moving the slide from position 117 to position 118, both tubes are occluded to insure that one tube is occluded before the other tube is opened. It should be appreciated that the number of tubes and configuration of the slide can be modified to meet customized applications.

The clamp is meant to be used in an automated cell culture application where a disposable cultureware module interfaces with an electro-mechanical instrument. The combined unit is to be automated, which required various tubing lines of the disposable to be occluded/open to provide automated process control. During process control the clamps are open/closed to simulate the function of an expensive, "disposable" switching valve. Minimizing operator set-up is also a requirement. The disposable cultureware can be inserted into the instrument in an operating position with no special operator procedures required for loading the tubing into the clamps. It provides automated actuation of slide clamp, compactness, multiple lines, maintains clamp position even with loss of actuator power, less costly than an equivalent switching valve. Offset occluded/open position of two tubing lines can insure a make-before-break switching of fluids. No power is required to maintain any operating position.

Figure 16:
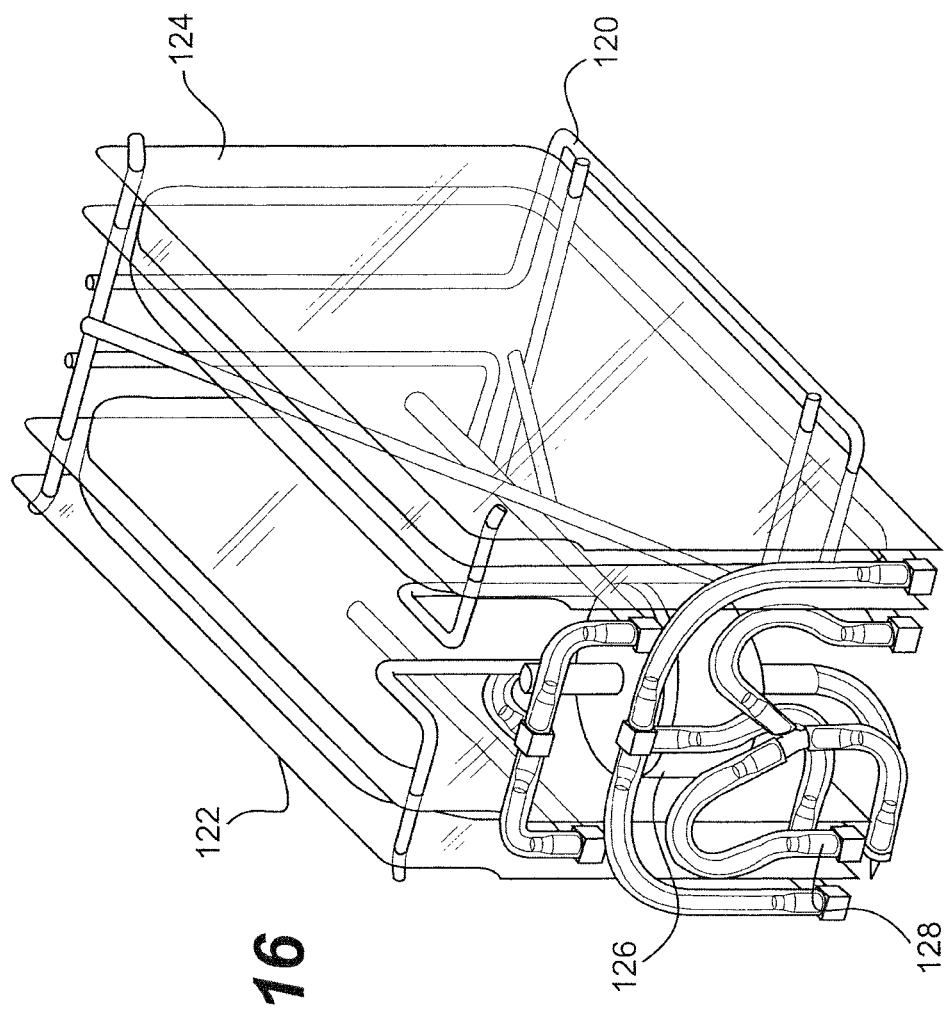
FIG. 16 is a perspective view of the factor and harvest bags of the present invention.

As described above, integrated temperature controlled storage area 18 maintains growth factors and harvested product (virus or VLPs) at a low temperature (approximately 4° C.). Referring to FIGS. 2 and 16, the controlled storage area preferably includes a rack 120 that is removably positionable within temperature controlled storage area 18. The rack 120 is designed to support a plurality of bags 122, 124. The bags are used to contain the smaller quantities of product (e.g., virus) or growth factors. It should be appreciated that other solutions can be disposed with the bags. For example, high molecular weight growth factor can be located with bag 122. This factor is connected via tubing 128 to the bioreactor or cell growth chamber 20 and the flow controlled by pump 16. Harvested virus or VLPs can be stored in bag 124. A cell filter 126 is provided to provide additional filtration. A filter bypass line is included if filtering of the harvest is not desired as in the case of cell collection. After the process is complete, the cells can be removed from the cell culture chamber via the tubing and stored in bag 124 until use. Optionally, harvested virus or VLPs can bypass the controlled storage area 18 and proceed directly to the purification unit.

Figure 17:
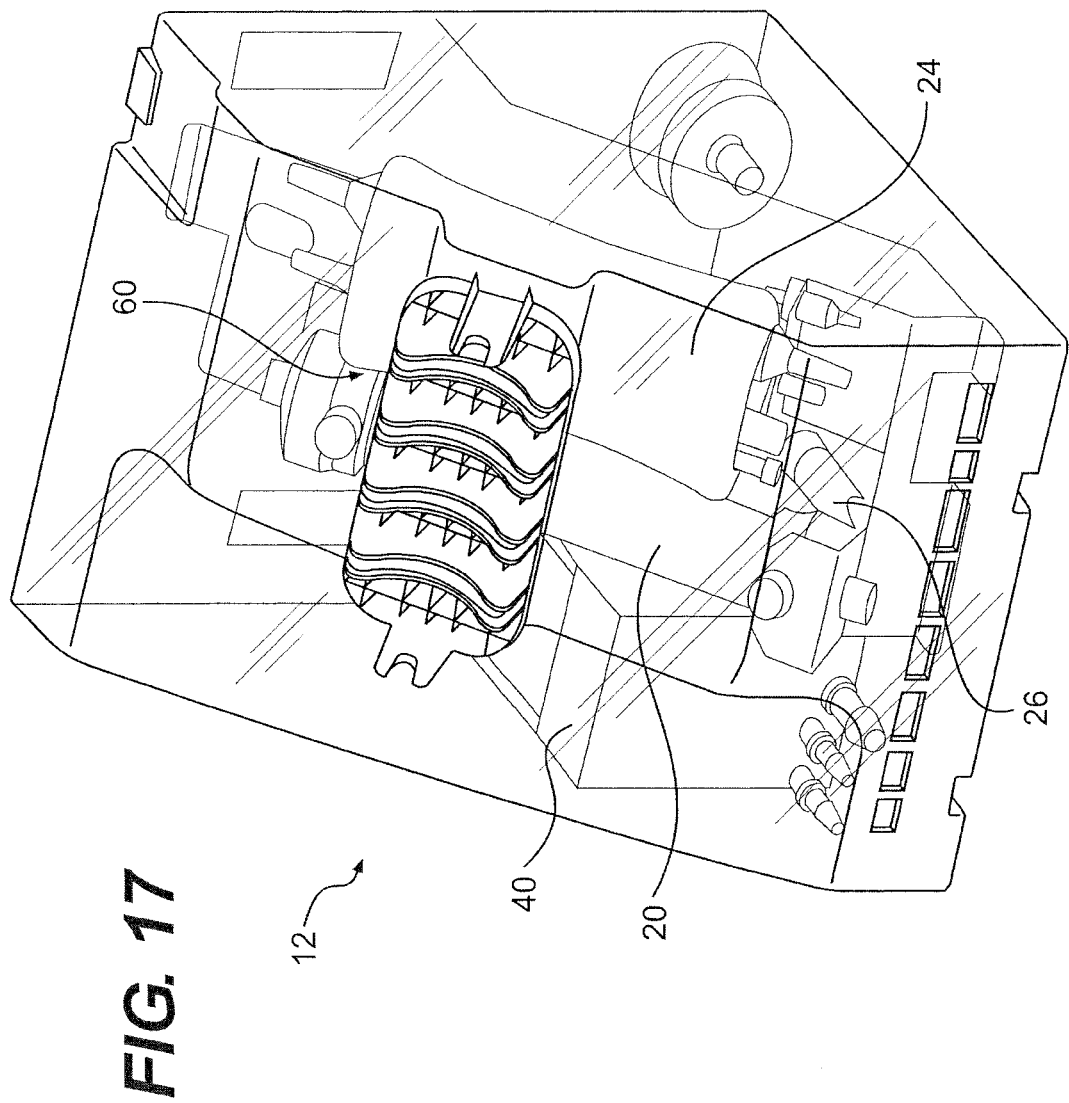
FIG. 17 is a perspective view of the disposable culture medium module of the present invention.
Figure 18:
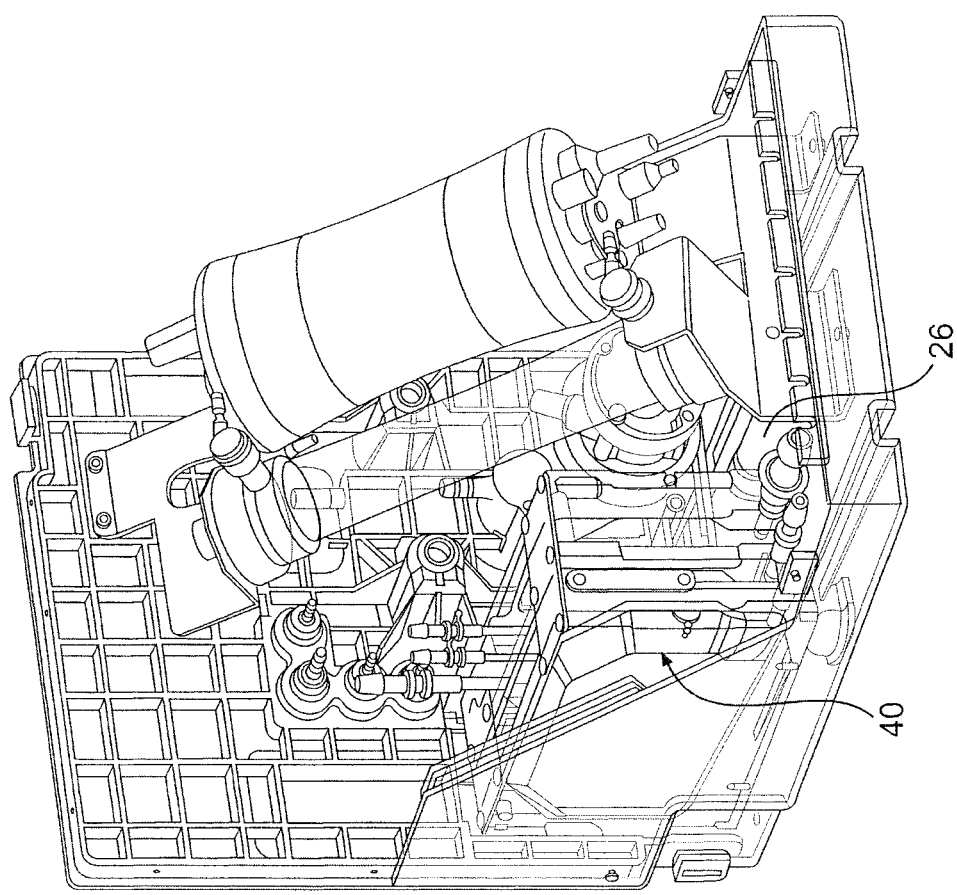
FIG. 18 is an interior view of the module of FIG. 17.

As shown in FIGS. 17-19, disposable cultureware module 12 includes fluid cycling unit 40 to maintain fluid volumes and cycling in the cell growth chamber. Referring to FIGS. 18-21, the present invention utilizes extra-capillary (EC) cycling in cell culture growth chamber 20 (FIG. 17) utilizing a non-rigid, EC reservoir 130 and mechanical or a second flexible reservoir 132 to cause elevated EC pressure. Reservoirs 130, 132 are separated by a sensor plate 134. Reservoirs 130, 132 are restricted in the maximum amount of expansion by a rigid mechanical housing 136. EC cycling is achieved by utilizing a non-rigid reservoir to retain the varying fluid volume associated with an EC circuit. Flexible reservoir 130 is fluidly connected to the bioreactor 20. Second flexible reservoir 132 is pressurized to apply force against the flexible reservoir 130 to provide an elevated EC pressure to cause an ultra-filtrative condition and force fluid into an intra-capillary (IC) circuit 138. A mechanical feed back position indicator 140 is physically connected to sensor plate 134 and moves with the physical expansion and contraction of the first flexible reservoir. The position of indicator 140 is sensed by the position sensors 32 and is used to control the force that is applied by second flexible reservoir 132. It should be appreciated that an alternate mechanical force apparatus may be used instead of a second flexible reservoir to cause pressure changes.

During operation the pressure is increased in the IC circuit 138 by pressurizing an IC reservoir 137. This pressure causes an ultra-filtrative condition that forces fluid transmembrane across the semi-permeable matrix of the bioreactor 20. The fluid is then forced through the connect tubing, through a flow control valve 133 and into the EC reservoir 130. Externally controlled pressure in the pressure reservoir 132 is allowed to vent. The expanding EC reservoir 130 forces the sensor plate 134 toward the pressure reservoir 132 and compresses it. Sensor plate 134 moves external position flag 140 and this is sensed when EC reservoir 130 has filled enough to expand to the EC upper level. The external position sensor 32 senses this position and the pressure in the IC reservoir 137, is decreased and the pressure in the pressure reservoir 132 is increased. This causes an ultrafiltrative condition and forces fluid out of the EC reservoir through a control valve 135, transmembrane across the matrix of the bioreactor 20 and into the IC circuit 138. The sensor plate 134 moves the external position flag 140 and the sensor 32 senses when the EC reservoir 130 has contracted to the EC low level.

The EC cycling unit offers fluid dynamics to cause fluid flow in the EC space thus minimizing nutrient and metabolic waste gradients that may be detrimental to the cells. It provides fluid level control without the use of ultrasonics or load cells that is not affected by cell debris. The flexible reservoirs are considerably less expensive and are suited for disposable applications. The sealed EC reservoir with cycling also limits contamination and isolates the cells.

The present invention also includes an indirect lactate control method for perfusion culture using $CO_2$ and pH sensing. The method predicts open system, perfusion culture, lactate levels in the circulatory medium by monitoring the pH and off-gas $CO_2$ level. This is accomplished by calculating the initial bicarbonate level of the media then utilizing the liquid pH and gas level of $CO_2$ to calculate current lactate concentration. This is used to control media dilution rate of the cell culture. The resulting calculated lactate value is used to set the perfusion rate of media dilution to maintain a pre-determined lactate level. Thus, an invasive sensing system or multiple off-line sampling is not required.

A physical relationship exists between bicarbonate buffer, $dCO_2$, and pH.

$$pH = pK + \log([HCO_3^-]/dCO_2]) \quad \text{Equation (1):}$$

where:
pH=the pH of the solution
pK=the acid ionization constant for bicarbonate
$HCO_3^-$=the current bicarbonate concentration (mM)
$dCO_2$=the concentration of dissolved $CO_2$ Lactic acid production by the cells appears to be the dominant driving force for pH changes in cell culture media. Based on this observation, each mole of lactic acid produced results in consumption of one mole of bicarbonate as described by the following equation:

$$[HCO_3^-] = [HCO_3^-]_0 - [\text{Lactate}] \quad \text{Equation (2)}$$

where:
$[HCO_3^-]_0$=the initial bicarbonate concentration in the medium (mM)
Lactate=the lactate concentration (mM)

Equation (3) provides a simple relationship—Henry's Law, that equilibrium $dCO_2$ is proportional to the gas phase concentration of CO2.

$$dCO_2 = a(\% CO_2) \quad \text{Equation (3):}$$

where:
a=$CO_2$ solubility conversion (mM/%)
% $CO_2$=concentration of $CO_2$) in the gas phase that is in equilibrium with $dCO_2$ (%).

Equation (4) is derived by substituting Equation 2 in Equation 1 as follows:

$$pH = pK + \log\{([HCO_3^-]_0 - [\text{Lactate}])/[dCO_2]\} \quad \text{Equation (4)}$$

Equation 5 is derived by combining Equations 3 and 4:

$$pH = pK + \log\{([HCO_3^-]_0 - [\text{Lactate}])/[a(\% CO_2)]\} \quad \text{Equation (5)}$$

The operating equation, Equation (6) is derived by solving for Lactate in Equation (5):

$$\text{Lactate} = [HCO_3^-]_0(a) * (\% \ CO_2) * 10^{(pH-pK)} \quad \text{Equation (6):}$$

The values of pK and (a) were found to be 6.38 and 0.39, respectively.

Upon taking a lactate and pH reading, the value of (a) is calculated. The initial bicarbonate concentration is calculated as the calibration constant. The advantage is that the bicarbonate concentration does not have to be known when using the present calibration method.

Figure 22:
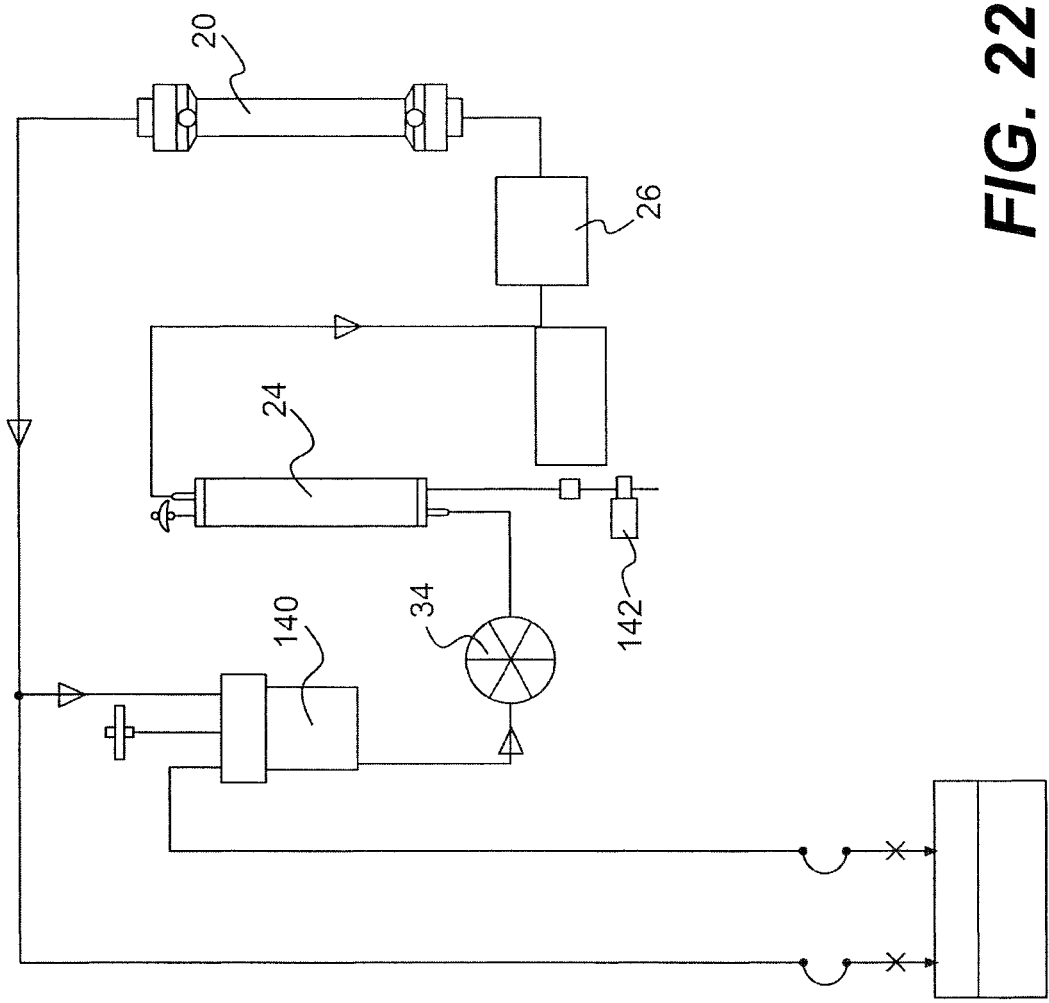
FIG. 22 is a flow diagram of the lactate control system of the present invention.

The application is shown in FIG. 22. In a bioreactor perfusion loop, the growth media is pumped from an IC reservoir 137 via pump drive 34, 164, circulated to the gas exchange cartridge (GEX) 24, pH sensor 26, bioreactor 20, and then back to reservoir 137.137. Blended gases are passed through the membrane gas exchange cartridge that oxygenates the media and regulates $CO_2$. Per Henry's Law, the $CO_2$ levels in the gas phase or air side of the GEX 24 is in equilibrium with the liquid phase of the media. The discharge end of the GEX is monitored with a $CO_2$ sensor 142 that resides in the device 14 and the lactate is calculated per Equation (6). When the media lactate level is known, the instrument uses automatic, media dilution, control to maintain the predetermined set point.

The present invention utilizes existing signals and with the addition of a non-invasive gas $CO_2$ sensor incorporates lactate control to control media feed rate for cell growth and production. Utilizing the invention reduces materials and labor associated with recurring off-line testing. Utilizing the invention allows for continual adjustment of the dilution rate that would otherwise be inefficient and costly if step increases were used as in previous technologies.

Utilizing the present invention increases the predictability of cell culture metabolics and allows a perfusion cell culture system to have an increased level of automation. The lactate and media dilution rate can be used to determine the state of cell growth and production.

The present invention also utilizes a novel approach for pH sensing in a cell culture system. Referring back to FIGS. 2, 18 and 19, pH probe 26 and a holder are preferably built into the disposable cultureware module 12, thus the user is not required to add the probe to the cultureware. Probe 26 is intended to be a one-time use device that is disposed of with the cultureware. The probe is disposed of with the used cultureware, so no time is spent recovering the probe for cleaning, revalidating and reuse.

In operation, the probe 26, for example, a solid gel filled electrode, is mounted in a holder 28 (FIG. 23) through which the media to be sensed flows. The electrode in the holder is fluidically connected to the cultureware circuit, mounted in the cultureware module, the circuit is checked for fluidic integrity, and sterilized with the completed cultureware (ethylene oxide, EtO). After sterilization, QC checks are performed on the EtO process to provide high confidence of sterilization. When an operator wishes to culture cells, the cultureware is removed from the pouch, loaded on the instrument and fluid is introduced into the cultureware. A period of time is given to re-hydrate the electrode. The cultureware is brought to operating conditions, the electrode is calibrated and then used to control pH in the cultureware. When the cell culture is complete, the operator can dispose of the cultureware and the probe. Although the probe has been described as a solid gel electrode, other probe types could be used (e.g., an ISFET, liquid filled, immobilized phenol matrix, fluorescence, etc.).

Figure 23:
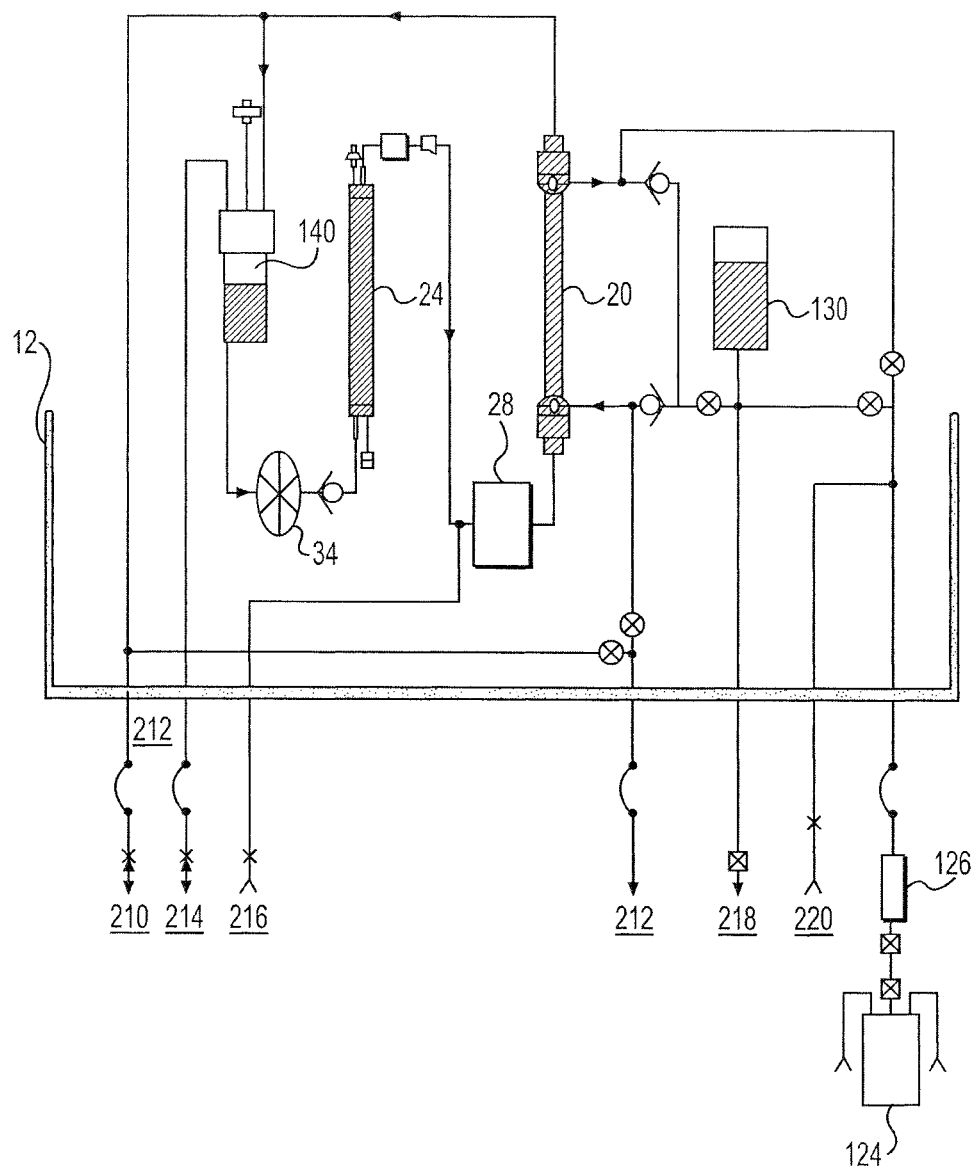
FIG. 23 is a flow diagram of the system of the present invention.

Referring to the flow diagram of FIG. 23, pump 16 moves fresh basal media into the cultureware at media line 210. Media line 210 is connected to a user provided container of fresh media to provide the growth nutrients to the cell culture that are pumped into the disposable. Outflow line 214 is connected to a user provided container to collect the waste or spent media being pumped out of the disposable. Factor line 212 is connected to a user provided container of growth factors that are pumped into the bioreactor 20 of the disposable cultureware module 12. EC inoculate can be added at 220 and IC sample at 216. Product harvest (virus) is removed at 126. The cells are harvested at 218. Harvest line 218 is preferably a pre-attached container that is part of the disposable cultureware module 12 that is used to collect the product that is pumped out of the bioreactor 20 and disposable cultureware module 12. Pump 16 has multiple lines 210, 214, 212 and 126. Because the pump of the present invention has a common fixed axial shaft and individual servo driven rotors, the control of the flow of each can be independent, allowing one channel or flow to be increased while another decreased.

Figure 25:
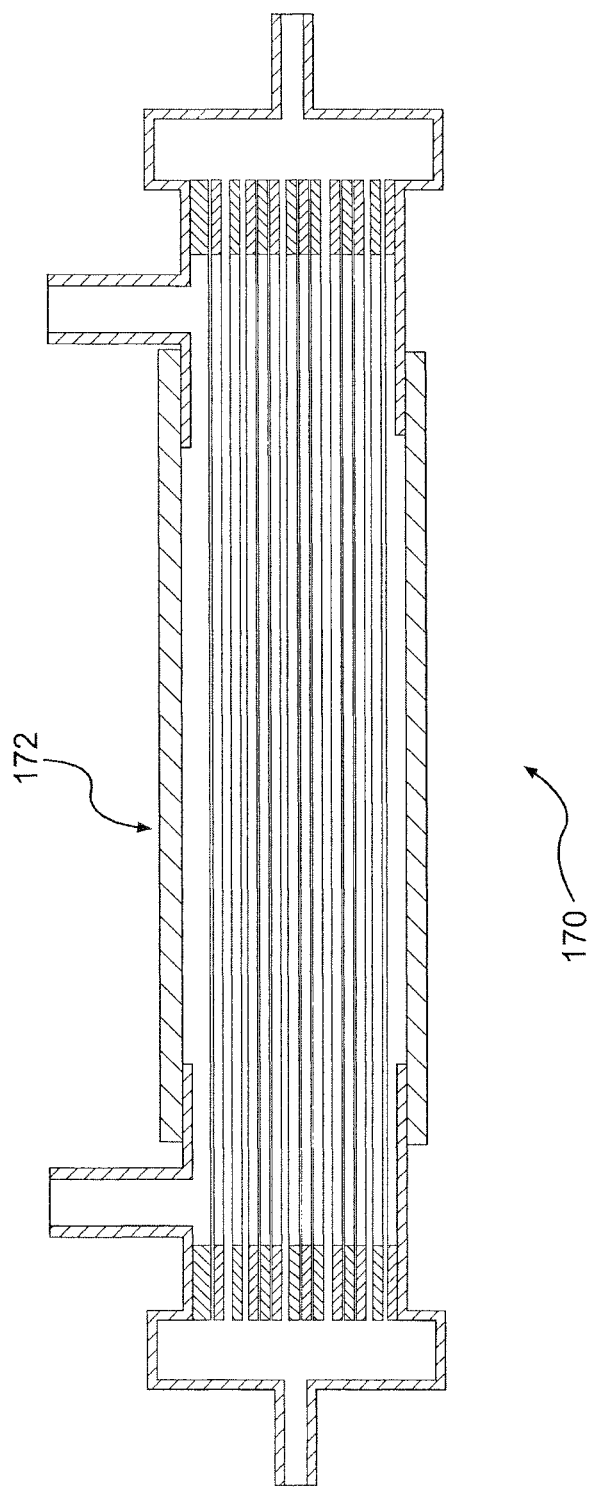
FIG. 25 is a cross-sectional view of a hollow fiber bioreactor, which may be used for production of virus according to the present invention.

As shown in FIG. 25, in one embodiment, the bioreactor 20 is a flexible bioreactor 170 having a flexible outer body 172 that allows for physical movement of the cell growth substratum (hollow fibers, membrane or other suitable matrix) when a resultant torqueing or bending moment is applied to the bioreactor ends. Flexible outer body 172 allows for the bioreactor case to be flexed, causing fiber movement. This fiber movement enhances the release of cells that have attached to the side of the bioreactor matrix, if harvesting of cells is desired. The cells can then be harvested by flushing either after or during the manipulation. This method can provide increased efficiency of cell harvest at high cell viabilities without the use of chemical or enzymatic release additives.

A bioreactor can be constructed using an outer housing that incorporates a flexible center section. This center section is composed of a flexible, non-permeable tubing that allows each end of the bioreactor to be manipulated, thus causing movement of the growth matrix. The purpose of this movement is to release the attachment or clumping of products on the extra-capillary (EC) side of the fibers. The products can then be flushed from the EC via the access port at each end of the bioreactor.

Harvesting cells from a matrix-containing bioreactor such as a hollow fiber bioreactor has been difficult to accomplish. Typically, cells are sticky and attach themselves to the fibers or to other cells and form clusters. Rapid flushing of media through the EC space to hydraulically force the cells free and into the harvest stream is the most basic method of harvesting cells from the EC space. Typically the quantity of cells harvested is low because the flushing media tends to shunt through the EC and flush cells only from the limited fluid path.

Another method is to physically shake or impact the outer housing to release the cells or clumps of cells. This practice may cause physical damage to the bioreactor or its associated components. Another method includes the use of chemicals to disrupt the adhesion of cells to the fibers or to disrupt the clumps of cells. Adding chemicals to a controlled process may cause adverse effects on cell viability and can introduce an unwanted agent in the down-stream processing.

Figure 26:
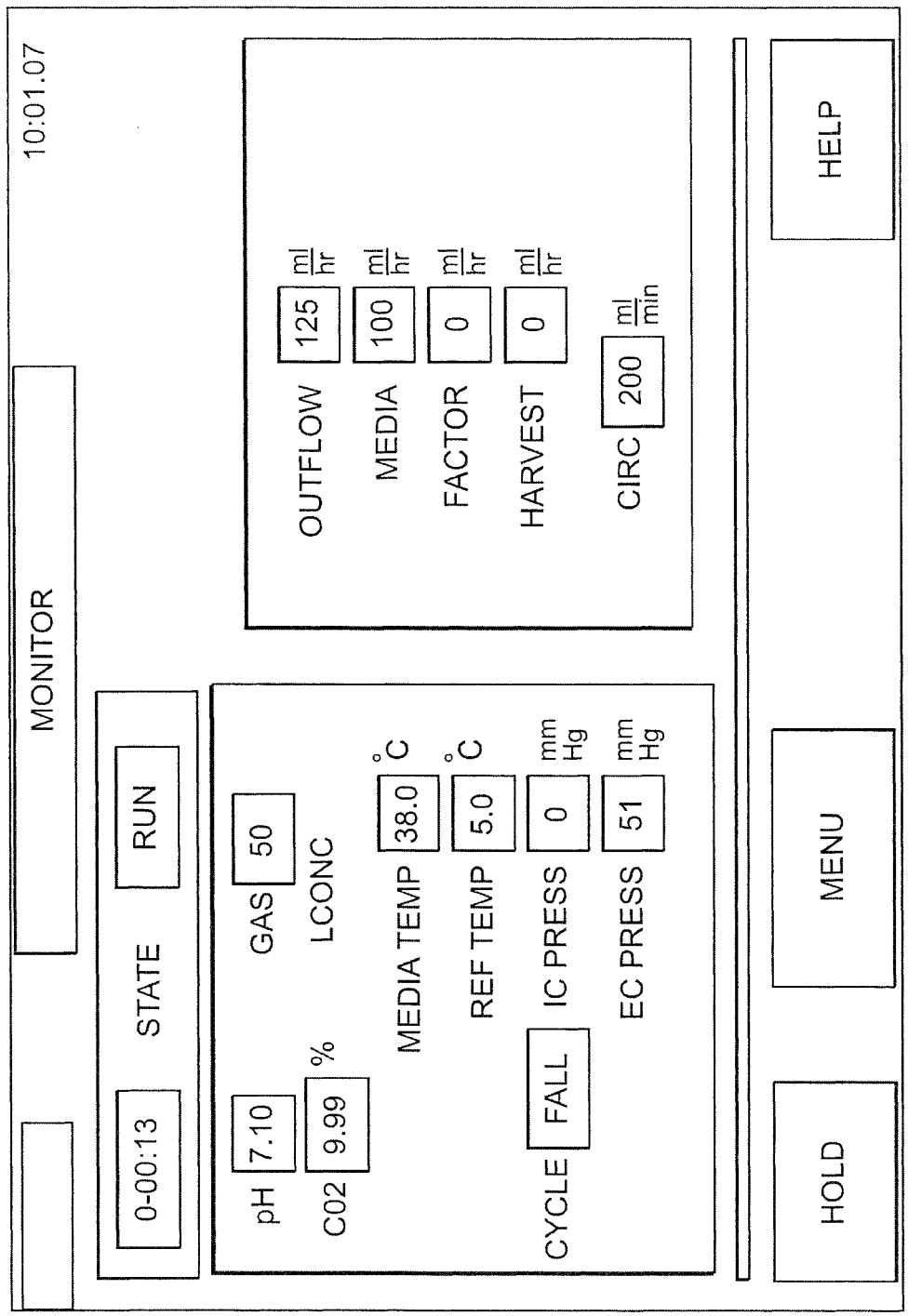
Figure 27:
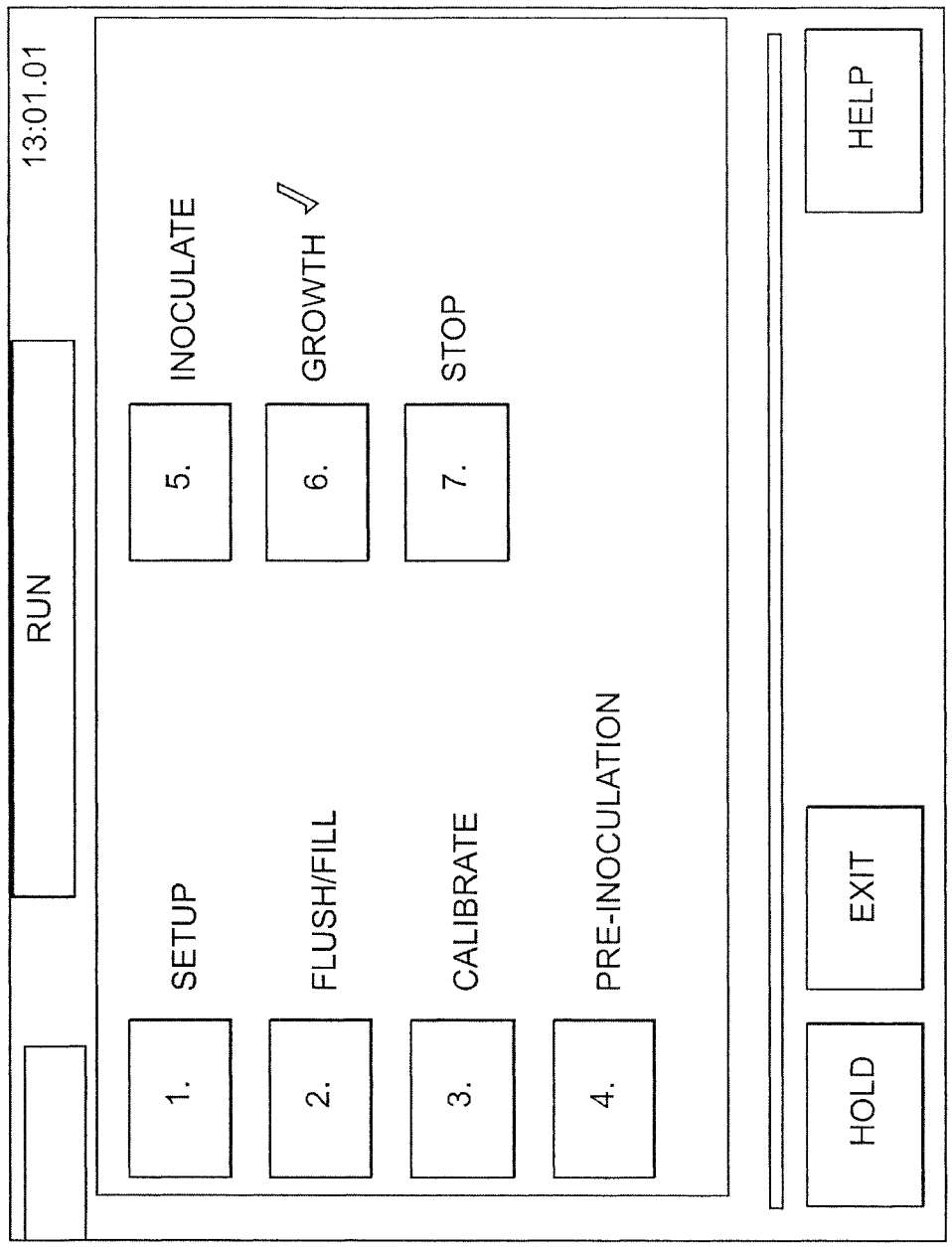
Figure 29:
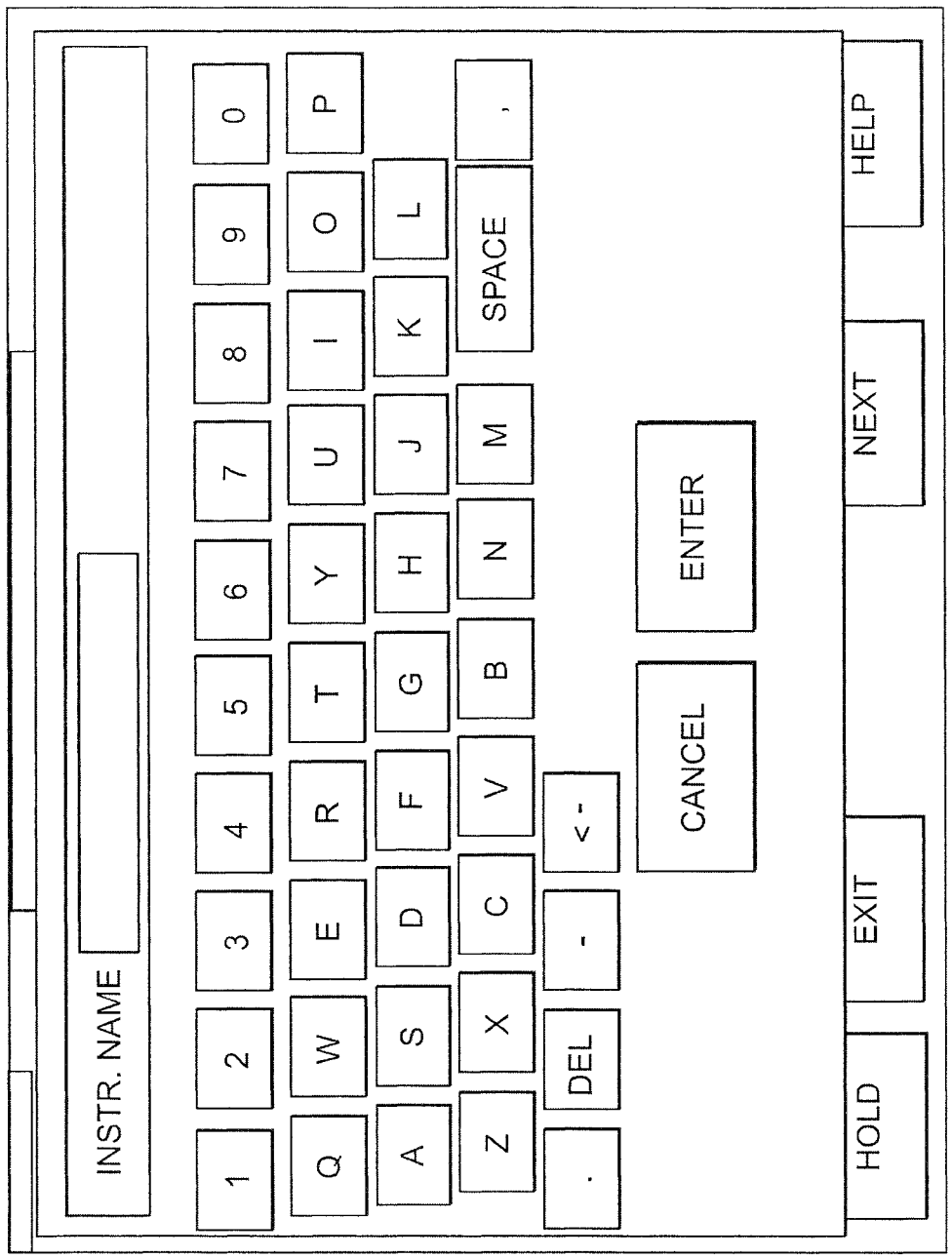
Figure 30:
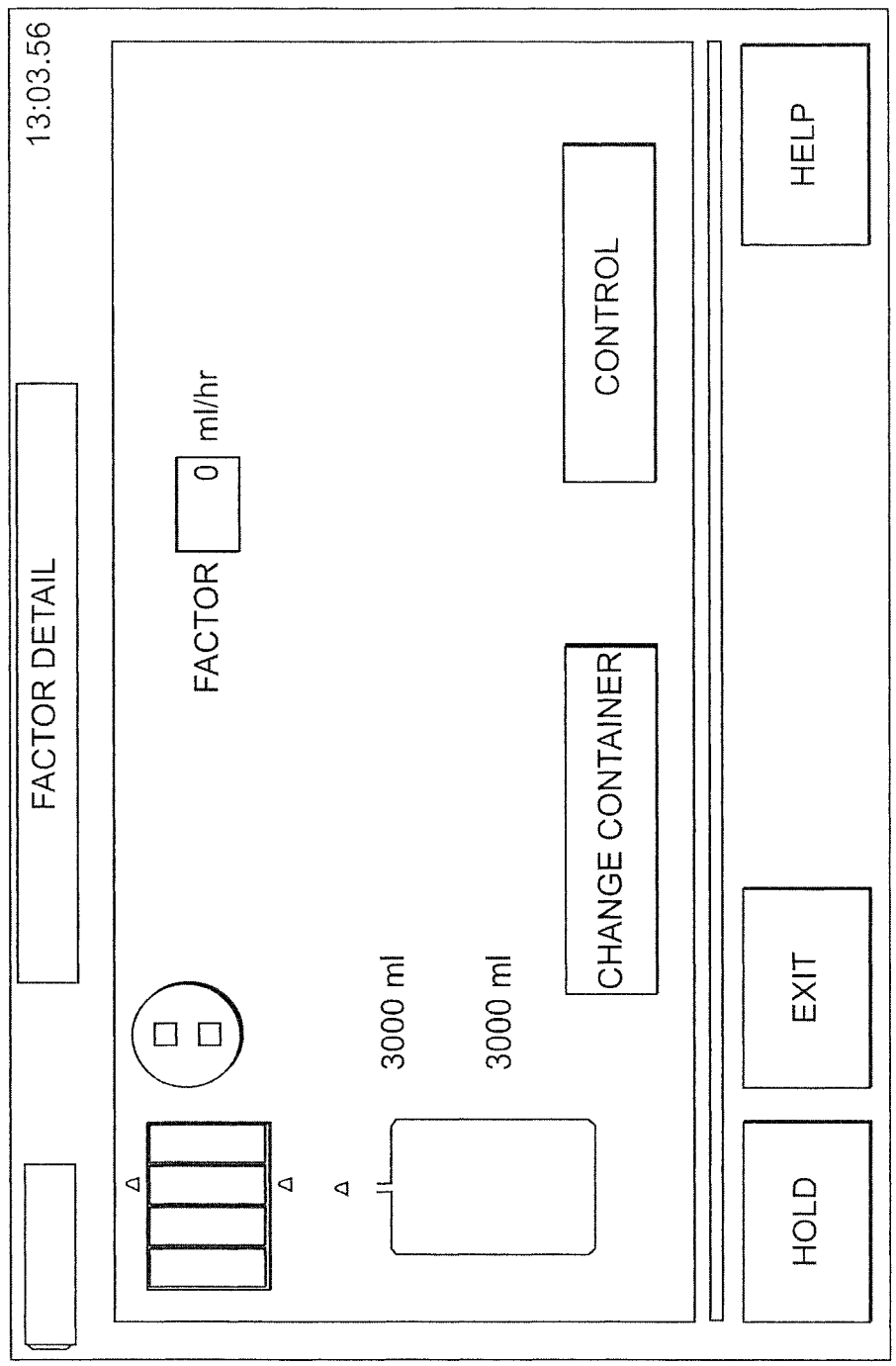
Figure 31:
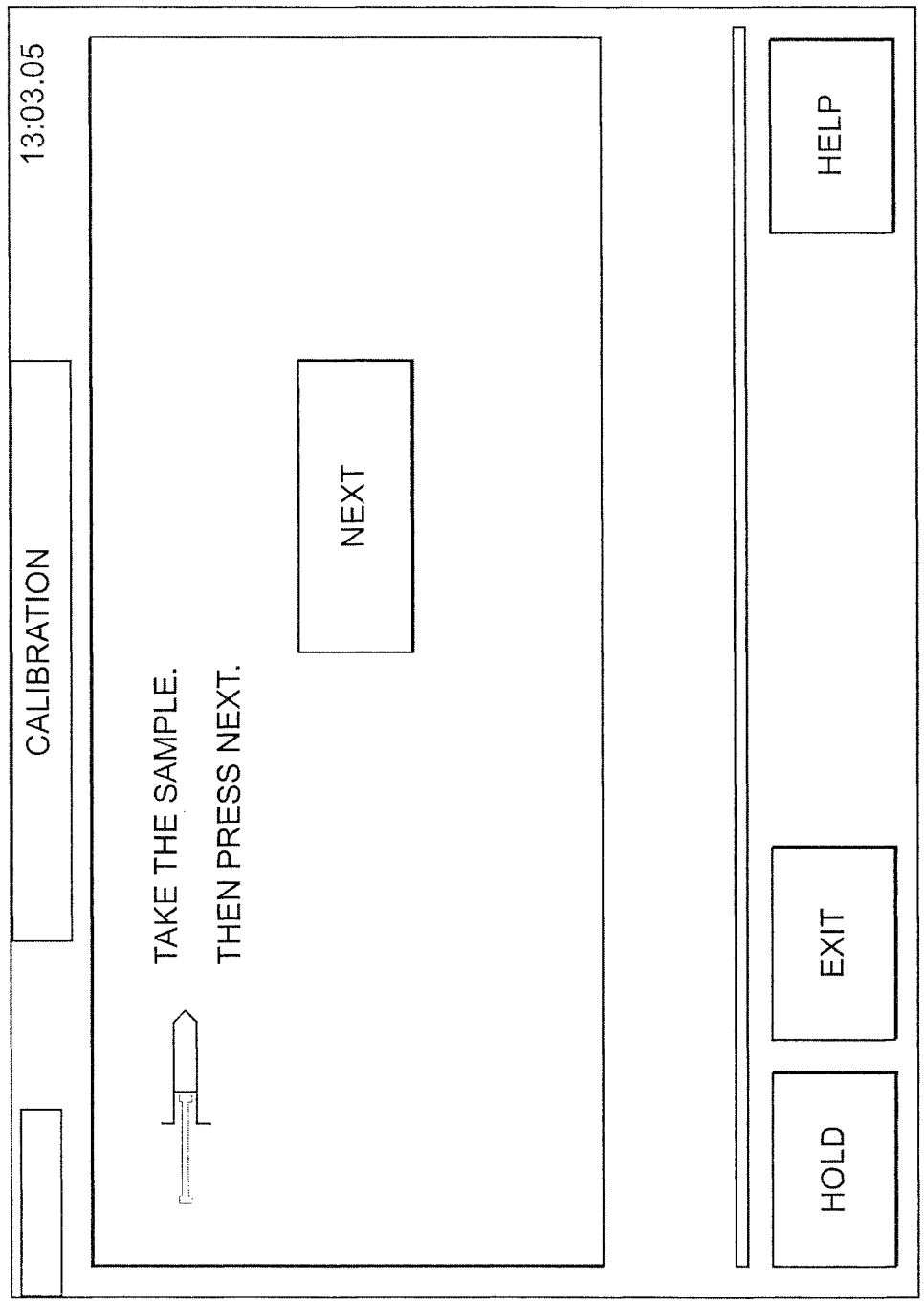

Referring to FIGS. 26-31, various views of touch display screen illustrate the different interactive steps during the control process of the apparatus of the present invention. FIG. 26 shows a system overview screen which highlights current conditions. FIG. 27 illustrates a run sequence screen which directs the operator through the culture process. FIG. 28 illustrates log data that the operator can review and that is available to build the batch record. FIG. 29 shows a method for inputting alpha-numeric data. FIGS. 30 and 31 show operator interaction screens to assist in operations (factor addition and pH probe calibration). On line help screens aid the operator for correct operation.

The apparatus of the present invention fully integrates the concept of disposable cultureware into automated process control for maintaining and expanding specialized cells (primary cells or cell lines) for a duration of any time needed. To accomplish this, the apparatus of the present invention was designed for EC space fluid flow that enhances cell growth in high density perfusion culture, yet remains completely closed and disposable. The integrated pre-assembled cultureware, which includes all tubing, bioreactor, oxygenator, and pH probe, is enclosed in a single unit that easily snaps into the apparatus. In addition to this error-proof, quick-load design, the entire cultureware unit enclosed by the casing becomes the cell culture incubator with temperature control regulated through automated process control of the instrument. Pumps and fluid control valves facilitate disposability and error-proof installation, eliminating the possibility of technician mistakes. Finally, during the course of any culture, the closed system can have restricted access except for trained and authorized personnel. For example, manipulations or sampling, outside of program parameters, can require password and identification code (e.g., bar code) access before they can be implemented.

Any host cells useful for production of the virus of interest can be used in the methods, apparatus, systems, and bioreactors of the invention. For example, Madin-Darby canine kidney (MDCK) cells are useful for the production of influenza virus. Other host cells include Vero cells, human diploid lung fibroblast cell lines (e.g., MRC-5 and WI-38), Per.C6 cells, 293 cells, duck embryonic retina (AGE1.CR) cells, FRhL2 cells. The host cells may be transformed or non-transformed cell lines, primary cells including somatic cells such as lymphocytes or other immune cells, chondrocytes, myocytes or myoblasts, epithelial cells and patient specific cells, primary or otherwise. Included also are cells or cell lines that have been genetically modified, such as both adult and embryonic stem cells. Host cells can be infected before or after the host cells are placed in the bioreactor. Preferably, the host cells (virus-infected, non-virus infected, or both) are placed in the bioreactor after it is loaded on the reusable instrumentation base device.

Optionally, various techniques can be utilized to reduce the concentration of molecules (e.g., proteins) in the EC space that are inhibitory to viral yield ("inhibitory molecules"). For example, these inhibitory molecules can be selectively diluted or removed from the EC space where the host cells and virus are grown. In single pass perfusion of the bioreactor, depending on the molecular weight (MW) cutoff, these inhibitory molecules could readily cross the fiber membrane of the bioreactor (via dialysis) into the IC space and be removed from the culture. This is the normal procedure used to provide fresh media and remove metabolic waste via the media feed pump. Fiber membranes with the necessary MW cutoff can be selected (e.g., 5K, 10K, 40K, 80K), and the pump rate can be increased or decreased to effectively control the concentration of these inhibitory molecules.

Figure 37:
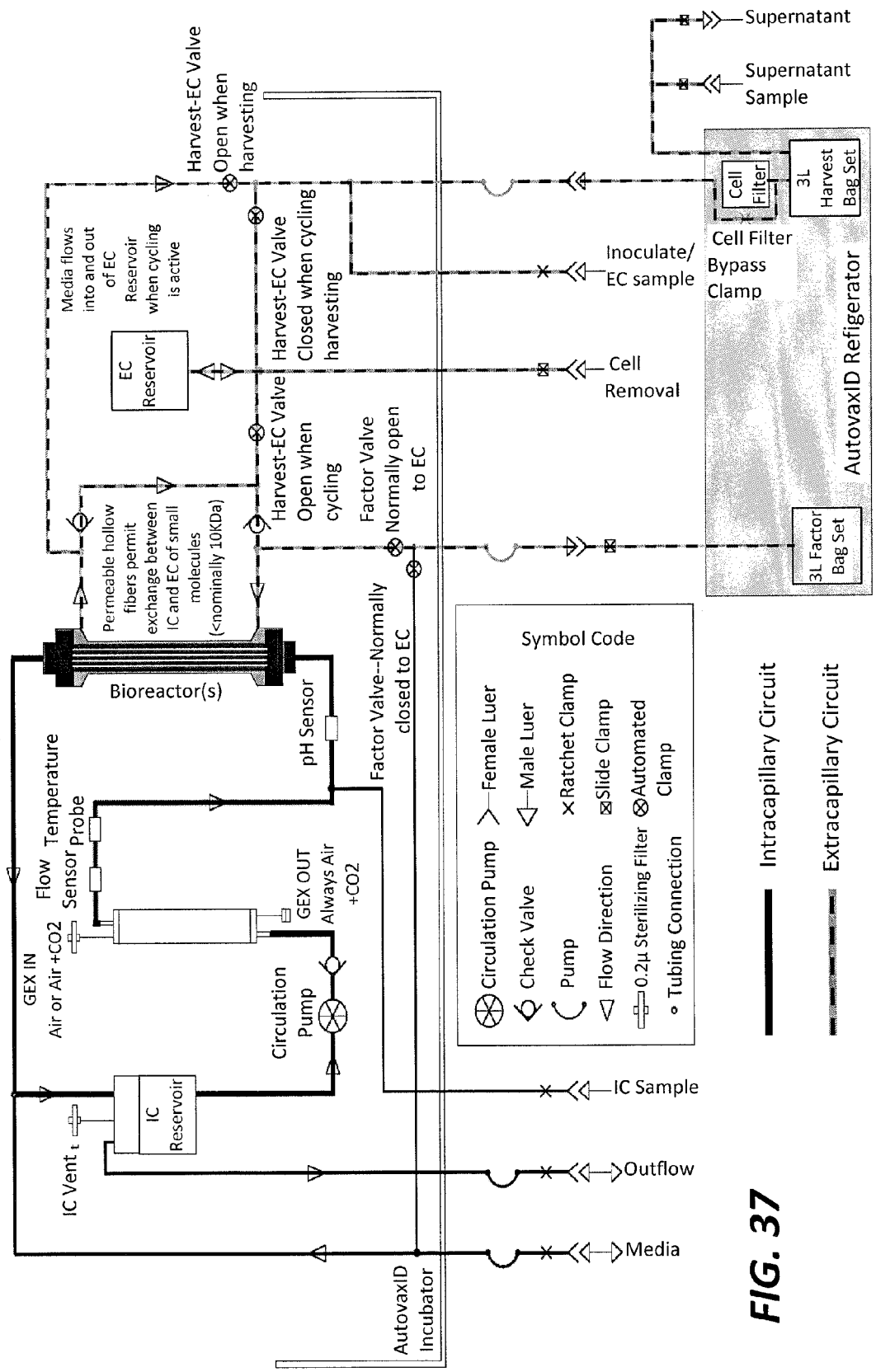

Another technique to minimize accumulation of inhibitory molecules is to use the harvest/factor pump (shown as pump on EC circuit in FIG. 37). This delivers and removes media from the EC side of the bioreactor. If the MW is too large for the inhibitory molecule to cross the fiber membrane into the IC space, increased or periodic removal of EC medium will remove product or these inhibitory molecules simultaneously. It may be desirable to supplement with additional protein (e.g., FBS) to offset the loss due to an increased harvest rate.

A third technique to reduce inhibitory molecules is to pass the harvest (EC side) or feed stream (IC side) media through a membrane filter (e.g., anion or cation exchange) to specifically bind the inhibitory molecule(s). By doing this, the media can then be recirculated through the bioreactor again until the metabolic waste reaches toxic levels. In this mode, the bioreactor would act as a compartment to house cells and the tank would house the basal media (essentially a large stirred tank with the cells confined to a small space). Also, depending on the size of the inhibitory molecules, tangential flow filtration can be used to remove inhibitory molecules based on MW. Again, it may be desirable supplement the media with protein and recirculate the media back through the bioreactor.

Yet another technique to dilute inhibitory molecules in the EC space is to increase the volume of the EC circuit itself, which may be achieved, for example, by increasing the size of the EC reservoir (FIG. 37) or adding one or more additional reservoirs to the EC circuit.

Of the aforementioned approaches, if the inhibitory molecule(s) do not cross the fiber membrane, the preferred approach is to use the harvest pump to increase the flow rate shortly after viral infection of the host cells, thereby preventing the concentration of inhibitory molecules in the EC space of the bioreactor from reaching a level that compromises virus yield (e.g., from reaching a level that signals apoptosis of the host cells).

Purification Unit

The purification unit of the invention is an automated apparatus for obtaining a purified biological product such as virus from a biological product-containing liquid medium (e.g., virus-containing liquid medium). The purification unit includes two individual parts: a reusable instrumentation base device (also referred to herein as a "second" reusable instrumentation base device, to distinguish it from the reusable instrumentation base device of the cell culture unit), and at least one disposable cell cultureware module that is used for a single production run and is disposable (also referred to herein as a "second" disposable cell cultureware module, to distinguish it from the at least one disposable cultureware of the cell culture unit).

The instrumentation base device of the purification unit provides the hardware to extract the fluid with the virus or VLP from the cell culture unit and process it. Preferably, an air detector checks the cultureware line which carries the fluid from the cell culture module 12 to determine when fluid is available to run through the selection device (e.g., a purification column and/or filter) and when no more fluid is available. Drives for a plurality of switching valves (e.g., nine switching valves) control the disposable valve portions to route fluids to complete the processes. Peristaltic pumps are used to move the fluids to accomplish the process. A fluid warmer can be used before the selection device to minimize out gassing in the selection device. An optical density detector is used in the process to determine when final product should be collected. The purification unit preferably relies on the cell culture unit for user interface and, optionally, communications with a facilities data management system. The purification apparatus and method described in International Publication No. WO 2005/090403, "Method and Apparatus for Protein Purification" (Gramer M. et al.), is hereby incorporated by reference in its entirety.

As is the case with the cultureware of the cell culture unit, the cultureware of the purification unit is for one-time use. The selection device (e.g., purification column and/or filter) and diafiltration module are loaded into the cultureware just before use. The reservoirs are filled at that time with the correct buffers for the product type. Optionally, that information can be tied to the cultureware's identifying code (e.g., bar code) in the facilities data management system when the operation is done and is used to verify the proper purification cultureware is loaded for the product that is to be purified. A plurality of disposable switch valves (e.g., nine disposable switch valves) is used to prepare the cultureware and route the fluids. Easy-load peristaltic pump cassettes are provided. A flow cell for measuring optical density is provided on the outlet of the selection device. A removable container holds the finished product (e.g., cell-derived product, such as virus). The pump cassettes and cultureware body are unloaded from the instrumentation base device of the purification unit and placed in a biohazard container for disposal.

The purification unit utilizes pre-sanitized or pre-sterilized disposable cultureware, such as a pre-sanitized or pre-sterilized disposable selection device, diafiltration module, liquid reservoirs, valves, tubing, and collection vessels, which can be packaged together for single use and then disposed of. Accordingly, the purification unit (also referred to as an Autovaxid Purification Module) is capable of concentrating (and preferably purifying) viruses in a highly efficient and contaminant-free manner. Specifically, the automated purification unit minimizes the need for operator intervention and provides a completely disposable flowpath to eliminate the need for cleaning and to eliminate the potential for cross-over contamination. Therefore, the purification unit is an automated apparatus for purifying viruses and VLPs in a less labor intensive manner compared to manual purification methods, thus, reducing purification time and increasing efficiency.

Figure 32:
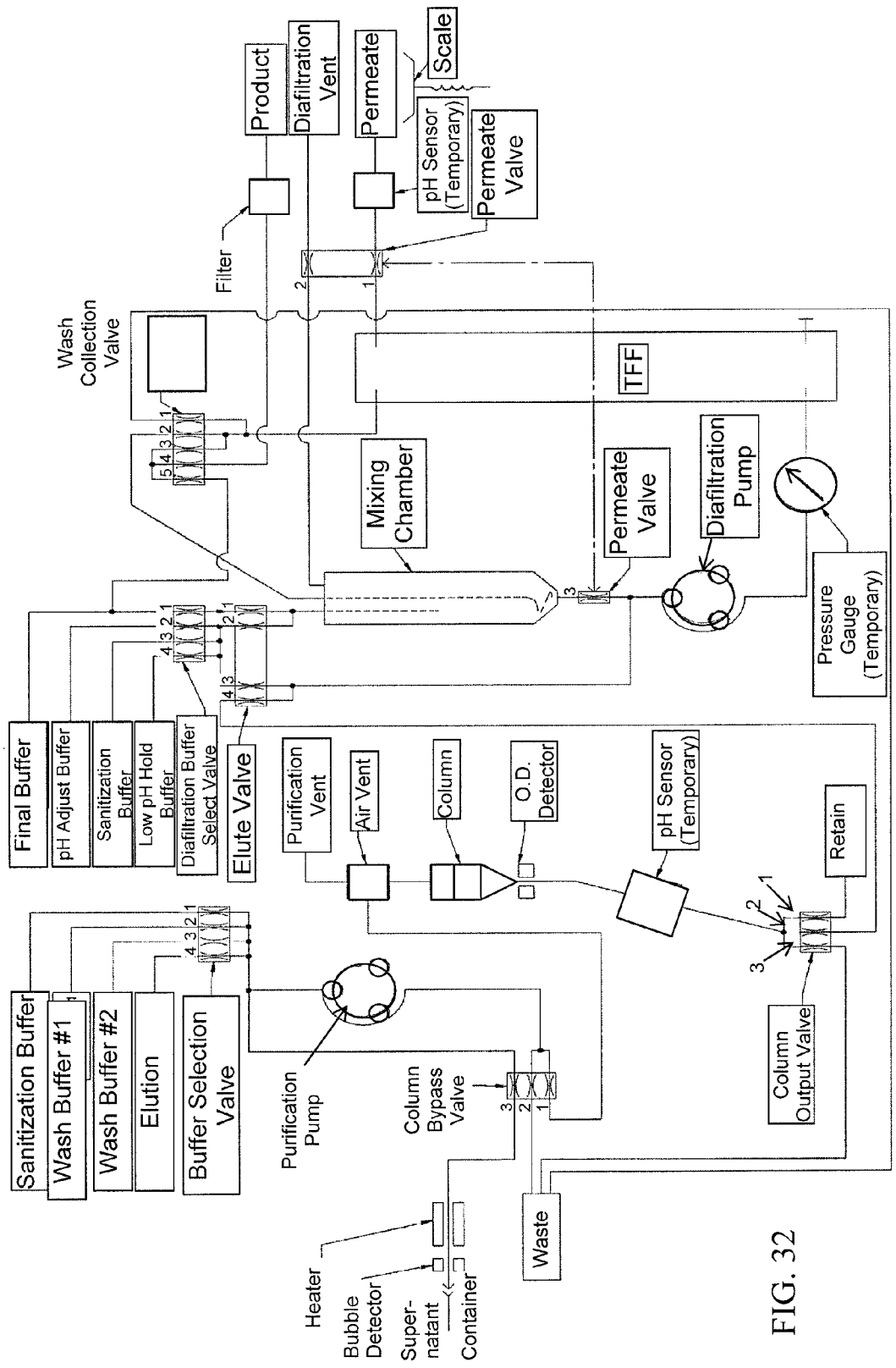
FIG. 32 shows a schematic representation of an embodiment of the purification unit, wherein the selection device (e.g., an affinity column) and the diafiltration module of the purification unit are connected to multiple liquid reservoirs. The reservoirs each contain liquid, such as a wash buffers and an elution buffer for delivery to the selection device and acidic, basic and final buffer solutions for delivery to the diafiltration module. Elution of the purified virus from the selection device can be aided by a photometer. The apparatus further includes a device for flowing liquid from the reservoirs into the selection device or into the diafiltration module, for example, valves and tubing which connect the reservoirs to the selection device or to the diafiltration module. The flow of the liquid is diverted by valves which transfers the eluted virus-containing solution from the selection device to the diafiltration module and then to the pre-sterilized removable collection vessel (also referred to herein as the second cultureware module).

In one embodiment, the purification unit has the configuration shown schematically in FIG. 32. The purification unit comprises a pre-sanitized or pre-sterilized, disposable cultureware module, as discussed above. With reference to the embodiment in FIG. 32, the cultureware module includes, a selection device (a column), a diafiltration module, multiple liquid reservoirs, a device for flowing liquid from the reservoirs and into the selection device and the diafiltration module, a device (e.g., a valve) for diverting the effluent from the selection device and the diafiltration module, e.g., at least two reservoirs. The cultureware module of the purification unit is capable of being installed into the instrumentation base device via a single motion or "snap-on" or "quick-load" technique and comprises mechanical and electrical interfaces for communicating with the instrumentation base device.

In the diafiltration loop (mixing chamber, pump, pressure gauge and TFF cartridge), there is a volume of fluid. Because of the physical characteristics of the TFF cartridge, molecules above a certain size are retained in the loop, smaller molecules can flow (permeate) across the fiber and out the permeate port of the TFF device. Pressure on the loop side determines rate of flow across the membrane for a specific membrane. Pressure is generated by flowing fluid through the TFF and/or restricting the outlet tubing of the TFF device returning fluid to the mixing chamber. Because the TFF loop is a closed loop, permeating fluid causes a negative pressure in the head space of the mixing chamber. This provides the hydrostatic pressure needed to draw fluid from the selected buffer bag to make up the volume. Due to the small volume in the loop it is efficient at buffer exchange (it takes less fluid to get to a desired concentration or reduction than dialysis).

Permeate of diafiltration may be monitored by weighing collected permeate fluid. The permeate rate for a given pressure will change over the course of the diafiltration due to membrane fouling. With that in mind, by observing the amount of fluid that has permeated from the loop, an accurate prediction of the loop concentration can be made. Since it is easier to measure weight than volume aseptically and knowing 1 gram of fluid is approximately 1 ml, incorporating a scale system ("scale" in FIG. 32) which captures the permeate is a viable system for controlling the buffer exchange process. As an example, if a buffer exchange is desired that will reduce the current buffer to 2% of the original concentration with a different buffer in a 20 ml loop volume, permeating 100 ml while adding the new buffer would provide the desired result (exchanging 5 loop volumes).

In a particular embodiment, the selection device, e.g., the affinity column, and the diafiltration module of the purification unit are connected to multiple liquid reservoirs. The reservoirs each contain liquid, such as a wash buffer, an elution buffer, or a neutralization solution, for delivery to the selection device or the diafiltration module. Accordingly, the purification unit further includes pre-sanitized or pre-sterilized device for flowing liquid from the reservoirs into the selection device, for example, pre-sterilized valves and tubing which connect the reservoirs to the selection device. The valves and tubing may allow liquid from only one reservoir at a time to pass through the selection device. Alternatively, the valves and tubing allow for liquid from more than one reservoir to pass through the selection device.

In a particular embodiment, the purification unit includes a pre-sanitized or pre-sterilized device (e.g., a valve) for diverting the effluent from the selection device into the diafiltration module or into a waste container. Similarly, the purification unit includes a pre-sanitized or pre-sterilized device for diverting the effluent from the diafiltration module into the pre-sterilized collection vessel or into a waste container.

In one embodiment, the purification method of the invention begins with the automated step of loading a virus-containing medium (e.g., a virus-containing fluid such as aqueous liquid), onto a pre-sanitized, preferably a pre-sterilized, disposable selection device to absorb the virus onto the selection device. The selection device for use in the present apparatus and method can include, for example, a column packed with a chromatography resin, such as an affinity resin, a cation exchange resin, an anion exchange resin, a metal affinity resin, a hydrophobic interaction resin, multi-modal chromatography resin or some other type of resin capable of chromatographic separation of the virus. Another selection method can include membrane based chromatography, for example, a membrane treated with a chromatography chemistry (a chromatrographic ligand), such as an affinity ligand, a cation exchange ligand, an anion exchange ligand, a metal affinity ligand, a hydrophobic interaction ligand, multi-modal chromatography ligand or some other type of ligand capable of chromatographic separation. In another embodiment, the virus-containing medium and the selection device can be pre-treated prior to loading. For example, the virus-containing medium can be automatically heated and degassed before loading. The selection device can be washed, pre-eluted, and/or pre-neutralized prior to loading.

In those embodiments in which the selection device is a chromatography device, any chromatrography media having surface chemistries capable of capturing the product may be used. Traditional chromatography methods use columns packed with porous particles, which may be used in the invention; however, the architecture of the chromatography is not critical. For example, the chromatography media may be a membrane, monolith, or porous particles.

In some embodiments, the selection device is a chromatography column or filter having a natural or synthetic hydroxyapatite matrix (e.g., ceramic hydroxyapatite). Hydroxyapatite is a naturally occurring mineral form of calcium apatite. Hydroxyapatite is the hydroxyl end member of the complex apatite group. The OH— ion can be replaced by fluoride, chloride or carbonate. It crystallizes in the hexagonal crystal system. Hydroxyapatite can be used in chromatography for purification. The mechanism of hydroxyapatite chromatography is somewhat complicated and has been described as "mixed-mode" ion exchange. It involves nonspecific interactions between positively charged calcium ions and negatively charged phosphate ions on the stationary phase hydroxyapatite resin with protein negatively charged carboxyl groups and positively charged amino groups. For elution, a buffer with increasing phosphate concentration is typically used. Hydroxyapatite that can be used to pack columns and filters for chromatography includes natural hydroxyapatite and synthetic hydroxyapatite (e.g., crystalline hydroxyapatite, ceramic hydroxyapatite). Thus, in some embodiments of the purification method of the present invention, solution containing desired virus can be purified by a hydroxyapatite column or filter, wherein the hydroxyapatite column or filter is packed with natural hydroxyapatite or synthetic hydroxyapatite. In some embodiments, the synthetic hydroxyapatite is crystalline hydroxyapatite or ceramic hydroxyapatite.

In some embodiments, the selection device utilizes an orthogonal process design having distinct separation mechanisms. For example, a two-step process that contains one fractionation step based on product size and another on product charge, or a process with one step based on product charge and another on hydrophobicity could be utilized. In orthogonal process design, the purification capability of any one step is measurable only within the context of its potential partner(s).

After loading, the selection device is typically washed to remove residual contaminants contained within the aqueous medium, such as residual proteins from host cells used to produce the virus to be purified, e.g., host cell proteins, nucleic acids and endotoxins.

After washing, the bound virus is then eluted into an aqueous medium. The step of eluting can be accomplished, for example, by either changing the pH, buffer components, or the salt concentration of the medium which is loaded onto the selection device. For example, a phosphate solution can be added to the selection device to produce a virus-containing phosphate buffered eluate. An example of an appropriate acidic solution for eluting includes a solution of approximately 0.05 to 0.5 M of sodium phosphate at a pH of about 5 to 8. Alternatively, the step of eluting can include adding a solution to the selection device which alters the salt concentration of the medium loaded onto the selection device. In one embodiment, the step of eluting the virus is facilitated by the use of a photometer.

Optionally, the purification method of the invention includes a filtration step to remove cellular debris prior to controlled temperature storage or before loading on the selection device.

Upon eluting the virus into an aqueous medium, the eluted purified virus can be automatically deposited into a pre-sterilized, disposable collection vessel and removed from the automated purification apparatus. Alternatively, the eluted purified virus can undergo further automated processing.

In another embodiment, the virus-containing acidic solution is then neutralized by transferring it to a basic solution, for example, by diafiltering against a basic solution (e.g., a solution of approximately 10 mM citrate at a pH of about 5 to 7).

In another embodiment, the virus-containing final buffer solution can be further purified, for example, by filtering the solution, for example, filtering it through a filter having a pore size of approximately 0.22 µm.

In another embodiment, the method of the invention further includes the step of conjugating the purified virus to a carrier molecule, such as an adjuvant. Accordingly, the present invention can be used to produce a variety of vaccines. In a particular embodiment, the invention provides a method for producing a human influenza vaccine.

The purification unit is an automated apparatus for purifying a virus or VLP from a cell product-containing medium (e.g., an aqueous liquid), comprising at least one pre-sanitized or pre-sterilized, disposable cultureware module attached to an automated instrumentation base device for controlling liquid flow through the cultureware module. For example, the pre-sanitized or pre-sterilized, disposable cultureware module includes a selection device; multiple, liquid reservoirs; a device for flowing liquid from the reservoirs and into the selection device; a device for diverting the effluent from the selection device; and a container for collecting effluent from the selection device. The pre-sanitized or pre-sterilized, disposable cultureware module can further include a diafiltration module; a device for flowing liquid from the reservoirs and into the diafiltration module; a device for flowing liquid between the selection device and the diafiltration module; a device for diverting the effluent from the diafiltration module; and a container for collecting effluent from the diafiltration module, e.g., at least two disposable reservoirs.

In a particular embodiment, the device for flowing liquid (such as, wash buffer, elution buffer, or neutralization solution) into the selection device or diafiltration module includes a series of pre-sanitized or pre-sterilized, disposable valves and tubing which connect the reservoirs to the selection device or diafiltration module and which allow liquid from only one reservoir at a time to pass through the selection device or diafiltration module. Alternatively, the valves and tubing which connect the reservoirs to the selection device and diafiltration module allow liquid from more than one reservoir at a time to pass through the selection device.

In one embodiment, the valve includes a disposable outer body through which flexible tubing is threaded. A cammed shaft is mated with the body and a motor drives the shaft to open and close the tubing. Multiple tubing lines can be controlled by one motor/shaft. The pre-sanitized or pre-sterilized tubing lines contain the fluid and maintain sterility. The tubing and outer body housing are disposed of at the end of use.

In another embodiment, the purification unit includes a sensor for monitoring the effluent from the selection device or diafiltration module, such as a probe for measuring the pH, absorbance at a particular wavelength, or conductivity of the effluent.

The pre-sanitized or pre-sterilized, disposable selection device is chosen according to the particular type of purification method used, such as immuno-affinity chromatography, affinity chromatography, ionic exchange chromatography, hydrophobic interaction chromatography, or size exclusion chromatography. Suitable selection devices for these types of purification processes are well known in the art including, for example, an affinity column packed with an anti-IgM resin, a Protein A, a Protein G, or an anti-IgG resin, an ion exchange column containing a charged particle (matrix) which binds reversibly to particular virus (e.g., a Sartorious Q75 anion exchange filter), a column packed with a hydrophobic absorbent, such as cellulose, cross-linked dextrose (Sephadex), or a column containing cross-linked polystyrene with pores of varying sizes.

In a particular embodiment, the selection device comprises a pre-sterilized affinity purification column, e.g., a column approximately 1.5 to 2.5×10 cm in length which is pre-packed with approximately 4 ml to 50 ml of resin, such as an affinity ligand (binding substance), such as Protein A, Protein A analogs, Protein G, anti-IgG or anti-IgM resin. Affinity chromatography (AC) is a technique enabling purification of virus with respect to biological function or individual chemical structure. The substance to be purified is specifically and reversibly adsorbed to a ligand which is immobilized by a covalent bond to a chromatographic bed material (matrix). Samples are applied under favorable conditions for their specific binding to the ligand. Substances of interest are consequently bound to the ligand while unbound substances are washed away. Recovery of molecules of interest can be achieved by changing experimental conditions to favor desorption.

Purification of various virus types is also encompassed by the invention, including animal (including human), bacterial, archaea, fungal and plant viruses. Various classifications of viruses my be produced with the invention including ssDNA, dsDNA, dsRNA, (+)ssRNA, (−)ssRNA, ssRNA-RT and dsRNA-RT viruses. The viruses and VLP can be isolated from a number of sources, including without limitation, serum of immunized animals, ascites fluid, hybridoma or myeloma supernatants, conditioned media derived from culturing a recombinant cell line that expresses the virus and from all cell extracts of virus producing cells.

A purified virus or VLP of the present invention is substantially free from host cell contaminants such as host cell proteins, nucleic acids and endotoxins.

In a particular embodiment of the invention, the automated method involves purifying a virus or VLP using the steps outlined in Example 2 and the purification unit as represented schematically in FIG. 32. Specifically, prior to loading the virus-containing medium, the selection device is equilibrated. The selection device can be washed with liquid stored in the liquid reservoirs which are connected to the selection device with pre-sanitized valves and tubing. For example, the selection device can be washed with phosphate buffer saline (PBS) or a neutral buffer at a pH of about 7.3 to remove impurities, such as preservatives found in the pre-packed, pre-sterilized, disposable column. The size and type of the column may vary based on the type of virus being purified The virus-containing medium or supernatant is then loaded onto the pre-sterilized, disposable selection device. This can be done after adjusting the supernatant or, more preferably, is done without adjusting the supernatant. The appropriate rate for loading can be determined as is known in the art.

In a particular embodiment, the medium is heated and/or degassed prior to loading to reduce or eliminate the amount of dissolved gas which can accumulate in the separation device and hinder its ability to bind virus or VLPs. For example, the virus-containing medium can be heated to about room temperature and degassed.

Once loaded, the selection device can be washed with a wash solution that is stored in a liquid reservoir to remove any residual contaminants contained in the medium, such as residual proteins from the host cells which were used to produce the virus to be purified, e.g., contaminants such as host cell proteins, nucleic acids and endotoxins. The appropriate volume and solution for removing contaminants can be determined as is known in the art. In a particular embodiment, the column is washed using a buffer, such as PBS, until the ultraviolet (UV) absorbance of the effluent is about zero as measured using standard photometric procedures.

The virus is then eluted, for example, by using an increase in salt concentration, thereby producing a virus-containing acidic eluate. In another embodiment, the salt concentration of the loaded column is changed. To elute by changing the salt concentration of the loaded column, an elution buffer can be added, such as an elution buffer containing approximately 0.05 to 1.5 M of salt and at a pH of about 5.0 to 8.0. The appropriate volume and rate of the elution buffer can be determined by one of ordinary skill in the art. In a particular embodiment, the elution buffer is added to the column at approximately 1.0 to 2.0 ml/min for a total of about four (4) column volumes. Further, the type of elution buffer depends on the type of virus to be purified and can also be determined based on the techniques known in the art. For example, for purification of a human influenza virus, the elution buffer may comprise approximately 1.5 M NaCl at about pH 7.3. Those of ordinary skill in the art can determine the optimum molarity and pH based on the ranges and teachings provided herein.

In a particular embodiment, the elution of the purified virus from the selection device can be aided by a monitoring device. For example, the absorbance at a particular wavelength of the eluate can be monitored using a photometer to determine the appropriate concentration of the eluate. Methods for eluting viruses by using a photometer are well known in the art. Generally, collection of the peaks containing the purified virus begins when the ultraviolet (UV) absorbance of the eluate begins to increase from baseline (zero). Collection continues until the UV absorbance returns to its baseline. In a particular embodiment, the volume of the peak fractions collected is about 10 to 25 ml and the peaks are collected in a pre-sanitized or pre-sterilized, reservoir contained within the purification apparatus.

Following elution, the purified biological product (e.g., virus) can be collected in a pre-sterilized, disposable collection vessel and removed from the purification unit.

In an additional embodiment, the biological product (e.g., virus) contained in the buffer solution is flows through a chromatography column, for example, an anion exchange column, while impurities such as host cell proteins and host cell DNA remain bound to the column. The purified virus is automatically collected into a pre-sterilized collection vessel and removed from the automated purification apparatus.

In another embodiment, the purified biological product (e.g., virus) is transferred into an appropriate buffer, such as phosphate buffered saline, pH 7.4. In a particular embodiment, enough volume is used so that the buffer exchange efficiency is theoretically greater than or equal to about 99.5%.

In an additional embodiment, the biological product (e.g., virus) contained in the final buffer solution is filtered through a filter, for example, a filter having a pore size of approximately 0.22 µm. The purified virus is automatically deposited into a pre-sterilized collection vessel and removed from the automated purification apparatus. In a particular embodiment, the purified biological product (such as virus) is stored in a solution containing approximately 0.2-0.9% saline or further processed.

In another embodiment, the step of transferring the eluted virus to different solutions occurs automatically using a pre-sterilized diafiltration module. Diafiltration is the fractionation process that washes smaller molecules through a membrane and keeps molecules of interest in the retentate. Diafiltration can be used to remove salts or exchange buffers. In discontinuous diafiltration, the solution is concentrated, and the lost volume is replaced by new buffer. Concentrating a sample to half its volume and adding new buffer four times can remove over 96% of the salt. In continuous diafiltration, the sample volume is maintained by the inflow of new buffer while the salt and old buffer is removed. Greater than 99% of the salt can be removed by adding up to seven volumes of new buffer during continuous diafiltration. In a particular embodiment, the diafiltration module contains a filtration membrane of approximately 50 $cm^2$ areas having a nominal pore size of 0.1 micron. Specifically, the diafiltration module is used to further purify the virus and uses the tangential flow filtration principle whereby molecules greater than 0.1 micron in diameter (e.g., the virus,) cannot pass through the membrane but small molecules, such as buffers and non-infections viral fragments, and host cell proteins, can pass through. Accordingly, the diafiltration module is used to exchange one buffer for another and is a more efficient substitute for dialysis.

In a particular embodiment, the diafiltration module is sterilized using a solution containing approximately 0.1 N sodium hydroxide at a crossflow or feed rate of approximately 20-40 mL/min. This crossflow rate is maintained throughout the process. The 0.1 N sodium hydroxide is flushed out of the system using a solution containing phosphate buffered saline at pH 7.4. After sanitization is complete, the virus-containing solution that is eluted from the selection device is introduced into the diafiltration module.

In a particular embodiment, the present invention provides an automated method of producing a vaccine by purifying a virus, inactivating the virus before or after harvest, and conjugating the virus to an adjuvant.

Examples of adjuvants include, for example, keyhole limpet hemocyanin (KLH), bovine serum albumin, (BSA), and $\beta_2$-glycoprotein I. Other albumins such as ovalbumin, mouse serum albumin or rabbit serum albumin can also be used as adjuvants, as well as bovine gamma globulin or diphtheria toxoid.

KLH is a respiratory protein found in mollusks. Its large size (M.W. $8-9 \times 10^6$ Da) makes it very immunogenic and the large number of lysine residues available for conjugation make it very useful as a carrier for haptens. The phylogenic separation between mammals and mollusks increases the immunogenicity and reduces the risk of cross-reactivity between antibodies against the KLH carrier and naturally occurring proteins in mammalian samples. KLH is obtainable both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten. Protocols for conjugating haptens to carrier proteins may be found in *Antibodies: A Laboratory Manual*, E. Harlow and D. Lane, ed., Cold Spring Harbor Laboratory (Cold Spring Harbor, N.Y., 1988) pp. 78-87.

Accordingly, in some embodiments, the invention provides an automated method of producing a vaccine by purifying a virus or VLP and combining the virus or VLP with an adjuvant and/or pharmaceutically acceptable carrier. Optionally, the virus or VLP can be conjugated to a carrier molecule and/or adjuvant. In general, conjugation is achieved by mixing the purified virus and the carrier or adjuvant with an appropriate catalyst under the appropriate conditions.

The purification method and apparatus of the present invention can be used in conjunction to provide a fully automated and integrated method for purifying virus and virus-like particles (VLPs).

Conventionally, each unique cell line must be cultured, virus harvested, and purified separately. In order to manage production of large amounts of viral vaccines, a considerable number of instruments and space would be needed. Compactness of the design and the amount of ancillary support resources needed become an important facilities issue. Small stirred tank systems require a device for steam generation and distribution (for steam-in-place sterilization) or autoclaves to sterilize the vessels and supporting plumbing. To support a large number of units becomes a logistics problem for the facility. The system of the present invention has no such requirement. Larger scale cell culture is historically done in segregated steps that often require separate types of equipment. Manual handling, storage and tracking is needed for all these steps as the culture expands and product is harvested. The method of the present invention integrates these steps into a continuous, fully integrated sequential process. This eliminates the handling risk that is always a concern with viruses and facilitates the data gathering required for thorough documentation of the entire process.

Each hollow fiber bioreactor is a single dialysis module. By "single dialysis module" is meant one unit or structure through which dialysis is performed. A dialysis module generally comprises an open-ended bundle of hollow fiber membrane potted in a tubular housing to create two distinct flow chambers, lumen and extracapillary, each with inlet and outlet port access. A semi-permeable hollow fiber membrane separates the two chambers and selectively permits passage based on size and concentration gradient of solutes while restricting other solutes from passing between the 2 chambers. By operating the module in a counter-current flow mode, the solutes passing through the membrane are quickly swept away and diluted into a large volume of dialysate solution ("sweep"), maintaining the largest concentration gradient possible. Accordingly, dialysis may be performed in a single pass sweep through a single dialysis module.

The present invention is further illustrated by the following examples which should not be construed as further limiting.

MATERIALS AND METHODS

Cell Preparation.

Bioreactor adapted Madin-Darby Canine Kidney (MDCK) cells were grown in the presence or absence of fetal bovine serum in T-150 culture flasks and harvested at 80% confluency. $1 \times 10^8$ cells were added to a Biovest HF Primer unit through the EC portal and allowed to attach to the outside of the hollow fiber membrane. Medium was continuously circulated through the bioreactor for 14 days until the total cell number reached approximately $1 \times 10^9$ cells. On day 13, a separate flask of MDCK cells was infected with Influenza A/Mexico/4108/2009 H1N1. The following day the influenza virus-infected cells were collected, permeabilized, treated with a fluorochrome-labeled monoclonal antibody to the influenza A virus nucleocapsid antigen and the number of antigen positive cells was counted using an fluorescent microscope.

Virus Growth.

Subsequent to cell preparation, one hundred virus-infected MDCK cells were then introduced into the EC space (ECS) of the bioreactor containing $10^9$ uninfected MDCK cells. For the duration of this study, the bioreactor was maintained with continual medium perfusion in an incubator at 37° C. with 5% $CO_2$ atmosphere. To determine the rate of virus growth, samples (0.5 mL) were collected from the ECS at 24 hour intervals post infection (PI) and assayed for infectious virus.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Production of Influenza Virus Using Hollow Fiber Bioreactor

Figure 34:
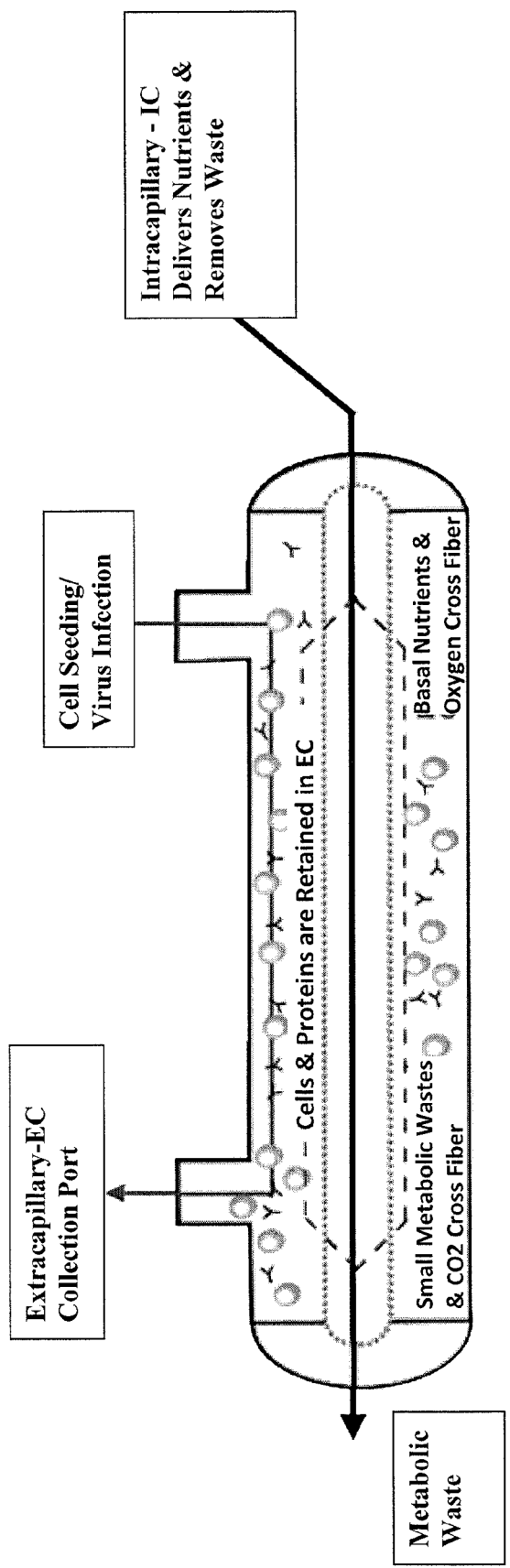
FIG. 34 shows an embodiment of a hollow fiber perfusion bioreactor (HGBx), which may be used for virus production.
Figure 35A:
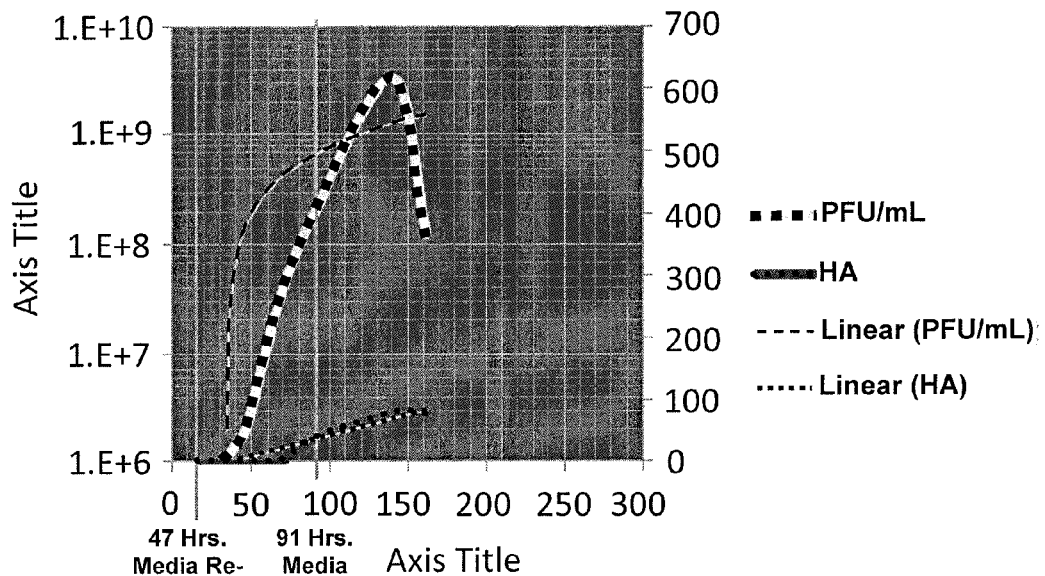
FIGS. 35A and 35B show, respectively, infectious virus (plaque forming units) and viral nucleic acid (PCR). No genetic mutation in HA was observed at any point post infection (data not shown).
Figure 35B:
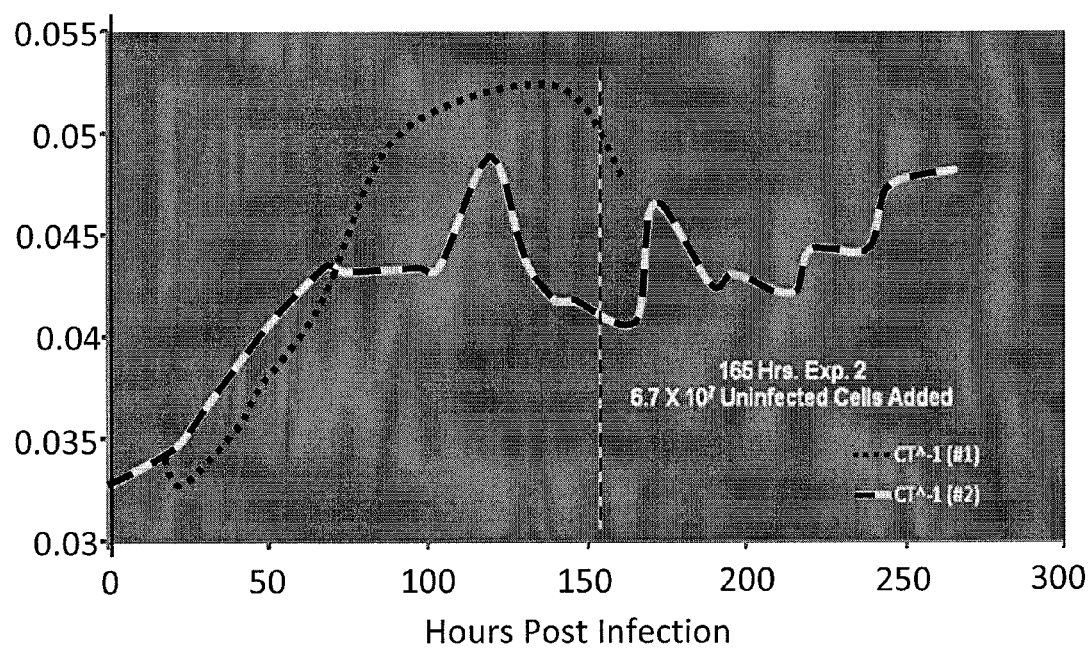
Figure 36:
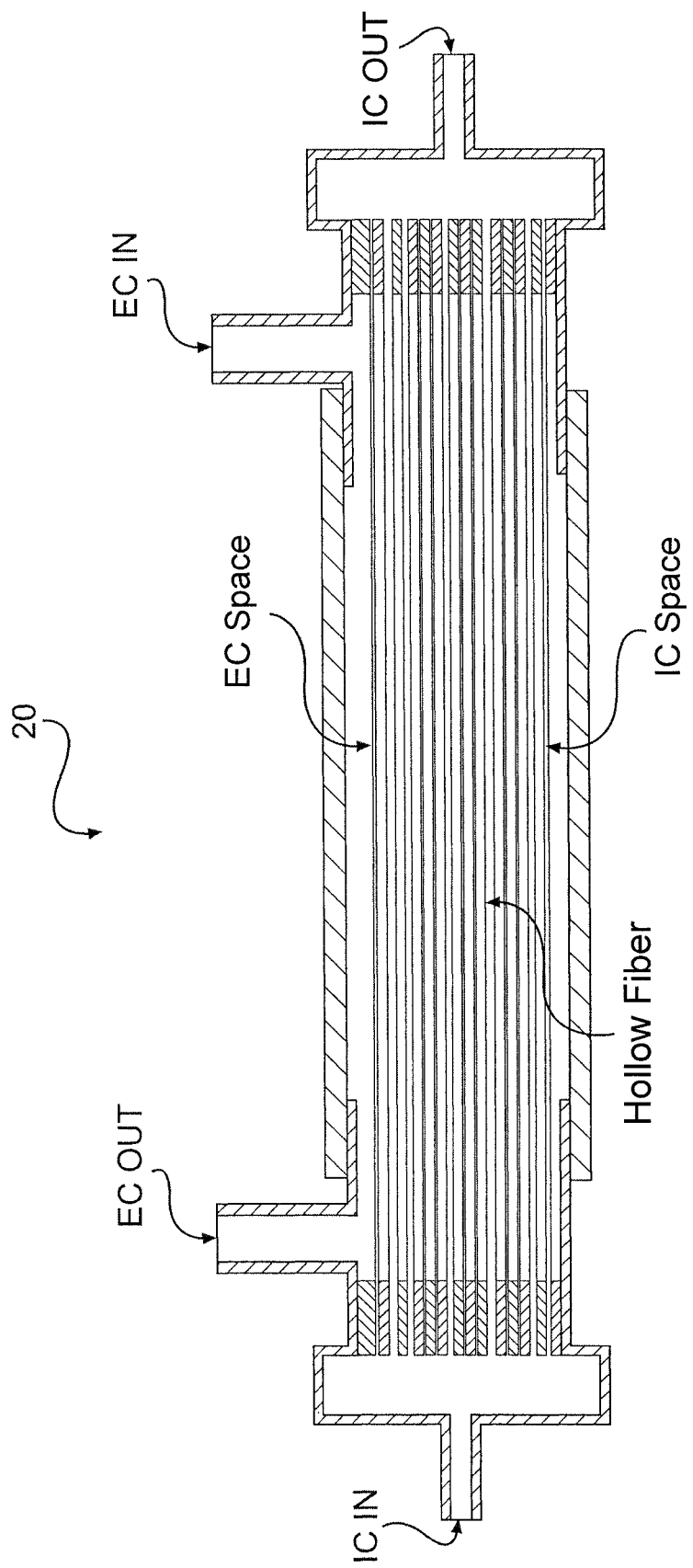
FIG. 36 shows an embodiment of a hollow fiber perfusion bioreactor of the AutovaxID instrument, with hollow fibers and in and out ports for the intracapillary space and extracapillary space indicated, which may be used for virus production. As will be appreciated by those skilled in the art, the sidedness and orientation for production of the virus at a yield greater than that achieved in the absence of such regulation. The EC circuit, which includes the EC space of the bioreactor, and the IC circuit, which includes the IC space of the bioreactor, are indicated in FIG. 37. One or more types of inhibitory molecules can be regulated within the EC space where the virus-infected host cells are cultured by, for example; and diluting one or more inhibitory molecules in the EC space by adding cell culture medium to the EC space and controlling how fast culture media bearing the inhibitory molecule is replaced with fresh culture media in the EC space, or by diffusing one or more inhibitory molecules from the EC space, through the fiber membrane, into the intracapillary (IC) space.

A key benefit of hollow fiber bioreactor technology is the high cell density attained ($>10^8$/ml) through the use of continuous media perfusion for feeding the cells and removal of toxic wastes. These bioreactors are composed of semi-permeable hollow fibers, typically in a parallel array housed within a plastic (e.g., polycarbonate) casing or shell (FIG. 34). There are two compartments within a HFBx: the intracapillary (IC) space within the hollow fibers (lumen) and the extracapillary (EC) space surrounding the hollow fibers. The total volume within the shell that surrounds the fibers (EC space) depends on the size of the HFBx. Typically, cells are seeded into the bioreactor EC space through a port on the top of the HFBx. Fresh medium is continually pumped through the lumen of the fibers. As the cell population expands, this medium feed rate is steadily increased to deliver nutrients to the cells and remove metabolic waste. Depending on the average pore size of the semi-permeable hollow fiber membrane, larger molecular weight (MW) components, such as secreted protein (>10 KD) or viruses, will be restricted from crossing from the EC space into the IC space. Thus, concentrated product is typically harvested from the EC space at a steady rate for the duration of the culture. Hollow fibers can be constructed from cellulosic, polysulfone, polypropylene, polyethylene, or other materials, depending on the characteristics needed for optimal protein or virus production. The vast majority of HFBx utilize cellulosic fibers for uniform cell expansion and production of mammalian cell-secreted products.

Hollow fiber bioreactors provide several fundamental advantages not found in other reactor systems currently used in virus production:
1. Growth of anchorage-dependent and suspension cells at physiologic densities ($>10^8$ cells/mL) for extended periods of time (months);
2. Continual perfusion to promote normal cell function and 3D interactions that cells normally experience in vivo, allowing for a more natural virus infection cycle;
3. Nutrient supply (sugars, amino acids, oxygen, etc.) at least as fast as cellular consumption requires and removal of metabolic waste products (lactic acid, ammonia, etc.) at a rate that prevents toxic build-up;
4. Removal or dilution of harmful cytokines and virus coded host shut-off proteins to avoid premature apoptosis; and
5. Reduced labor requirements and user interactions;
6. Virus containment in a small footprint for adaptation to biosafety level 2 (BSL-2) and biosafety level 3 (BSL-3) facilities.

The threat of pandemic and avian influenza virus outbreaks and the need for vaccine preparedness to control these outbreaks has elevated interest in new production platforms for vaccine production that are less costly and cumbersome than current technologies. In this regard, embryonated hen's-egg-based vaccines are now disappearing in favor of mammalian cell-based vaccines, which, while more convenient and safer than egg-based vaccines, add another level of complexity to the manufacturing process.

Facing the probability of pandemic outbreaks of influenza virus and the world-wide costs related to annual human influenza A epidemics, there is a need for new flexible and modular reactors that can improve vaccine production capacity. The inventors wished to test the hypothesis that hollow fiber bioreactors could be used as an effective and relatively inexpensive production platform for rapid and cost-effective large scale propagation of pandemic influenza virus isolates. To this end, the Biovest HF Primer™ was selected for these studies. The Primer is a small HFBx designed specifically for R&D of processes that are directly scalable to the larger, more automated HFBx systems.

Results

FIGS. 35A and 36B illustrate the amount of infectious (plaque forming) virus and genomic equivalents observed at each time point PI. Note that at 140 hours post infection, virus titers reached $3\times10^9$ infectious units per mL as determined by a plaque assay. As with most influenza isolates, there are approximately 10-100 non-infectious particles for every infectious unit; thus, the inventors believe that the total particle count was approximately $3\times10^{10}$-$3\times10^{11}$.

While the Biovest HF Primer is useful for experimental needs, more sophisticated, automated, and higher production capacity units, such as the AutovaxID instrument, are needed for large-scale virus production. Since this system is functionally closed, yet automates mammalian cell processes, it is deal for the production of viruses or cell-secreted proteins. A combination of pore size selection and control of the fluid dynamics within the bioreactor encourages removal of harmful cytokines and virus-induced host shutoff proteins, while maintaining virus stability. Furthermore, the unique two-component design of the AutovaxID provides containment that minimizes the need for traditional clean rooms, greatly reduces the risk of process contamination, and provides a small footprint that facilitates adaptation to existing BSL-2 or BLS-3 facilities.

AutovaxID is an example of how advanced hollow fiber technology can play an integral role in the manufacture of vaccines. In comparison to error-prone manual techniques or minimally-customizable large-tank systems, the AutovaxID is:

cGMP compliant and compact to minimize size requirements for manufacturing facilities;
Composed of disposable elements for all product contact components to maximize speed and manufacturing flexibility;
Self-contained, or functionally closed for avoidance of contamination and containment of infectious agents;
Automated to reduce operator intervention and expertise/skill levels; and
Designed to regulate perfusion rates for control of culture environments to enhance virus replication and stability.

Hollow fiber bioreactors offer a compact, highly efficient, scalable and economical method for virus and VLP production. The combination of an unlimited nutrient supply and the ability to de-bulk the culture through the cartridge ports allows the system to be maintained at relative equilibrium for extended periods. This continuous production over long periods of time, rather than the batch-style approach of other systems, provide several benefits, including: consistency in culture conditions; dramatically increased production per unit footprint and culture volume; continuous or daily product harvest allowing timely and convenient stabilizing treatment for collection and storage; and capability of selective dilution or removal of products from the culture that might be toxic or inhibitory to cells and/or viral yield.

Various techniques can be utilized to reduce the concentration of molecules (e.g., proteins) in the cell-containing compartment (e.g., EC space) that are inhibitory to viral yield. For example, these inhibitory molecules can be selectively diluted or removed from the EC space where the host cells and virus are grown. In single pass perfusion of the bioreactor, depending on the molecular weight (MW) cutoff, these inhibitory molecules could readily cross the fiber membrane (via dialysis) into the IC space and be removed from the culture. This is the normal procedure used to provide fresh media and remove metabolic waste via the media feed pump. Fiber membranes with the necessary MW cutoff can be selected (e.g., 5K, 10K, 40K, 80K), and the pump rate can be increased or decreased to effectively control the concentration of these inhibitory molecules.

Another technique to minimize accumulation of inhibitory molecules is to use the harvest/factor pump. This delivers and removes media from the EC side of the bioreactor. If the MW is too large for the inhibitory molecule to cross the fiber membrane into the IC space, increased or periodic removal of EC medium will remove product or these inhibitory molecules simultaneously. It may be desirable to supplement with additional protein (e.g., FBS) to offset the loss due to an increased harvest rate.

A third technique to reduce inhibitory molecules is to pass the harvest (EC side) or feed stream (IC side) media through a membrane filter (e.g., anion exchange) to specifically bind the inhibitory molecule(s). By doing this, the media can then be recirculated through the bioreactor again until the metabolic waste reaches toxic levels. In this mode, the bioreactor would act as a compartment to house cells and the tank would house the basal media (essentially a large stirred tank with the cells confined to a small space). Also, depending on the size of the inhibitory molecules, tangential flow filtration can be used to remove inhibitory molecules based on MW. Again, it may be desirable supplement the media with protein and recirculate the media back through the bioreactor.

Of the aforementioned approaches, if the inhibitory molecule(s) do not cross the fiber membrane, the preferred approach is to use of the harvest pump to increase the flow rate shortly after viral infection of the host cells, thereby preventing the concentration of inhibitory molecules in the EC space from reaching a level that compromises virus yield (e.g., from reaching a level that signals apoptosis of the host cells).

Example 2

Automated Purification of Human Influenza Virus

In a particular embodiment of the invention, the automated method involves purifying a human influenza virus using the steps outlined below and using the purification unit shown schematically in FIG. 32.

Supernatant Source:

Filtered supernatant containing the unpurified virus is produced in an automated cell culture device (e.g., the AUTOVAXID™ cell culture module). Once the desired quantity of virus has been produced the automated purification module is connected to the cell culture device. The filtered supernatant is transferred to the automated purification unit by a pump.

Column Set-Up:

A pre-sterilized, disposable, glass 2.5×10 cm column is packed with GeHealthcare QSFF chromatography resin and snapped into the automated unit which also includes a UV monitor and electronic data recorder. Using the automated purification unit as shown in FIG. 32, equilibration buffer is flowed through the column at a pump rate of 9 mL/min. This same pump rate is used throughout the process. The column is then equilibrated with 20 mM phosphate, 0.65M NaCl at pH 7.3.

Purification:

Filtered supernatant is passed through a heater to warm it to ambient temperature prior to entering the column. Once all of the supernatant has entered the column, the column is washed with PBS to remove unbound impurities. The purified virus is eluted from the column using 20 mM phosphate, 1.57 M NaCl at a pH of 7.3. The UV absorbing peak containing the purified virus is collected and sent to a mixing chamber for further processing.

Sanitization of Diafiltration Apparatus:

A membrane based ultrafiltration device is installed in the automated purification module. This cassette or device contains a membrane of 50 $cm^2$ area having a nominal pore size of 0.1 micron. This device works on the tangential flow filtration principle whereby molecules greater than 0.1 micron, such as the human influenza virus, cannot pass through the membrane but small molecules, such as buffers, host cell proteins and virus fragments can pass through. The tangential flow filtration cassette is used to exchange one buffer for another and is a more efficient substitute for dialysis. After installation, the tangential flow filter (TFF) cassette and system is sanitized using 0.1N Sodium Hydroxide at a crossflow or feed rate of 20-40 mL/min. This cross flow rate is maintained throughout the process. After sanitization is complete the 0.1N Sodium Hydroxide is flushed out of the system using phosphate buffered saline at pH 7.4. The virus is then introduced into the system.

Buffer Exchange.

The virus phosphate buffered saline at pH 7.4 phosphate buffered saline at pH 7.4 elution.

Final Filtering.

The virus-containing final buffer solution is further purified by filtering the solution through a filter having a pore size of approximately 0.22 μm.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for the production of virus and virus-like particles (VLP), comprising culturing virus-infected cells in an apparatus comprising:
   a hollow fiber bioreactor comprising an intracapillary space, an extracapillary space, and a hollow fiber membrane separating the intracapillary space and the extracapillary space,
   an intracapillary circuit that includes the intracapillary space of the bioreactor, and
   an extracapillary circuit that includes the extracapillary space of the bioreactor, wherein the cells are cultured in a culture medium in the extracapillary space of the bioreactor;
   circulating the culture medium through the bioreactor, wherein the culture medium passes through the hollow fiber membrane, and
   reducing the concentration of a molecule in the culture medium that is inhibitory to virus or VLP yield from the cells in the extracapillary space by:
   (a) diluting or removing the inhibitory molecule from the extracapillary space, or
   (b) increasing or removing culture medium from the extracapillary space, wherein the inhibitory molecule is a size that prevents passage of the inhibitory molecule through the hollow fiber membrane to the intracapillary space, or
   (c) passing the culture medium through a membrane filter that specifically binds the inhibitory molecule, and recirculating the culture medium through the bioreactor.

2. The method of claim 1, wherein the inhibitory molecule is encoded by the virus.

3. The method of claim 1, wherein the inhibitory molecule is a molecule produced by the virus-infected cells.

4. The method of claim 1, wherein the inhibitory molecule contributes to the apoptosis of the cells before or after viral infection.

5. The method of claim 1, wherein the inhibitory molecule induces an interferon response from the virus-infected cells.

6. The method of claim 1, wherein the inhibitory molecule comprises an oxidative stress factor.

7. The method of claim 1, wherein the inhibitory molecule comprises a plurality of inhibitory molecules.

8. The method of claim 1, wherein the inhibitory molecule comprises non-structural (NS) protein, viral ribonucleoprotein (RNP), or both.

9. The method of claim 1, wherein the culture conditions allow for diluting the inhibitory molecules in the cell culture medium within the first compartment.

10. The method of claim 1, further comprising monitoring the concentration of the inhibitory molecule in the hollow fiber bioreactor.

11. The method of claim 1, wherein said reducing comprises (a) diluting or removing the inhibitory molecule from the extracapillary space.

12. The method of claim 1, wherein said reducing comprises (b) increasing or removing culture medium from the extracapillary space, wherein the inhibitory molecule is a size that prevents passage of the inhibitory molecule through the hollow fiber membrane to the intracapillary space.

13. The method of claim 1, wherein said reducing comprises (c) passing the culture medium through a membrane filter that specifically binds the inhibitory molecule, and recirculating the culture medium through the bioreactor.

14. The method of claim 1, wherein at least a portion of the extracapillary space is occupied by virus-infected cells producing virus at a rate of at least 1,000 particles per cell for budding virus or at a rate of at least 10,000 particles per cell for lytic virus.

15. The method of claim 1, wherein the virus-infected cells are infected with influenza virus.

16. The method of claim 15, wherein the influenza virus is strain H5N1 or str